US006867202B1

(12) United States Patent
Carpino et al.

(10) Patent No.: US 6,867,202 B1
(45) Date of Patent: Mar. 15, 2005

(54) TREATMENT OF INSULIN RESISTANCE

(75) Inventors: Philip Albert Carpino, Groton, CT (US); Charles Kwok-Fung Chiu, Guilford, CT (US); Lydia Codetta Pan, Mystic, CT (US); Bruce Allen Lefker, Gales Ferry, CT (US); Judith Lee Treadway, Mystic, CT (US); Michael Paul Zawistoski, West Warwick, RI (US)

(73) Assignee: Pfizer Inc., New York, NY (US)

( * ) Notice: Subject to any disclaimer, the term of this patent is extended or adjusted under 35 U.S.C. 154(b) by 1 day.

(21) Appl. No.: 10/626,198

(22) Filed: Jul. 22, 2003

Related U.S. Application Data

(62) Division of application No. 10/158,649, filed on May 29, 2002, now Pat. No. 6,630,487, which is a division of application No. 09/380,186, filed as application No. PCT/IB98/00876 on Jun. 5, 1998, now Pat. No. 6,448,263.
(60) Provisional application No. 60/050,790, filed on Jun. 25, 1997.

(51) Int. Cl.$^7$ ...................... A61K 31/33; A61K 31/435; A61K 31/415; C07D 471/04; C07D 231/54

(52) U.S. Cl. .................... 514/183; 514/303; 514/19; 514/403; 514/405; 546/118; 546/119; 546/120; 548/360.5; 548/360.1; 548/363.1; 548/364.1; 548/366.1

(58) Field of Search ................................ 514/183, 303, 514/19, 403, 405; 546/118, 119, 120, 360.5; 548/363.1, 364, 366.1

(56) References Cited

U.S. PATENT DOCUMENTS

| | | | |
|---|---|---|---|
| 3,202,660 A | 8/1965 | Zeile et al. | 260/254 |
| 3,235,550 A | 2/1966 | Behner et al. | 260/243 |
| 4,411,890 A | 10/1983 | Momany | 424/177 |
| 4,544,664 A | 10/1985 | Karjalainen et al. | 514/396 |
| 5,492,916 A | 2/1996 | Morriello et al. | 514/318 |
| 6,107,306 A | 8/2000 | Carpino et al. | 514/303 |
| 6,110,932 A | 8/2000 | Carpino et al. | 514/303 |
| 6,124,264 A | 9/2000 | Carpino et al. | 514/19 |
| 6,127,391 A | 10/2000 | Hansen et al. | 514/343 |
| 6,248,717 B1 | 6/2001 | Carpino et al. | 514/19 |
| 6,448,263 B1 | 9/2002 | Carpino et al. | 514/303 |

FOREIGN PATENT DOCUMENTS

| | | | | |
|---|---|---|---|---|
| WO | WO 9303419 | 2/1993 | | G03C/7/305 |
| WO | WO 9411012 | 5/1994 | | A61K/37/00 |
| WO | WO 9413696 | 6/1994 | | C07K/5/02 |
| WO | 9513069 | * | 5/1995 | |
| WO | WO 9513069 | 5/1995 | | A61K/31/445 |
| WO | WO 9708166 | 3/1997 | | C07D/401/12 |
| WO | WO 9709060 | 3/1997 | | A61K/38/27 |
| WO | WO 9723508 | 7/1997 | | C07K/14/60 |
| WO | WO 9724369 | 7/1997 | | C07K/5/06 |
| WO | WO 9858947 | 12/1998 | | C07K/5/023 |

OTHER PUBLICATIONS

Aloi, et al., "Neuroendocrine Responses to a Novel Growth Homone Secretagogue, L–692,429, in Healthy Older Subjects", *Journal of Endocrinology and Metabolism* 79(4), pp 943–949 (1994).

Aloia, et al., "Effects of Growth Homone in Osteoporosis", *Journal of Clin. Endocrinol Metab.* 43, pp. 992–999 (1976).

Arce, et al., "Synergistic Effect of Growth Hormone–Releasing Hormone (GHRH) and clonidine in Stimulating GH Release in Yound and Old Dogs", *Brain Research* 537, pp. 359–362 (1990).

Arvat, et al., "Synergistic Effect of Growth Hormone–Releasing Hormone Restore the Blunted Growth Hormone–Releasing Activity of Hexarelin in Elderly Subjects", *Journal of Clinical Endocrinology and Metabolism* 79(5), pp. 1140–1143 (1994).

Binnerts, et al., "The Effects of Human Growth Hormone Administration in elderly Adults with Recent Weight Loss", *Journal of Clinical Endocrinology and Metabolism* 67(6), pp. 1312–1316 (1988).

Cella, et al., "Combined Administration of Growth–Hormone Releasing Hormone and Clonidine Restores Defective Growth Hormone Secretion in Old Dogs", *Neuroendocrinology* 57, pp. 432–438 (1993).

Cella, et al., "Presynaptic a2–Adrenergic Stimulation Leads to Growth Hormone Release in the Dog", *Life Sciences* 34, pp. 447–454 (1984).

(List continued on next page.)

Primary Examiner—Richard L. Raymond
Assistant Examiner—Sudhaker B. Patel
(74) Attorney, Agent, or Firm—John A. Wichtowski; Todd M. Crissey

(57) ABSTRACT

This invention is directed to methods of treating insulin resistance in a mammal which comprise administering an effective amount of a compound of formula I,

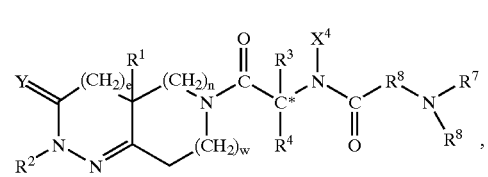

where the variables are defined in the specification, or the stereoisomeric mixtures, diastereomerically enriched, diastereomerically pure, enantiomerically enriched or enantiomerically pure isomers, or the pharmaceutically acceptable salts and prodrugs thereof to said mammal. The compounds of formula I are growth hormone secretagogues and as such are useful for increasing the level of endogenous growth hormone. In another aspect this invention provides certain intermediates which are useful in the synthesis of the foregoing compounds and certain processes useful for the synthesis of said intermediates and th compounds of formula I. This invention is further directed to methods comprising administering to a human or other animal a combination of a functional somatostatin antagonist such as an alpha-2 adrenergic agonist and a compound of formula I.

8 Claims, No Drawings

OTHER PUBLICATIONS

Feek, et al., "The Effect of Bromocriptine on Insulin Secretion and Glucose Tolerance in Patients with Acromegaly", *Clinical Endocrinology* 15, pp. 473–478 (1981).

Gertz, et al., "L–692,429, a Nonpeptide Growth Homone (GH) Secretagogue, Reverses Glucocorticoid Suppression of GH Secretion", *Journal of Clinical Endocrinology and Metabolism* 79(3), pp. 745–749 (1994).

Hampshire, et al., "Clonidine of Xylazine as Provocative Tests fro Growth Hormone Secretion in the Dog", *Am. Journal of Vet. Research* 42(6), pp. 1073–1076 (1981).

Hansen, et al., "Insulin Resistance in Acromegaly: Defects in Both Hepatic and Extrahepatic Insulin Action" *Am. Journ. Physiol.* 250, pp. E269–E273 (1986).

Jacks, et al., "Effect of Acute and Repeated Intravenous Administration of I–692,585, a Novel Non–Peptidyl Growth Hormone Secreagogue, on Plasma Growth Hormone, IGF–1, ACTH, Cortisol, Prolactin, Insulin, and Thyroxine Levels in Beagles", *Journal of Endocrinology* 143, pp. 399–406 (1994).

Jorgensen, et al., "Beneficial Effects of Growth Hormone Treatment in GH–Deficient Adults", *The Lancet*, pp. 1221–1224 (1989).

Levine, et al., "Cryohypophysectomy for Acromegaly", *The American Journal of Medicine*, 57, pp. 526–535 (1974).

Maccario, et al., "Metabolic Modulation of the Growth Hormone–Releasing Activity of Hexarelin in Man", *Metabolism* 44(1), pp. 134–138 (1995).

Marcus, et al., "Effects of Short Term Administration of Recombinant Human Growth Hormone to Elderly People", *Journal of Clinical Endocrinology and Metabolism* 70(2), pp. 519–527 (1990).

Morrison, et al., "Orally Administered Clonidine as a Secretagogue of Growth Hormone and as Thymotrophic Agent in Dogs of Various Ages", *Am. J. Vet. Res.* 51(1), pp. 65–70 (1990).

Rudman, et al., "Effects of Human Growth Hormone on Body Composition in Elderly Men", *Horm. Res.* 36(1), pp. 73–81 (1991).

Richelsen, et al., "Growth Hormone Treatment of Obese Women for 5 wk: Effect on Body Composition and Adipose Tissue LPL Activity", *Am. Journ. Physiol.* 266, pp. E211–E216, (1994).

Thorner, et al., "Growth Hormone–Releasing Hormone and Growth Hormone–Releasing Peptide as Therapeutic Agents to Enhance Growth Hormone Secretion in Disease and Aging", *Recent Progress in Hormone Research* 52, pp. 215–246 (1997).

Thorner, et al., Abstract 76084 of "Growth Hormone–Releasing Hormone and Growth Hormone–Releasing Peptide as Therapeutic Agents to Enhance Growth Hormone Secretion in Disease and Aging".

Valcavi, et al., "Alpha–2–Adrenergic Pathways Release Growth Hormone Via a Non–GRF–Dependent Mechanism in Normal Human Subjects", *Clinical Endocrinology* 29, pp. 309–316 (1988).

\* cited by examiner

TREATMENT OF INSULIN RESISTANCE

CROSS-REFERENCE TO RELATED APPLICATION

This application is a divisional of U.S. patent application Ser. No. 10/158,649, filed on May 29, 2002, now U.S. Pat. No. 6,630,487, which is a divisional of U.S. patent application Ser. No. 09/380,186, filed Aug. 26, 1999, now U.S. Pat. No. 6,448,263, which is the National Stage of International Application No. PCT/IB98/00876, filed Jun. 5, 1998, which was published on Dec. 30, 1998 and which claims benefit of U.S. Provisional Appl. 60/050,790, filed Jun. 25, 1997.

BACKGROUND OF THE INVENTION

Growth hormone (GH), which is secreted from the pituitary gland, stimulates growth of all tissues of the body that are capable of growing. In addition, growth hormone is known to have the following basic effects on the metabolic processes of the body, 1. Increased rate of protein synthesis in substantially all cells of the body;
2. Decreased rate of carbohydrate utilization in cells of the body; and
3. Increased mobilization of free fatty acids and use of fatty acids for energy.

Deficiency in growth hormone results in a variety of medical disorders. In children, it causes dwarfism. In adults, the consequences of acquired GH deficiency include profound reduction in lean body mass and concomitant increase in total body fat, particularly in the tnuncal region. Decreased skeletal and cardiac muscle mass and muscle strength lead to a significant reduction in exercise capacity. Bone density is also reduced. Administration of exogenous growth hormone has been shown to reverse many of the metabolic changes. Additional benefits of therapy have included reduction in LDL cholesterol and improved psychological wellbeing.

In cases where increased levels of growth hormone were desired, the problem was generally solved by providing exogenous growth hormone or by administering an agent which stimulated growth hormone production and/or release. In either case the peptidyl nature of the compound necessitated that it be administered by injection. Initially the source of growth hormone was the extraction of the pituitary glands of cadavers. This resulted in an expensive product, and carried with it the risk that a disease associated with the source of the pituitary gland could be transmitted to the recipient of the growth hormone (e.g., Jacob-Creutzfeld disease). Recently, recombinant growth hormone has become available which, while no longer carrying any risk of dis ase transmission, is still a very expensive product which must be given by injection or by a nasal spray.

Most GH deficiendes are caused by def cts in GH release, not primary defects in pituitary synthesis of GH. Therefore, an alternative strategy for normalizing serum GH levels is by stimulating its release from somatotrophs. Increasing GH secretion can be achieved by stimulating or inhibiting various neurotransmitter systems in the brain and hypothalamus. As a result, the development of synthetic growth hormone-releasing agents to stimulate pituitary GH secretion are being pursued, and may have several advantages over expensive and inconvenient GH replacement therapy. By acting along physiologic regulatory pathways, the most desirable agents would stimulate pulsatile GH secretion, and excessive levels of GH that have been associated with the undesirable side effects of exogenous GH administration would be avoided by virtue of intact negative feedback loops.

Physiologic and pharmacologic stimulators of GH secretion include arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GHRF) or an unknown endogenous growth hormone-releasing hormone or all of these.

Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low. WO 94/13698 refers to certain spiropiperidines and homologues which promote release of growth hormone.

The compounds of WO 94/11012 and WO 94/13696 are reported to be useful in the treatment of osteoporosis in combination with parathyroid hormone or a bisphosphonate.

In one aspect, this invention relates to a method of treating insulin resistant conditions such as Non-Insulin Dependent Diabetes Mellitus (NIDDM) and reduced glycemic control associated with obesity and aging in a mammal in need thereof which comprises administering to said mammal an effective amount of a compound of the formula I, defined below, or a pharmaceutically acceptable salt thereof.

This invention is directed to the use of growth hormone secretagogues specifically growth hormone releasing peptides (GHRP) or GHRP mimetics of formula I, defined below, to improve glycemic control. Agents that increase growth hormone (GH) levels would not be expected to have this effect since it is widely recognized that GH is diabetogenic in animals and in humans. In acromegalics, glucose utilization and suppression of hepatic glucose production are impaired (see Hansen, I., et al., Am J Physiol, 250:E269 (1986)). In this disease of GH excess, impaired glucose handling and hyperinsulinemia have been reversed by pituitary surgery or chemotherapy which reduced GH levels (see Levin S. R., et al., Am J Med, 57:526 (1974; Feek, C. M., et al., J Clin Endocrinol/12:532 (1981)). Furthermore, administration of GH to older subjects caused hyperglycemia, glucose intolerance and hyperinsulinemia in numerous studies (see Aloia, J. F., et al., J Clin Endocrinol Metab, 43:992 (1976); Binnerts et al., J Clin Endocrinol Metab, 67:1312 (1988); Marcus, R., et al., J Clin Endocrinol Metab, 70:519 (1990)). Therefore, GH therapy is contraindicated for individuals with diabetes or those at risk for diabetes.

Obesity is a major risk factor for diabetes, and a large fraction of NIDDM patients are obese. Both conditions are characterized by elevated circulating insulin levels and suppressed GH levels. GH treatment of GH-deficient adults (Jorgensen, J.O.L, et al., Lancet 1:1221 (1989)), obese women (Richelsen, B., et al., Am J Physiol, 266:E211 (1994)) and elderly men (Rudman, D., et al, Horm Res 36 (Suppl 1):73 (1991)) has been shown to produce increases in lean body, hepatic and muscle mass while decreasing fat mass. Thus, GH therapy for obesity would seem attractive except for the diabetogenic effects of GH.

An alternative to exogenous GH administration is therapy that stimulates endogenous GH secretion. It has been shown that a substantial pituitary reserve of GH is present in pituitary-intact GH-deficient patients and the elderly so that decreased serum GH levels are due to hyposecretion.

Hyposecretion of GH in several clinical settings (obesity, aging, glucocorticoid suppression) is relatively resistant to stimulation by GHRH (Gertz, B. J., et al., J Clin Endocrinol M tab, 79:745 (1994); Arvat, E., et al., J Clin Endocrinol Metab, 79:1440 (1994); Maccario, M., et al., Metabolism, 44:134 (1995)). In contrast, administration of a GHRP or combined administration of GHRH and a GHRP in these patients can elicit a robust GH response (Aloi, J. A., et al., J Clin Endocrinol Metab, 79:943; (1994)). Single dose studies of GHRPs have demonstrated the absence of an acute effect on circulating insulin or glucose levels. Insulin and glucose have generally not been monitored in chronic studies except to document the absence of unfavorable changes (Jacks, T., et al., J Endocrinol. 143:399 (1993)).

Prior to the present invention, the use of GHRPs or GHRP mimetics to improve glycemic control has not specifically been explored. The method of treating insulin resistance in a mammal comprising the administration of a compound of formula I is practiced preferentially in patients who have a functional hypothalamic-pituitary axis capable of GH secretory responses to GHRPs and who are diabetics (Type I or Type II), or are insulin resistant, or who show impaired glucose tolerance.

In another aspect, this invention is directed to methods for the treatment or prevention of congestive heart failure, obesity and frailty associated with aging, in a mammal in need thereof, which comprises administering to said mammal simultaneously, sequentially in any order or as a combination a functional somatostatin antagonist such as an alpha-2 adrenergic agonist, for example clonidine, xylazine or medetomidine, and a compound of formula I, defined below. In another aspect, this invention provides methods for accelerating bone fracture repair and wound healing, attenuating protein catabolic response after a major operation, and reducing cachexia and protein loss due to chronic illness in a mammal in need thereof, which comprises administering to said mammal simultaneously, sequentially in any order or as a combination an alpha-2 adrenergic agonist, such as clonidine, xylazine or medetomidine and a compound of formula I, defined below. Clonidine, which is disclosed in U.S. Pat. No. 3,202,660 the disclosure of which is hereby incorporated by reference, xylazine, which is disclosed in U.S. Pat. No. 3,235,550 the disclosure of which is hereby incorporated by reference and medetomidine, which is disclosed in U.S. Pat. No. 4,544,664 the disclosure of which is hereby incorporated by reference. It has been shown that alpha-2 adrenergic agonists cause release of endogenous growth hormone in human and canine subjects (Cella et al., Life Sciences (1984), 34:447–454; Hampshire J, Altszuler N. American Journal of Veterinary Research (1981), 42:6, 1073–1076; Valcavi et al., Clinical Endocrinology (1988), 29:309–316; Morrison et al. American Journal of Veterinary Research (1990), 51:1, 65–70;), and that the coadministration of an alpha-2 adrenergic agonist with growth hormone-releasing factor restores defective growth hormone secretion in aged dogs (Arce et al., Brain Research (1990), 537:359–362; Celia et. al., Neuroendocrinology (1993). 57:432438).

In yet another aspects this invention provides a process for the synthesis of a compound of the formula Z

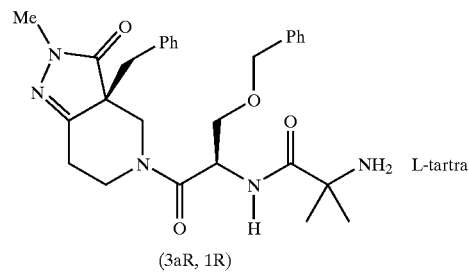

where the process is described below.

Further, this invention is directed to processes for preparing certain intermediates, shown below, which are useful in the synthesis of the compound of formula Z.

The compounds of formula I utilized in the present invention and the compound of formula Z are disclosed and claimed in co-pending PCT Application Number PCT/IB 96101353 filed Dec. 4, 1996, which is assigned to the assignee hereof, wherein said compounds are disclosed as having activity as growth hormone secretagogues and which increase the level of endogenous growth hormone.

SUMMARY OF THE INVENTION

The compounds utilized in methods of this invention have the formula I,

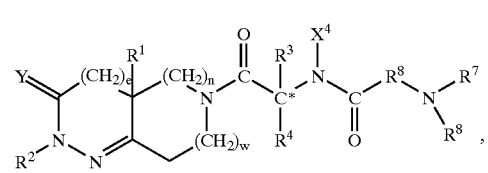

or the stereoisomeric mixtures, diastereomerically enriched, diastereomerically pure, enantiomerically enriched or enantiomerically pure isomers, or the pharmaceutically acceptable salts and prodrugs thereof,
wherein
e is 0 or 1;
n and w are each independently 0, 1 or 2;
provided that w and n cannot both be 0 at the same time;
Y is oxygen or sulfur;
$R^1$ is hydrogen, —CN, $(CH_2)_qN(X^6)C(O)X^5$, —$CH_2)_qN(X^6)C(O)(CH_2)_t$—$A^1$, —$(CH_2)_qN(X^5)SO_2(CH_2)_t$—$A^1$, —$(CH_2)_qN(X^6)SO_2)X^6$, —$(CH_2)_qN(X^5)C(O)N(X^6)(CH_2)_t$—$A^1$, —$(CH_2)_qN(X^6)C(O)N(X^6)(X^5)$, —$(CH_2)_qC(O)N(X^6)(X^5)$, —$(CH_2)_qC(O)N(X^6)(CH_2)_t$—$A^1$, —$(CH_2)_qC(O)OX^6$, —$(CH_2)_qC(O)O(CH_2)_t$—$A^1$, —$(CH_2)_qOX^5$, —$(CH_2)_qOC(O)X^6$, —$(CH_2)_qOC(O)(CH_2)_t$—$A^1$, —$(CH_2)_qOC(O)N(X^6)(CH_2)_t$—$A^1$, —$(CH_2)_qOC(O)N(X^6)(X^6)$, —$(CH_2)_qC(O))X^6$, —$(CH_2)_qC(O)(CH_2)_t$—$A^1$, —$(CH_2)_qN(X^6)C(O)OX^6$, —$(CH_2)_qN(X^6)SO_2N(X^5)(X^6)$, —$(CH_2)_qS(O)_mX^6$, —$(CH_2)_qS(O)_m(CH_2)_t$—$A^1$, —$(C_1-C_{10})$alkyl, —$(CH_2)_tA^1$, —$(CH_2)_q$—$(C_3-C_7)$cycloalkyl, —$(CH_2)_q$—$Y^1$—$(C_1-C^6)$alkyl, —$(CH_2)_q$—$Y^1(CH_2)_t$—$A^1$ or —$(CH_2)_q$—$Y_1$—$(CH_2)_t(C_3-C_7)$cycloalkyl;
where the alkyl and cycloalkyl groups in the definition of $R^1$ are optionally substituted with $(C_1-C_4)$alkyl, hydroxyl, $(C_1-C_4)$alkoxy, carboxyl, —$CONH_2$, —$S(O)_m(C_1-C_5)$alkyl, —$CO(C_1-C_4)$alkyl ester, 1H-tetrazol-5-yl or 1, 2 or 3 fluoro;

$Y^1$ is O, $S(O)_m$, —C(O)$NX^6$—, —CH=CH—, —C≡C—, —N($X^5$)C(O)—, —C(O)N$X^6$—, —C(O)O—, —OC(O)N($X^6$)— or —OC(O)—;

q is 0, 1, 2, 3 or 4;

t is 0, 1, 2 or 3;

said $(CH_2)_q$ group and $(CH_2)_t$ group may each be optionally substituted with hydroxyl, $(C_1-C_4)$alkoxy, carboxyl, —$CONH_2$, —$S(O)_m(C_1-C_6)$alkyl, —$CO_2(C_1-C_4)$alkyl ester, 1H-tetrazol-5-yl, 1, 2 or 3 fluoro, or 1 or 2 $(C_1-C_4)$alkyl;

$R^2$ is hydrogen, $(C_1-C_8)$alkyl, —$(C_0-C_3)$alkyl-$(C_3-C_8)$cycloalkyl, —$(C_1-C_4)$alkyl-$A^1$ or $A^1$;

where the alkyl groups and the cycloalkyl groups in the definition of $R^2$ are optionally substituted with hydroxyl, —C(O)$OX^6$, —C(O)N($X^5$)($X^6$), —N($X^6$)($X^6$), —$S(O)_m(C_1-C_6)$alkyl, —C(O)$A^1$, —C(O)($X^6$), $CF_3$, CN or 1, 2 or 3 halogen;

$R^3$ is $A^1$, $(C_1-C_{10})$alkyl, —$(C_1-C_6)$alkyl-$A^1$, —$(C_1-C_5)$alkyl-$(C_3-C_7)$cycloalkyl, —$(C_1-C_5)$alkyl-$X^1$—$(C_1-C_5)$alkyl, —$(C_1-C_5)$alkyl-$X^1$—$(C_0-C_5)$alkyl-$A^1$ or —$(C_1-C_5)$alkyl-$X^1$—$(C_1-C_5)$alkyl-$(C_3-C_7)$cycloalkyl;

where the alkyl groups in the definition of $R^3$ are optionally substituted with —$S(O)_m(C_1-C_6)$alkyl, —C(O)$OX^3$, 1, 2, 3, 4 or 5 halogens, or 1, 2 or 3 $OX^3$; $X^1$ is O, $S(O)_m$, —N($X^2$)C(O)—, —C(O)N($X^2$)—, —OC(O)—, —C(O)O—, $CX^2$=$CX^2$—, —N($X^2$)C(O)O—, —CC(O)N($X^2$)— or —C≡C—;

$R^4$ is hydrogen, $(C_1-C_6)$alkyl or $(C_3-C_7)$cycloalkyl, or $R^4$ is taken together with $R^3$ and the carbon atom to which they are attached and form $(C_5-C_7)$cycloalkyl, $(C_5-C_7)$cycloalkenyl, a partially saturated or fully saturated 4- to 8-membered ring having 1 to 4 heteroatoms independently selected from the group consisting of oxygen, sulfur and nitrogen, or is a bicyclic ring system consisting of a partially saturated or fully saturated 5 or 6-membered ring, fused to a partially saturated, fully unsaturated or fully saturated 5 or 6-membered ring, optionally having 1 to 4 heteroatoms independently selected from the group consisting of nitrogen, sulfur and oxygen;

$X^4$ is hydrogen or $(C_1-C_6)$alkyl or $X^4$ is taken together with $R^4$ and the nitrogen atom to which $X^4$ is attached and the carbon atom to which $R^4$ is attached and form a five to seven membered ring;

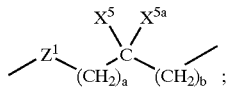

$R^6$ is a bond or is where a and b are independently 0, 1, 2 or 3;

$X^5$ and $X^{5a}$ are each independently selected from the group consisting of hydrogen, trifluoromethyl, $A^1$ and optionally substituted $(C_1-C_6)$alkyl;

the optionally substituted $(C_1-C_5)$alkyl in the definition of $X^5$ and $X^{5a}$ is optionally substituted with a substituent selected from the group consisting of $A^1$, $OX^2$, —$S(O)_m(C_1-C^6)$alkyl, —C(O)$OX^2$, $(C_3-C_7)$cycloalkyl, —N($X^2$)($X^2$) and —C(O)N($X^2$)$X^2$);

or the carbon bearing $X^5$ or $X^{5a}$ forms one or two alkylene bridges with the nitrogen atom bearing $R^7$ and $R^8$ wherein each alkylene bridge contains 1 to 5 carbon atoms, provided that when one alkylene bridge is formed then $X^5$ to $X^{5a}$ but not both may be on the carbon atom and $R^7$ or $R^8$ but not both may be on the nitrogen atom and further provided that when two alkylene bridges are formed then $X^5$ and $X^{5a}$ cannot be on the carbon atom and $R^7$ and $R^5$ cannot be on the nitrogen atom;

or $X^5$ is taken together with $X^{5a}$ and the carbon atom to which they are attached and form a partially saturated or fully saturated 3 to 7-membered ring, or a partially saturated or fully saturated 4- to 8-membered ring having 1 to 4 heteroatoms independently selected from the group consisting of oxygen, sulfur and nitrogen;

or $X^5$ is taken together with $X^{5a}$ and the carbon atom to which they ar attached and form a bicyclic ring system consisting of a partially saturated or fully saturated 5- or 6-membered ring, optionally having 1 or 2 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

$Z^1$ is a bond, O or N—$X^2$, provided that when a and b are both 0 then $Z^1$ is not N—$X^2$ or O;

$R^7$ and $R^8$ are independently hydrogen or optionally substituted $(C_1-C_6)$alkyl;

where the optionally substituted $(C_1-C_6)$alkyl in the definition of $R^7$ and $R^8$ is optionally independently substituted with $A^1$, —C(O)O—$(C_1-C_6)$alkyl, —$S(O)_m(C_1-C_6)$alkyl, 1 to 5 halogens, 1 to 3 hydroxy, 1 to 3 —O—C(O)($C_1-C_{10}$)alkyl or 1 to 3 $(C_1-C_6)$alkoxy; or $R^7$ and $R^8$ can be taken together to form —$(CH_2)_r$—L—$(CH_2)_r$—;

where L is C($X^2$)($X^2$), $S(O)_m$ or N($X^2$);

$A^1$ for each occurrence is independently $(C_5-C_7)$cycloalkenyl, phenyl or a partially saturated, fully saturated or fully unsaturated 4- to 8-membered ring optionally having 1 to 4 heteroatoms independently selected from the group consisting of oxygen, sulfur and nitrogen, a bicyclic ring system consisting of a partially saturated, fully unsaturated or fully saturated 5- or 6-membered ring, optionally having 1 to 4 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

$A^1$ for each occurrence is independently optionally substituted, in one or optionally both rings if $A^1$ is a bicyclic ring system, with up to three substituents, each substituent independently selected from the group consisting of F, Cl, Br, I, $OCF_3$, $OCF_2H$, $CF_3$, $CH_3$, $OCH_3$, —$OX^6$, —C(O)N($X^5$)($X^6$), —C(O)$OX^6$, oxo, $(C_1-C_5)$alkyl, nitro, cyano, benzyl, —$S(O)_m(C_1-C_6)$alkyl, 1H-tetrazol-5-yl, phenyl, phenoxy, phenylalkyloxy, halophenyl, methylenedioxy, —N($X^5$)($X^6$), —N($X^5$)C(O)($X^5$), —$SO_2$N($X^6$)($X^5$), —N($X^5$)$SO_2$-phenyl, —N($X^5$)$SO_2X^6$, —CON$X^{11}X^{12}$, —$SO_2NX^{11}X^{12}$, —$NX^6SO_2X^{12}$, —$NX^6CONX^{11}X^{12}$, —$NX_5SO_2NX^{11}X^{12}$, —$NX^6$C(O)$X^{12}$, imidazolyl, thiazolyl and tetrazolyl, provided that if $A^1$ is optionally substituted with methylenedioxy then it can only be substituted with one methylenedioxy, where $X^{11}$ is hydrogen or optionally substituted $(C_1-C_6)$alkyl;

the optionally substituted $(C_1-C_6)$alkyl defined for $X^{11}$ is optionally independently substituted with phenyl, phenoxy, $(C_1-C_6)$alkoxycarbonyl, —S(O)

$_m(C_1-C_6)$alkyl, 1 to 5 halogens, 1 to 3 hydroxy, 1 to 3 $(C_1-C_{10})$alkanoyloxy or 1 to 3 $(C_1-C_6)$alkoxy;

$X^{12}$ is hydrogen, $(C_1-C_6)$alkyl, phenyl, thiazolyl, imidazolyl, furyl or thienyl, provided that when $X^{12}$ is not hydrogen, $X^{12}$ is optionally substituted with one to three substituents independently selected from the group consisting of Cl, F, $CH_3$, $OCH_3$, $OCF_3$ and $CF_3$;

or $X^1$ and $X^{12}$ are taken together to form $-(CH_2)_r-L^1-(CH_2)_r-$;

where $L^1$ is $C(X^2)(X^2)$, O, $S(O)_m$ or $N(X^2)$;

r for each occurrence is independently 1, 2 or 3;

$X^2$ for each occurrence is independently hydrogen, optionally substituted $(C_1-C_6)$alkyl, or optionally substituted $(C_3-C_7)$cycloalkyl, where the optionally substituted $(C_1-C_4)$alkyl and optionally substituted $(C_3-C_7)$ cycloalkyl in the definition of $X^2$ are optionally independently substituted with $-S(O)_m(C_1-C_6)$alkyl, $-C(O)$ $OX^3$, 1 to 5 halogens or 1–3 $OX^3$;

$X^3$ for each occurrence is independently hydrogen or $(C_1-C_6)$alkyl;

$X^5$ is independently hydrogen, optionally substituted $(C_1-C_6)$alkyl, $(C_2-C_6)$halogenated alkyl, optionally substituted $(C_3-C_7)$cycloalkyl, $(C_3-C_7)$-halogenatedcycloalkyl, where optionally substituted $(C_1-C_6)$alkyl and optionally substituted $(C_3-C_7)$ cycloalkyl in the definition of $X^6$ is optionally independently substituted by 1 or 2 $(C_1-C_4)$alkyl, hydroxyl, $(C_1-C_4)$alkoxy, carboxyl, $CONH_2$, $-S(O)_m(C_1-C_6)$ alkyl, carboxylate $(C_1-C_4)$alkyl ester, or 1H-tetrazol-5-yl; or when there are two $X^6$ groups on one atom and both $X^6$ are independently $(C_1-C_6)$alkyl, the two $(C_1-C_6)$alkyl groups may be optionally joined and, together with the atom to which the two $X^6$ groups are attached, form a 4 to 9 membered ring optionally having oxygen, sulfur or $NX^7$;

$X^7$ is hydrogen or $(C_1-C_6)$alkyl optionally substituted with hydroxyl; and m for each occurrence is independently 0, 1 or 2;

with the proviso that $X^5$ and $X^{12}$ cannot be hydrogen when it is attached to C(O) or $SO_2$ in the form $C(O)X^6$, $C(O)X^{12}$, $SO_2X^6$ or $SO_2X^{12}$; and when $R^1$ is a bond then L is $N(X^2)$ and each r in the definition $-(CH_2)_r-L-(CH_2)_r-$ is independently 2 or 3.

In one aspect, this invention provides a method for treating insulin resistance in a mammal which comprises administering to said mammal an effective amount of a compound of formula I, as defined above, or the stereoisomeric mixtures, diastereomerically enriched, diastereomerically pure, enantiomerically enriched or enantiomerically pure isomers, or the pharmaceutically acceptable salts and prodrugs thereof.

A preferred method of the foregoing method is where the condition associated with insulin resistance is type I diabetes, type II diabetes, hyperglycemia, impaired glucose tolerance or an insulin resistant syndrome or state.

Another preferred method of the foregoing method is where the condition associated with insulin resistance is associated with obesity or old age.

A preferred method of the foregoing method is where said compound of formula I is of the following formula

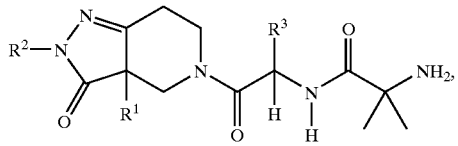

or the stereoisomeric mixtures, diastereomerically enriched, diastereomerically pure, enantiomerically enriched or enantiomerically pure isomers, or the pharmaceutically acceptable salts and prodrugs thereof where $R^1$ is $-CH_2$-phenyl, $R^2$ is methyl and $R^3$ is $-(CH_2)_3$-phenyl;

$R^1$ is $-CH_2$-phenyl, $R^2$ is methyl and $R^3$ is 3-indolyl-$CH_2-$:

$R^1$ is $-CH_2$-phenyl, $R^2$ is ethyl and $R^3$ is 3-indolyl-$CH_2-$;

$R^1$ is $CH_2$-fluoro-phenyl, $R^2$ is methyl and $R^3$ is 3-indolyl-$CH_2-$;

$R^1$ is $-CH_2$-phenyl, $R^2$ is methyl and $R^3$ is $-CH_2-O-CH_2$-phenyl;

$R^1$ is $CH_2$-phenyl, $R^2$ is ethyl and $R^3$ is $-CH_2O-CH_2$-phenyl;

$R^1$ is $-CH_2$-phenyl, $R^2$ is $-CH_2CF_3$ and $R^3$ is $-CH_2-O-CH_2$-phenyl;

$R^1$ is $CH_2$-4-fluorophenyl, $R^2$ is methyl and $R^3$ is $-CH_2O-CH_2$-phenyl;

$R^1$ is $-CH_2$-phenyl, $R^2$ is t-butyl and $R^3$ is $-CH_2O-CH_2$-phenyl; or $R^1$ is $-CH_2$-phenyl, $R^2$ is methyl and $R^3$ is $-CH_2-O-CH_2$-3,4-difluoro-phenyl.

Another preferred method of the foregoing method is where said compound of formula I is of the formula

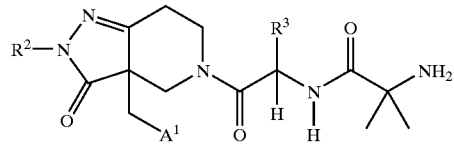

or the stereoisomeric mixtures, diastereomerically enriched, diastereomerically pure, enantiomerically enriched or enantiomerically pure isomers, or the pharmaceutically acceptable salts and prodrugs thereof where $R^2$ is methyl; $A^1$ is 2-pyridyl; and $R^3$ is $-CH_2-O-CH_2$-phenyl;

$R^2$ is $CH_2CF_3$; $A^1$ is 2-pyridyl; and $R^3$ is $-CH_2-O-CH_2$-chloro-phenyl;

$R^2$ is $CH_2CF_3$; $A^1$ is 2-pyridyl; and $R^3$ is $-CH_2-O-CH_2$-4-chloro-phenyl;

$R^2$ is $CH_2CF_3$; $A^1$ is 2-pyridyl; and $R^3$ is $-CH_2-O-CH_2$-2,4-dichloro-phenyl;

$R^2$ is $CH_2CF_3$; $A^1$ is 2-pyridyl; and $R^3$ is $-CH_2-O-CH_2$-3-chloro-thiophene or $R^2$ is $CH_2CF_3$; $A^1$ is 2-pyridyl; and $R^3$ is $-CH_2-O-CH_2$-2,4-di-fluoro-phenyl.

Yet another preferred method of the foregoing method is where said compound of formula I or the stereoisomeric mixtures, diastereomerically enriched, diastereomerically pure, enantiomerically enriched or enantiomerically pure isomers or the pharmaceutically acceptable salts and prodrugs thereof is the 3a(R,S),1(R) diastereomeric mixture, the 3a(R),1(R) diastereomer or the 3a(S),1(R) diastereomer of a compound selected from the group consisting of 2-amino-N-[1-(3a-benzyl-2-methyl-3-oxo-2,3,3a,4,6,7-hexahydro-pyrazolo[4,3-c]pyridine-5-carbonyl)₄-phenyl-butyl]-isobutyramide, 2-amino-N-[2-(3a-benzyl-2-methyl-1-3-oxo-2,3,3a,4,6,7-hexahydro-pyrazolo-[4,3-c]pyridin-5-yl)-1-(1H-indol-3-ylmethyl)-2-oxo-ethyl]isobutyramide, 2-amino-N-[2-(3a-benzyl-2-ethyl-3-oxo-2,3,3a,4,6,7-hexahydro-pyrazolo[4,3-c]pyridin-5-yl)-1-(1H-indol-3-ylmethyl)-2-oxo-ethyl]isobutyramide, 2-amino-N-[2-[3a-(4-fluoro-benzyl)-2-methyl-3-oxo-2,3,3a,4,6,7-hexahydro-pyrazolo[4,3-c]pyridin-5-yl]-1-(1H-indol-3-ylmethy)-2-oxo-ethyl]isobutyramide, 2-amino-N-[2-(3a-benzyl-2-methyl-3-oxo-2,3,3a,4,6,7-hexahydro-pyrazolo[4,3-c]pyridin-5-yl)-1-benzyloxymethyl-2-oxo-ethyl]-isobutyramide, 2-amino-N-[2-(3a-benzyl 2-ethyl-3-oxo-2,3,3a,4,6,7-hexahydro-pyrazolo[4, c]pyridin-5-yl)-1-benzyloxymethyl-2-oxo-ethyl]-isobutyramide, 2-amino-N-2-[3a-benzyl-3-oxo-2-(2,2,2-trifluaro-ethyl)-2,3,3a,4,6,7-hexahydro-pyrazolo[4,3-c]pyridin-5-yl]-1-benzyloxymethyl-2-oxo-ethyl]-isobutyramide, 2-amino-N-{1-benzyloxymethyl-2-[3a-(4-fluoro-benzyl)-2-methyl-3-oxo-2,3,3a,4,6,7-hexahydro-pyrazolo[4,3-c]pyridin-5-yl]-2-oxo-thyl}-isobutyramide, 2-amino-N-[2-(3a-benzyl-2-tert-butyl-3-oxo-2,3,3a,4,6,7-hexahydro-pyrazolo[4,3-c]pyridin-5-yl)-1-benzyloxymethyl-2-oxo-ethyl]-isobutyramide and 2-amino-N-[2-(3a-benzyl-3-oxo-2,3,3a,4,6,7-hexahydro-pyrazolo[4,3c]pyridin-5-yl)-1-benzyloxymethyl-2-oxo-ethyl]-isobutyramide.

A preferred method of the immediately foregoing method is where said compound of formula I is 2-amino-N-[2-(3a-(R)-benzyl-2-methyl-3-oxo-2,3,3a,4,6,7-hexahydro-pyrazolo-[4,3-c]pyridin-5-yl)-1-(R)benzyloxymethyl-2-oxo-ethyl]-isobutyramide L-tartaric acid salt Still another preferred method of the foregoing method is a method where said compound of formula I or the stereoisomeric mixtures, diastereomerically enriched, diastereomerically pure, enantiomerically enriched or enantiomerically pure isomers or the pharmaceutically acceptable salts and prodrugs thereof is the 3a-(R,S),1-(R) diastereomeric mixture, the 3a-(R),1-(R) enantiomer or 3a-(S),1-(R) enantiomer of a compound selected from the group consisting of 2-amino-N-[1-benzyloxymethyl-2-(2-methyl-3-oxo-3a-pyridin-2-ylmethyl-2,3,3a,4,6,7-hexahydro-pyrazolo[4,3-c]pyridin-5-yl)-2-oxo-ethyl]-2-methyl-propionamide;

2-amino-N-1-{1-chloro-benzyloxymethyl)-2-oxo-2-[3-oxo-3a-pyridin-2-ylmethyl-2-(2,2,2-trifluoro-ethyl)-2,3,3a,4,6,7-hexahydro-pyrazolo[4,3-c]pyridin-5-yl]ethyl}2-methyl-propionamide;

2-amino-N-{1-(4-chloro-benzyloxymethyl)-2-oxo-2-[3-oxo-3a-pyridin-2-ylmethyl-2-(2,2,2-trifluoro-ethyl)-2,3,3a,4,6,7-hexahydro-pyrazolo[4,3-c]pyridin-5-yl]-ethyl}-2-methyl-propionamide;

2-amino-N-{1-(2,4-dichloro-benzyloxymethyl)-2-oxo-2-[3-oxo-3a-pyridin-2-ylmethyl-2-(2,2,2-trifluoro-ethyl)-2,3,3a,4,6,7-hexahydro-pyrazolo[4,3-c]pyridin-5-ethyl}-2-methyl-propionamide;

2-amino-N-{1-(4-chloro-thiophen-2-ylmethoxymethyl)-2-oxo-2-[3-oxo-3a-pyridin-2-ylmethyl-2-(2,2,2-trifluoro-ethyl)-2,3,3a,4,5,7-hexahydro-pyrazolo[3,4-c]pyridin-6-yl]ethyl}-2-methyl-propionamide; and 2-amino-N-{1-(2,4-difluoro-benzyloxymethyl)-2-oxo-2-[3-oxo-3a-pyridin-2-ylmethyl-2-(2,2,2-trifluoro-ethyl)2,3,3a,4,6,7-hexahydro-pyrazolo[4,3-c]pyridin-5-yl]-ethyl}-2-methyl-propionamide.

Even still another preferred method of the foregoing method additionally comprises administering to a mammal in need thereof a growth hormone releasing hormone or a functional analog thereof, which are prepared by methods known in the art and some examples of which are described in European Patent Publication No. EP 511 003.

In another aspect, this invention provides pharmaceutical compositions useful for treating insulin resistance in a mammal which comprises a pharmaceutically acceptable carrier and an effective amount of a compound of formula I, as shown above, or the stereoisomeric mixtures, diastereomerically enriched, diastereomerically pure, enantiomerically enriched or enantiomerically pure isomers, or the pharmaceutically acceptable salts and prodrugs thereof.

In still another aspect, this invention provides methods for increasing levels of endogenous growth hormone, which comprises administering to a human or other animal in need thereof effective amounts of a functional somatostatin antagonist and a compound of formula I, as shown above, or the stereoisomeric mixtures, diastereomerically enriched, diastereomerically pure, enantiomerically enriched or enantiomerically pure isomers, or the pharmaceutically acceptable salts and prodrugs thereof.

In yet another aspect, this invention provides methods of treating or preventing congestive heart failure, obesity or frailty associated with aging, which comprises administering to a mammal in need thereof effective amounts of a functional somatostatin antagonist and a compound of formula I, as shown above, or the stereoisomeric mixtures, diastereomerically enriched, diastereomerically pure, enantiomerically enriched or enantiomerically pure isomers, or the pharmaceutically acceptable salts and prodrugs thereof. Preferred of the immediately foregoing method is where said functional somatostatin antagonist is an alpha-2 adrenergic agonist. Preferred of the immediately foregoing method is where said alpha-2 adrenergic agonist is selected from the group consisting of clonidine, xylazine and medetomidine. Preferred of the immediately foregoing method is where said compound of formula I is 2-amino-N-[2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl]-isobutyramide L-tartaric acid salt.

This invention is also directed to pharmaceutical compositions which comprise a pharmaceutically acceptable carrier, an amount of an alpha-2 adrenergic agonist and an amount of a compound of formula I, as defined above, or the stereoisomeric mixtures, diastereomerically enriched, diastereomerically pure, enantiomerically enriched or enantiomerically pure isomers, or the pharmaceutically acceptable salts and prodrugs thereof.

This invention is further directed to methods of treating insulin resistance in a mammal which comprise administering to a mammal in need thereof an effective amount of a growth hormone releasing peptide or a growth hormone releasing peptide mimetic or a pharmaceutically acceptable salt thereof.

In one aspect this invention is directed to the processes described below, where the "*" indicates stereochemical centers.

A process for the preparation of the compound of formula k,

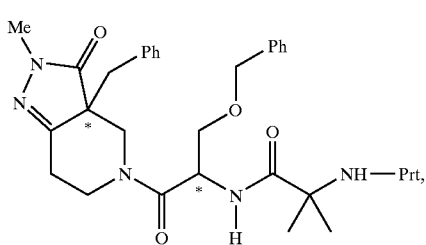
(k)

which comprises reacting the compound of formula g

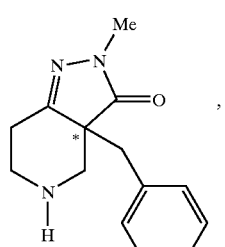
(g)

Free Base with the compound of formula j,

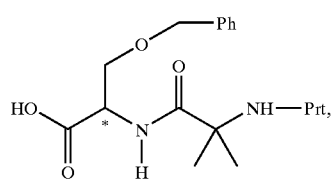
(j)

where Prt is an amine protecting group, in the presence of an organic base, a peptide coupling reagent, and a reaction inert solvent at a temperature between about −78° C. to about −20° C. to yield the compound of formula k.

Preferred of the foregoing process is where the peptide coupling reagent is 1-propane phosphonic acid cyclic anhydride and the compound of formula 9 has the R-configuration, the compound of formula j has the R-configuration and the compound of formula k has the 3a-(R),1-(R) configuration.

A process for the preparation of the compound of formula Z,

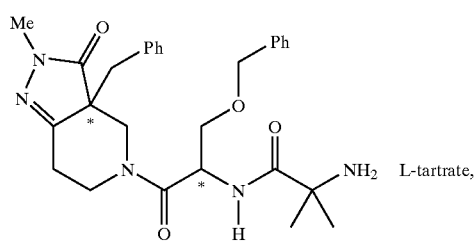
Z which comprises reacting the compound of formula g,

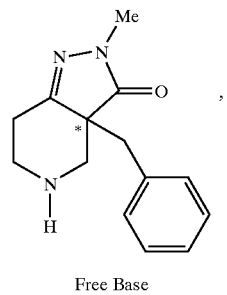
(g)

Free Base with the compound of formula j,

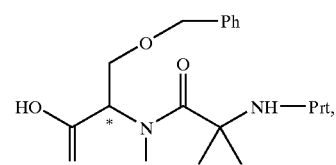
(j)

in the presence of an organic base, a peptide coupling reagent, and a reaction inert solvent at a temperature between about −78° C. to about

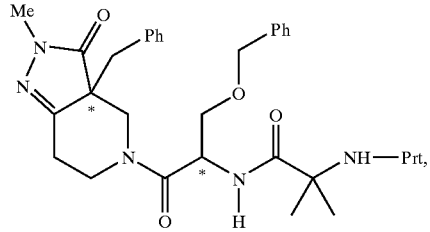
(k)

−20° C. to yield the compound of formula k, deprotecting the compound of formula k to yield the compound of formula I,

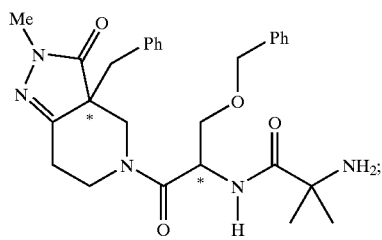
(l)

reacting the compound of formula I with L-tartaric acid in an alcoholic solvent to yield the compound of formula Z.

Preferred of the immediately foregoing process is where the peptide coupling reagent is 1-propane phosphonic acid cyclic anhydride and the compound of formula g has the R-configuration, the compound of formula j has the R-configuration and each of the compounds of formula k, I and Z has the 3a-(R),1-(R) configuration.

A process for the preparation of the compound of formula g,

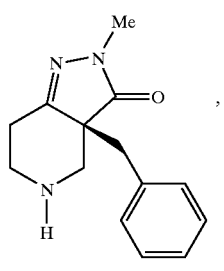

Free Base which comprises reacting the compound of formula f,

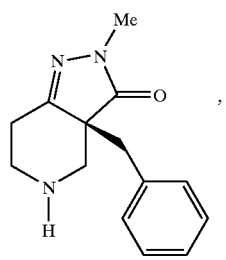

L-Tartrate with a base in an inert solvent at a temperature of about −50 to −10° C. wherein the chirality of the benzyl group is maintained, to yield the compound of formula g.

A process for the preparation of the compound of formula c,

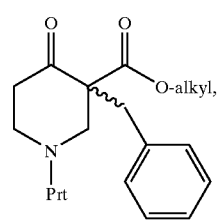

which comprises reacting the compound of formula b,

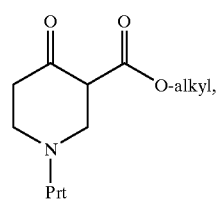

where Prt is an amine protecting group, with an inorganic or organic base and benzyl bromide in a reaction inert solvent to yield the compound of formula c.

A process for the preparation of the compound of formula f,

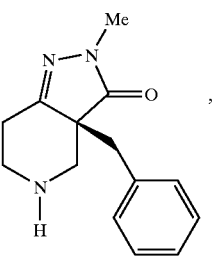

L-Tartrate which comprises reacting the compound of formula e,

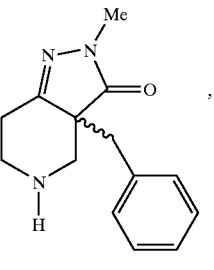

L-Tartrate with L-tartaric acid in a reaction inert organic solvent

This invention also provides the R,S-enantiomeric mixture, the R-enantiomer or the S-enantiomer of the compound of formula

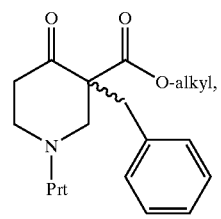

where Prt is hydrogen or an amine protecting group.

DETAILED DESCRIPTION OF THE INVENTION

In general the compounds of formula I or the stereoisomeric mixtures, diastereomerically enriched, diastereomerically pure, enantiomerically enriched or enantiomerically pure isomers, or the pharmaceutically acceptable salts and prodrugs thereof, utilized in methods of the instant invention can be made by processes which include processes known in the chemical arts.

In the above structural formulae and throughout the instant application, the following terms have the indicated meanings unless expressly stated otherwise.

The alkyl groups are intended to include those alkyl groups of the designated length in either a straight or branched configuration which may optionally contain double or triple bonds. Exemplary of such alkyl groups are methyl, ethyl, propyl, isopropyl, butyl, sec-butyl, tertiary butyl, pentyl, isopentyl, hexyl, isohexyl, allyl, ethynyl, propenyl, butadienyl, hexenyl and the like.

When the definition $C_0$-alkyl occurs in the definition, it means a single covalent bond.

The alkoxy groups specified above are intended to include those alkoxy groups of the designated length in either a straight or branched configuration which may optionally contain double or triple bonds. Exemplary of such alkoxy groups are methoxy, ethoxy, propoxy, isopropoxy, butoxy, isobutoxy, tertiary butoxy, pentoxy, isopentoxy, hexoxy, isohexoxy, allyloxy, 2-propynyloxy, isobutenyloxy, hexenyloxy and the like.

The term "halogen" or "halo" is intended to include the halogen atoms fluorine, chlorine, bromine and iodine.

The term "halogenated alkyl" is intended to include an alkyl group as defined hereinabove substituted by one or more halogen atoms as defined hereinabove.

The term "halogenated cycloalkyl" is intended to include a cycloalkyl group substituted by on or more halogen atoms as defined hereinabove.

The term "aryl" is intended to include phenyl and naphthyl and aromatic 5- and 6-membered rings with 1 to 4 heteroatoms or fused 5- or 6-membered bicyclic rings with 1 to 4 heteroatoms of nitrogen, sulfur or oxygen. Examples of such heterocyclic aromatic rings are pyridine, thiophene (also known as thienyl), furan, benzothiophene, tetrazole, indole, N-methylindole, dihydroindole, indazole, N-formylindole, benzimidazole, thiazole, pyrimidine, and thiadiazole.

The chemist of ordinary skill will recognize that certain combinations of heteroatom-containing substituents listed in this invention define compounds which will be less stable under physiological conditions (e.g., those containing acetal or aminal linkages). Accordingly, such compounds are less preferred.

The expression "prodrug" refers to compounds that are drug precursors, which following administration, release the drug in vivo via some chemical or physiological process (e.g., a prodrug on being brought to the physiological pH is converted to the desired drug form). Exemplery prodrugs upon cleavage release the corresponding free acid, and such hydrolyzable ester-forming residues of the compounds of this invention include but are not limited to carboxylic acid substituents (e.g., $R^1$ is $-(CH_2)_qC(O)_2X^6$ where $X^6$ is hydrogen, or $R^2$ or $A^1$ contains carboxylic add) wherein the free hydrogen is replaced by $(C_1-C_4)$alkyl, $(C_2-C_{12})$alkanoyloxymethyl, $(C_4-C_9)$1-(alkanoyloxy)ethyl, 1-methyl-1-(alkanoyloxy)-ethyl having from 5 to 10 carbon atoms, alkoxycarbonyl-oxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N (alkoxycarbonyl)aminomethyl having from 3 to 9 carbon atoms, 1-(N-(alkoxycarbonylamino)ethyl having from 4 to 10 carbon atoms, 3-phthalidyl, 4-crotonolactonyl, gamma-butyrolacton-4-yl di-N,N-$(C_1-C_2)$alkylamino$(C_2-C_3)$)alky (such as β-dimethylaminoethyl), carbamoyl-$(C_1-C_2)$alkyl, N,N-di$(C_1-C_2)$-alkylcarbamoyl-$(C_1-C_2)$alkyl and piperidino-, pyrrolidino- or morpholino$(C_2-C_3)$alkyl.

Other exemplary prodrugs release an alcohol of formula I wherein the free hydrogen of the hydroxyl substituent (e.g., $R^1$ contains hydroxyl) is replaced by $(C_1-C_6)$ alkanoyloxymethyl, 1-(($C_1-C_6$)alkanoyloxy)ethyl, 1-methyl]-(($C_1-C_6$)alkanoyl-oxy)ethyl, $(C_1-C_6)$ alkoxycarbonyloxymethyl, N—$(C_1-C_6)$alkoxy-carbonylamino-methyl, succinoyl, $(C_1-C_6)$alkanoyl, α-amino$(C_1-C_4)$alkanoyl, arylacetyl and α-aminoacyl, or α-aminoacyl-α-aminoacyl wherein said α-aminoacyl moieties are independently any of the naturally occurring L-amino adds found in proteins, $P(O)(OH)_2$, $—P(O)(O(C_1-C_6)alkyl)_2$ or glycosyl (the radical resulting from detachment of the hydroxyl of the hemiacetal of a carbohydrate).

Prodrugs of compounds of formula I where a carboxyl group in a carboxylic acid of formula I is replaced by an ester may be prepared by combining the carboxylic acid with the appropriate alkyl halide in the presence of a base such as potassium carbonate in an inert solvent such as DMF at a temperature of about 0° C. to 100° C. for about 1 to about 24 hours. Alternatively, the acid is combined with the appropriate alcohol as solvent in the presence of a catalytic amount of acid such as concentrated sulfuric acid at a temperature of about 20° C. to 120° C., preferably at reflux, for about 1 hour to about 24 hours. Another method is the reaction of the acid in an inert solvent such as THF, with concomitant removal of the water being produced by physical (e.g., Dean Stark trap) or chemical (e.g., molecular sieves) means.

Prodrugs of compounds of formula I where an alcohol function has been derivatized as an ether may be prepared by combining the alcohol with th appropriate alkyl bromide or iodide in the presence of a base such as potassium carbonate in an inert solvent such as DMF at a temperature of about 0° C. to 100° C. for about 1 to about 24 hours. Alkanoylaminomethyl ethers may be obtained by reaction of the alcohol with a bis-(alkanoylamino)methane in the presence of a catalytic amount of acid in an inert solvent such as THF, according to a method described in U.S. Pat. No. 4,997,984. Alternatively, these compounds may be prepared by the methods described by Hoffman et al. in J. Org. Chem. 1994, 59, p. 3530.

Certain of the above defined terms may occur more than once in the above formula and upon such occurrence each term shall be defined independently of the other.

Throughout the specification and appendent claims the following abbreviations are used with the following meanings:

| | |
|---|---|
| BOC | t-butyloxycarbonyl |
| BOP | Benzotriazol-1-yloxytris(dimethylamino) phosphonium hexafluorophosphate |
| CBZ | Benzyloxycarbonyl |
| CDl | N,N'-Carbonyldiimidazole |
| $CH_2Cl_2$ | Methylene chloride |
| $CHCl_3$ | Chloroform |
| DCC | Dicyclohexylcarbodiimide |
| DMF | Dimethylformamide |
| EDC | 1-(3-dimethylaminopropyl)-3-ethylcarbodiimide hydrochloride |
| EtOAc | Ethyl acetate |
| FMOC | 9-Fluorenylmethoxycarbonyl |
| h | hours |
| Hex | Hexane |
| HOAT | 1-Hydroxy-7-azabenzotriazole |

| | -continued |
|---|---|
| HOBT | Hydroxybenzotriazole hydrate |
| HPLC | High pressure liquid chromatography |
| MHz | Megahertz |
| MS | Mass Spectrum |
| NMR | Nuclear Magnetic Resonance |
| PTH | Parathyrold hormone |
| TFA | Trifluoroacetic acid |
| THF | Tetrahydrofuran |
| TLC | Thin layer chromatography |
| TRH | Thyrotropin releasing hormone |
| TROC | 2,2,2-Trichloroethoxycarbonyl |

The compounds utilized in a method of the instant invention all have at least one asymmetric center as noted by the asterisk in the structural formula I, above. Additional asymmetric centers may be present on the molecule depending upon the nature of the various substituents on the molecule. Each such asymmetric center will produce two optical isomers and it is intended that all such optical isomers, as separated, pure or partially purified optical isomers, racemic mixtures or diastereomeric mixtures thereof, be included within the scope of the instant invention. In the case of the asymmetric center represented by the asterisk, it has been found that the absolute stereochemistry of the more active and, thus, more preferred isomer is shown in formula IA. This preferred absolute configuration also applies to formula I.

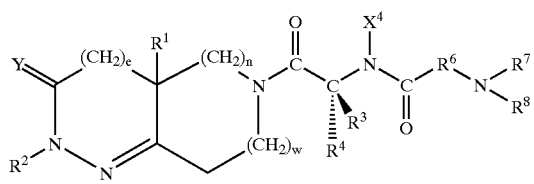

(IA)

With the $R^4$ substituent as hydrogen, the spatial configuration of the asymmetric center corresponds to that in a D-amino acid. In most cases this is also designated an R-configuration although this will vary according to the values of $R^3$ and $R^4$ used in making R- or S-stereochemical assignments.

The compounds of formula I utilized in methods of the instant invention are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, D-tartaric, L-tartaric, malonic, methane sulfonic and the like. In addition, certain compounds containing an acidic function such as a carboxy can be isolated in the form of their inorganic salt in which the counter-ion can be selected from sodium, potassium, lithium, calcium, magnesium and the like, as well as from organic bases.

The pharmaceutically acceptable salts are formed by taking about 1 equivalent of a compound of formula I and contacting it with about 1 equivalent of the appropriate corresponding acid of the salt which is desired. Work-up and isolation of the resulting salt is well-known to those of ordinary skill in the art The present invention includes within its scope pharmaceutical compositions comprising, as an active ingredient an insulin resistance treating amount of at least one of the compounds of formula I in association with a pharmaceutically acceptable carrier. Further, the present invention includes within its scope pharmaceutical compositions comprising, as an active ingredient, at least one alpha-2 adrenergic agonist and at least one of the compounds of formula I in association with a pharmaceutically acceptable carrier. Optionally, the pharmaceutical compositions can further comprise an anabolic agent in addition to at least one of the compounds of formula I or another compound which exhibits a different activity, e.g., an antibiotic growth permittant or with other pharmaceutically active materials wherein the combination enhances efficacy and minimizes side effects.

Assay for Stimulation of GH Release from Rat Pituicytes

Compounds that have the ability to stimulate GH secretion from cultured rat pituitary cells are identified using the following protocol. This test is also useful for comparison to standards to determine dosage levels. Cells are isolated from pituitaries of 6 week old male Wistar rats. Following decapitation, the anterior pituitary lobes are removed into cold, sterile Hank's balanced salt solution without calcium or magnesium (HBSS). Tissues are finely minced, then subjected to two cycles of mechanically assisted enzymatic dispersion using 10 U/mL bacterial protease (EC 3.4.24.4, Sigma P6141, St. Louis, Mo.) in HBSS. The tissue-enzyme mixture is stirred in a spinner flask at 30 rpm in a 5% $CO_2$ atmosphere at about 37° C. for about 30 min., with manual trituration after about 15 min. and about 30 min. using a 10-mL pipet. This mixture is centrifuged at 200×g for about 5 min. Horse serum (35% final concentration) is added to the supernatant to neutralize excess protease. The pellet is resuspended in fresh protease (10 U/mL), stirred for about 30 min. more under the previous conditions, and manually triturated, ultimately through a 23-gauge needle. Again, horse serum (35% final concentration) is added, then the cells from both digests are combined, pelleted (200×g for about 15 min.), resuspended in culture medium (Dulbecco's Modified Eagle Medium (DMEM) supplemented with 4.5 g/L glucose, 10% horse serum, 2.5% fetal bovine serum, 1% nonessential amino acids, 100 U/mL nystatin and 50 mg/mL gentamycin sulfate, Gibco, Grand Island, N.Y.) and counted. Cells are plated at $6.04.5\times10^4$ cells per $cm^2$ in 48-well Costar™ (Cambridge, Mass.) dishes and cultured for 3–4 days in culture medium.

Just prior to GH secretion assay, culture wells are rinsed twice with release medium, then equilibrated for about 30 minutes in release medium (D-MEM buffered with 25 mM Hepes, pH 7.4 and containing 0.5% bovine serum albumin at 37° C.). Test compounds are dissolved in DMSO, then diluted into pre-warmed release medium. Assays are run in quadruplicate. The assay is initiated by adding 0.5 mL of release medium (with vehicle or test compound) to each culture well. Incubation is carried out at about 37° C. for about 15 minutes, then terminated by removal of the release medium, which is centrifuged at 2000×g for about 15 minutes to remove cellular material. Rat growth hormone concentrations in the supernatants are determined by a standard radioimmunoassay protocol described below.

Measurement of Rat Growth Hormone

Rat growth hormone concentrations were determined by double antibody radioimmunoassay using a rat growth hormone reference preparation (NIDDK-rGH-RP-2) and rat growth hormone antiserum raised in monkey (NIDDK-anti-rGH-S-5) obtained from Dr. A. Parlow (Harbor-UCLA Medical Center, Torrence, Calif.). Additional rat growth hormone (1.5 U/mg, #G2414, Scripps Labs, San Diego, Calif.) is iodinated to a specific activity of approximately 30 $\mu$Ci/$\mu$g by the chloramine T method for use as tracer. Immune complexes are obtained by adding goat antiserum to monkey IgG (ICN/Cappel, Aurora, Ohio) plus polyethylene glycol, MW 10,000–20,000 to a final concentration of 4.3%; recovery is accomplished by centrifugation. This assay has a working range of 0.08–2.5 $\mu$g rat growth hormone per tube above basal levels.

Assay for Exogenously-Stimulated Growth Hormone Release in the Rat after Intravenous Administration of Test Compounds Twenty-one day old female Sprague-Dawley rats (Charles River Laboratory, Wilmington, Mass.) are allowed to acclimate to local vivarium conditions (24° C., 12 hr light, 12 hr dark cycle) for approximately 1 week before compound testing. All rats are allowed access to water and a pelleted commercial diet (Agway Country Food, Syracuse N.Y.) ad libitum. The experiments are conducted in accordance with the NIH Guide for the Care and Use of Laboratory Animals.

On the day of the experiment, test compounds are dissolved in vehicle containing 1% ethanol, 1 mM acetic acid and 0.1% bovine serum albumin in saline. Each test is conducted in three rats. Rats are weighed and anesthetized via intraperitoneal injection of sodium pentobarbital (Nembutol®, 50 mg/kg body weight). Fourteen minutes after anesthetic administration, a blood sample is taken by nicking the tip of the tail and allowing the blood to drip into a microcentrifuge tube (baseline blood sample, approximately 100 $\mu$l). Fifteen minutes after anesthetic administration, test compound is delivered by intravenous injection into the tail vein, with a total injection volume of 1 mL/kg body weight. Additional blood samples are taken from the tail at 5, 10 and 15 minutes after compound administration. Blood samples are kept on ice until serum separation by centrifugation (1430×g for 10 minutes at 10° C.). Serum is stored at 60° C. until serum growth hormone determination by radioimmunoassay as described above.

Assessment of Exogenously-Stimulated Growth Hormone Release in the Dog after Oral Administration On the day of dosing, the test compound is weighed out for the appropriate dose and dissolved in water. Doses are delivered at a volume of 0.5–3 mL/kg by gavage to 24 dogs for each dosing regimen. Blood samples (5 mL) are collected from the jugular vein by direct vena puncture pre-dose and at 0.17, 0.33, 0.5, 0.75, 1, 2, 4, 6, 8 and 24 hours post dose using 5 mL vacutainers containing lithium heparin. The prepared plasma is stored at –20° C. until analysis.

Measurement of Canine Growth Hormone

Canine growth hormone concentrations are determined by a standard radioimmunoassay protocol using canine growth hormone (antigen for iodination and reference preparation AFP-1983B) and canine growth hormone antiserum raised in monkey (AFP-21452578) obtained from Dr. A. Parlow (Harbor-UCLA Medical Center, Torrence, Calif.). Tracer is produced by chloramine T-iodination of canine growth hormone to a specific activity of 20–40 $\mu$Ci/$\mu$g. Immune complexes are obtained by adding goat antiserum to monkey IgG (ICN/Cappel, Aurora, Ohio) plus polyethylene glycol, MW 10,000–20,000 to a final concentration of 4.3%; recovery is accomplished by centrifugation. This assay has a working range of 0.08–2.5 $\mu$g canine GH/tube.

Assessment of Canine Growth Hormone and Insulin-Like Growth Factor-1 Levels in the Dog after Chronic Oral Administration The dogs receive test compound daily for either 7 or 14 days. Each day of dosing, the test compound is weighed out for the appropriate dose and dissolved in water. Doses are delivered at a volume of 0.5–3 ml/kg by gavage to 5 dogs for each dosing regimen. Blood samples are collected at days 0, 3, 7, 10 and 14. Blood samples (5 ml) are obtained by direct venipuncture of the jugular vein at pre-dose, 0.17, 0.33, 0.5, 0.754, 1, 2, 3, 6, 8, 12 and 24 hours post administration on days 0, 7 and 14 using 5 ml vacutainers containing lithium heparin. In addition, blood is drawn pre-dose and 8 hours on days 3 and 10. The prepared plasma is stored at –20° C. until analysis.

Female Rat Study

This study evaluates the effect of chronic treatment with a GHRP mim tic on weight, body composition and non-fasting plasma concentrations of glucose, insulin, lactate and lipids in estrogen-deficient and estrogen-replete female rats. Acute responsiveness of serum GH levels to i.v. administration of the GH releasing agent was assessed on the last day of dosing. Body weight was monitored weekly throughout the treatment period; additionally, body composition and plasma levels of glucose, insulin, lactate, cholesterol and triglycerides were assessed at the end of treatment.

Virgin female Sprague-Dawley rats were obtained from Charles River Laboratories (Wilmington, Mass.) and underwent bilateral ovariectomy (Ovx) or sham-surgery (Sham) at approximately 12 weeks of age. For sham surgeries, ovaries were exteriorized and replaced into the abdominal cavity. Following surgery the rats were housed individually in 20 cm×32 cm×20 cm cages under standard vivarium conditions (about 24° C. with about 12 hours light/12 hours dark cycle). All rats were allowed free access to water and a pelleted commercial diet (Agway ProLab 3000, Agway Country Food, Inc., Syracuse, N.Y.). The experiment was conducted in accordance with NIH Guidelines for the Care and Use of Laboratory Animals.

Approximately seven months post-surgery, Sham and Ovx rats were weighed and randomly assigned to groups. Rats were dosed daily by oral gavage with 1 mL of either vehicle (1% ethanol in distilled-deionized water), 0.5 mg/kg or 5 mg/kg of a growth hormone releasing agent for 90 days. Rats were weighed at weekly intervals throughout the study. Twenty-four hours after the last oral dose, the acute response of serum growth hormone (GH) to test agent was assessed by the following procedure. Rats were anesthetized with sodium pentobarbital 50 mg/kg. Anesthetized rats were weighed and a baseline blood sample (~100 $\mu$l) was collected from the tail vein. Test agent (growth hormone releasing agent or vehicle) was then administered intravenously via the tail vein in 1 mL. Approximately ten minutes after injection, a second 100 $\mu$l blood sample was collected from the tail. Blood was allowed to dot at about 4° C., then centrifuged at 2000×g for about 10 minutes. Serum was stored at about –70° C. Serum growth hormone concentrations were determined by radioimmunoassay as previously described. Following this procedure, each anesthetized rat underwent whole body scanning by dual-energy X-ray absorptometry (DEXA, Hologic QDR 1000/W, Waltham Mass.). A final blood sample was collected by cardiac puncture into heparinized tubes. Plasma was separated by centrifugation and stored frozen as described above.

Plasma insulin is determined by radioimmunoassay using a kit from Binax Corp. (Portland, Me.). The interassay coefficient of variation is $\leq 10\%$. Plasma triglycerides, total cholesterol, glucose and lactate levels are measured using Abbott VP™ and VP Super System® Autoanalyzer (Abbott Laboratories, Irving, Tex.), using the A-Gent™ Triglycerides, Cholesterol and Glucose Test reagent systems, and a lactate kit from Sigma, respectively. The plasma insulin, triglycerides, total cholesterol and lactate lowering activity of a growth hormone releasing peptide (GHRP) or GHRP mimetic such as a compound of formula I, are determined by statistical analysis (unpaired t-test) with the vehicle-treated control group.

The compounds of formula I utilized in a method of this invention can be administered by oral, parenteral (e.g., intramuscular, intraperitoneal, intravenous or subcutaneous injection, or implant), nasal, vaginal, rectal, sublingual, or topical routes of administration and can be formulated with pharmaceutically acceptable carriers to provide dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 100 mg/kg of body weight daily are administered to humans and other animals, e.g., mammals, to obtain effective release of growth hormone.

A preferred dosage range in humans is 0.01 to 5.0 mg/kg of body weight daily which can be administered as a single dose or divided into multiple doses.

A preferred dosage range in animals other than humans is 0.01 to 10.0 mg/kg of body weight daily which can be administered as a single dose or divided into multiple doses. A more preferred dosage range in animals other than humans is 0.1 to 5 mg/kg of body weight daily which can be administered as a single dose or divided into multiple doses.

The preparation of the compounds of formula I utilized in a method of the present invention can be carried out in sequential or convergent synthetic routes. Syntheses detailing the preparation of the compounds of formula I in a sequential manner are presented in the reaction schemes shown hereinbelow.

Many protected amino acid derivatives are commercially available, where the protecting groups Prt, $Z^{100}$ and $Z^{200}$ are, for example, BOC, CBZ, benzyl, ethoxycarbonyl groups, $CF_3C(O)$—, FMOC, TROC, trityl or tosyl. Other protected amino acid derivatives can be prepared by literature methods. Some 3-oxo-2-carboxyl pyrrolidines, and 4-oxo-3-carboxyl piperidines are commercially available, and many other related pyrrolidines and 4-substituted piperidines are known in the literature.

Many of the schemes illustrated below describe compounds which contain protecting groups Prt, $Z^{100}$ or $Z^{200}$. Benzyloxycarbonyl groups can be removed by a number of methods including, catalytic hydrogenation with hydrogen in the presence of a palladium or platinum catalyst in a protic solvent such as methanol. Preferred catalysts are palladium hydroxide on carbon or palladium on carbon. Hydrogen pressures from 1–1000 psi may be employed; pressures from 10 to 70 psi are preferred. Alternatively, the benzyloxycarbonyl group can be removed by transfer hydrogenation.

Removal of BOC protecting groups can be carried out using a strong acid such as trifluoroacetic acid or hydrochloric acid with or without the presence of a cosolvent such as dichloromethane, ethyl acetate, ether or methanol at a temperature of about −30 to 70° C., preferably about −5 to about 35° C.

Benzyl esters of amines can be removed by a number of methods including, catalytic hydrogenation with hydrogen in the presence of a palladium catalyst in a protic solvent such as methanol. Hydrogen pressures from 1–1000 psi may be employed; pressures from 10 to 70 psi are preferred. The addition and removal of these and other protecting groups are discussed by T. Greene in Protective. Groups in Organic Synthesis, John Wiley & Sons, New York, 1981.

SCHEME 1

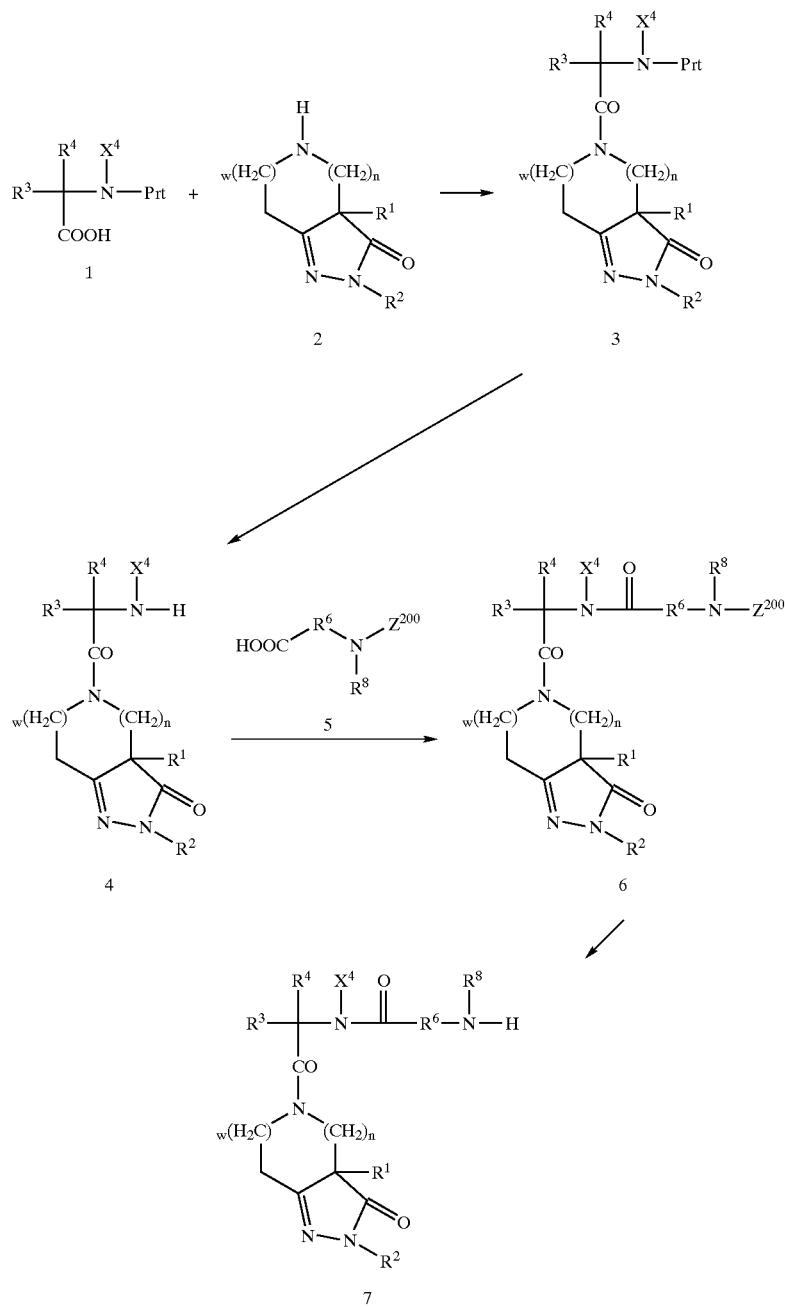

SCHEME 1: The protected amino acid derivatives I are in many cases commercially available, where the protecting group Prt is, for example, BOC, FMOC or CBZ groups. Other amino acids can be prepared by literature methods.

As illustrated in Scheme 1, coupling of amines of formula 2 with protected amino acids of formula 1, where Prt is a suitable protecting group, is conveniently carried out in an inert solvent such as dichloromethane or DMF by a coupling reagent such as EDC or DCC in the presence of HOBT or HOAT. In the case where the amine is present as the hydrochloride salt, it is preferable to add one or two equivalents of a suitable base such as triethylamine to the reaction mixture. Alternatively, the coupling can be effected with a coupling reagent such as BOP in an inert solvent such as methanol. Such coupling reactions are generally conducted at temperatures of about −30° to about 80° C., preferably −10° to about 25° C. For a discussion of other conditions used for coupling peptides see Houben-Weyl, Vol. XV, part 1, E. Wunsch, Ed., George Theime Verlag, 1974, Stuttgart. Separation of unwanted side products and purification of intermediates is achieved by chromatography on silica gel, employing flash chromatography (W. C. Still, M. Kahn and A. Mitra, J. Org. Chem. 43 2923 1978), by crystallization or by trituration.

Transformation of the compound of formula 3 into intermediates of formula 4 can be carried out by removal of the protecting group Prt as described above. Coupling of intermediates of formula 4 to amino acids of formula 5 can be effected as described above to give intermediates of formula 6. Deprotection of the amine 6 affords compounds of formula 7.

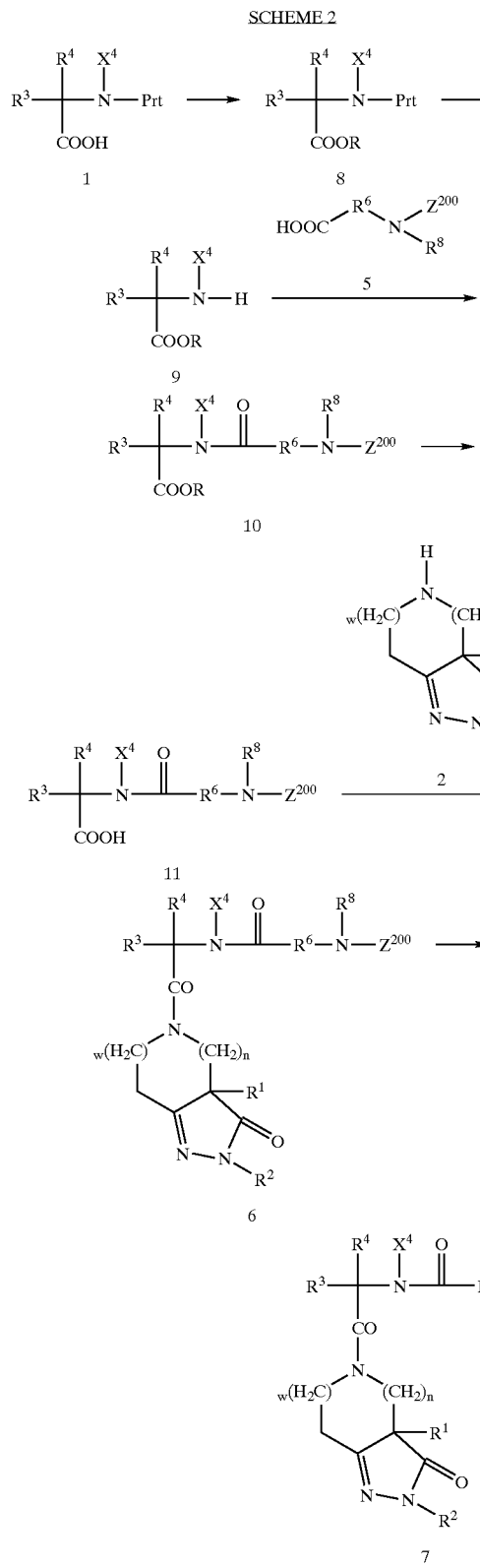

SCHEME 2: Alternatively, compounds of formula 7 can be prepared by a convergent route as shown in Scheme 2. Intermediate esters of formula 8 can be prepared by treating amino acids 1, where Prt is a suitable protecting group, with a base such as potassium carbonate followed by an alkyl halide such as iodomethane. In a suitable solvent such as DMF. Deprotection of the amine transforms 8 into 9. Alternatively, many amino acids of formula 9 are commercially available. Intermediate 10 is generated by coupling 9 to amino acid 5. The ester of intermediate 10 can be converted to intermediate acid 11 by a number of methods known in the art; for example, methyl and ethyl esters can be hydrolyzed with lithium hydroxide in a protic solvent such as aqueous methanol or aqueous THF at a temperature of about −20° to 120° C., preferably about 0° to 50° C. In addition, removal of a benzyl group can be accomplished by a number of reductive methods including hydrogenation in the presence of platinum or palladium catalyst in a protic solvent such as methanol. Acid 11 can then be coupled to amine 2 to give intermediates of formula 6. Transformation of 6 to 7 can be achieved by removal of the protecting group $Z^{200}$.

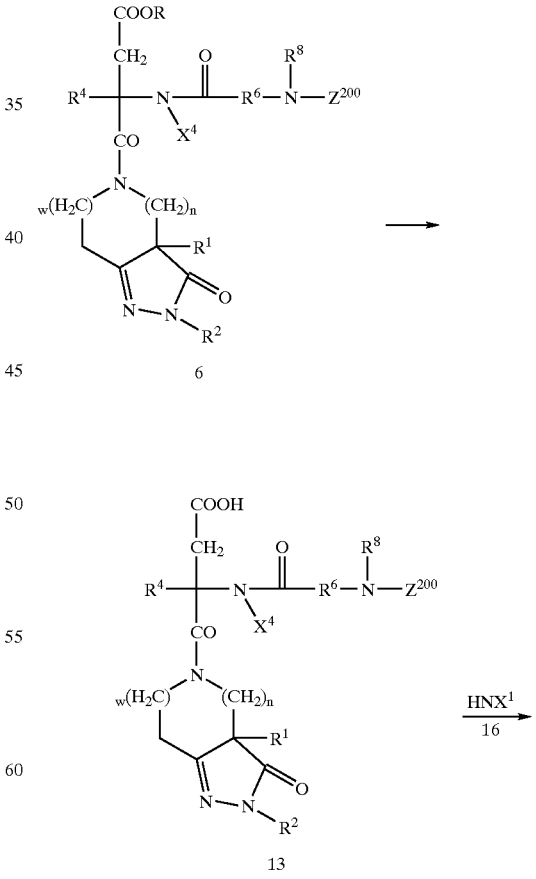

-continued

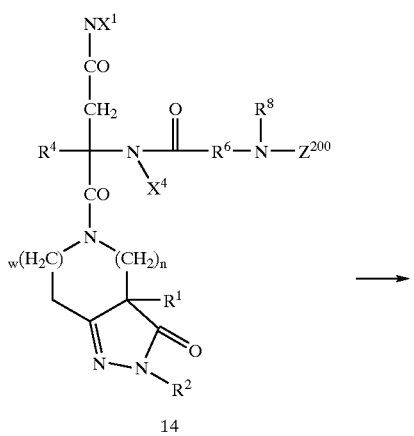

14

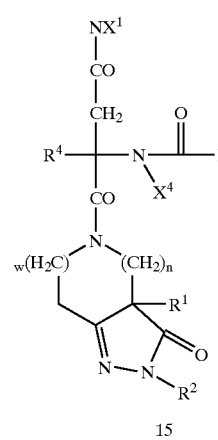

15

SCHEME 3: The esters of formula 6 can be converted to intermediate acids of formula 13 by a number of methods known in the art; for example, methyl and ethyl esthers can be hydorlyzed with lithium hydroxide in a protic solvent such as aqueous methanol or aqueous THF at a temperature of about −20° to 130° C., preferably about 0° to 50° C. In addition, removal of a benzyl group can be accomplished by a number of reductive methods including hydorgenation in the presence of platinum or palladium catalyst in a protic solvent such as methanol. Coupling the acid 13 to amine 16 generates the intermediates of formula 14. Transformation of 14 to 15 can be achieved by removal of the protecting group $Z^{200}$.

SCHEME 4

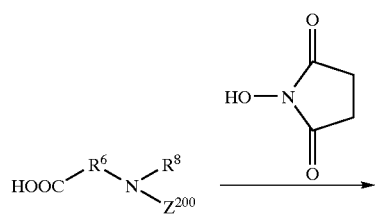

5

-continued

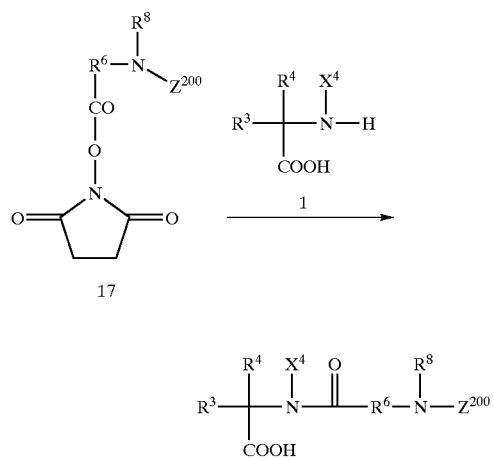

17

11

SCHEME 4: Esters of formula 17 can be prepared by treating an acid of formula 5 with hydroxysuccinimide in the presence of a coupling agent such as EDC in an inert solvent such as methylene chloride as illustrated in Scheme 4. Treatment of an ester 17 with an amino acid of formula 1 in a solvent such as dioxane, THF or DMF in the presence of a base such as diisopropylethylamine produces 11.

SCHEME 5

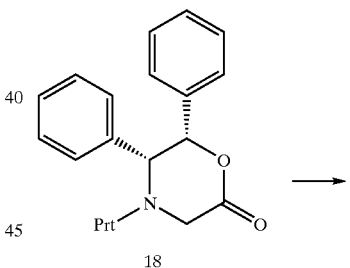

18

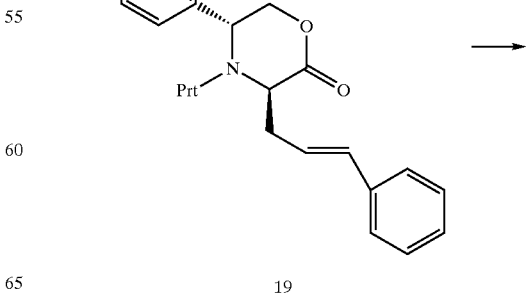

19

-continued

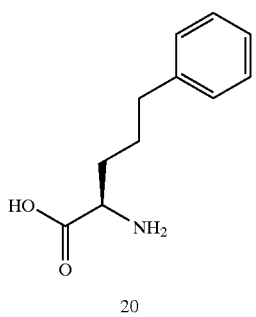

20

SCHEME 5: As illustrated in Scheme 5, alkylation of the diphenyloxazinone of formula 18 with cinnamyl bromide in the presence of sodium bis(trimethylsilyl)amide generates 19 which is then converted to the desired (D)-2-amino-5-phenylpentanoic acid 20 by removing the protecting group (Prt) and hydrogenation over a PdCl$_2$ catalyst SCHEME 6: treatment of an ester of formula 21 with a base such as sodium hydride in a solvent such as DMF followed by an alkyl halide 22 generates a compound of formula 23 as illustrated in Scheme 6. Treating a compound of formula 23 with a hydrazine of formula 24 such as hydrazine or methyl-hydrazin in a solvent such as refluxing ethanol, followed by concentration and heating the residue in toluene at temperatures at or near reflux results in a compound of formula 25. Alternatively, 23 can be treated with a salt of a hydrazine in the presence of sodium acetate in refluxing ethanol to give 25. Deprotection of the amine generates a compound of formula 28. Thioamides of formula 26 can be formed by treating 25 with Lawesson's reagent in refluxing toluene or benzene. Removal of the protecting group transforms 26 into 27.

SCHEME 6

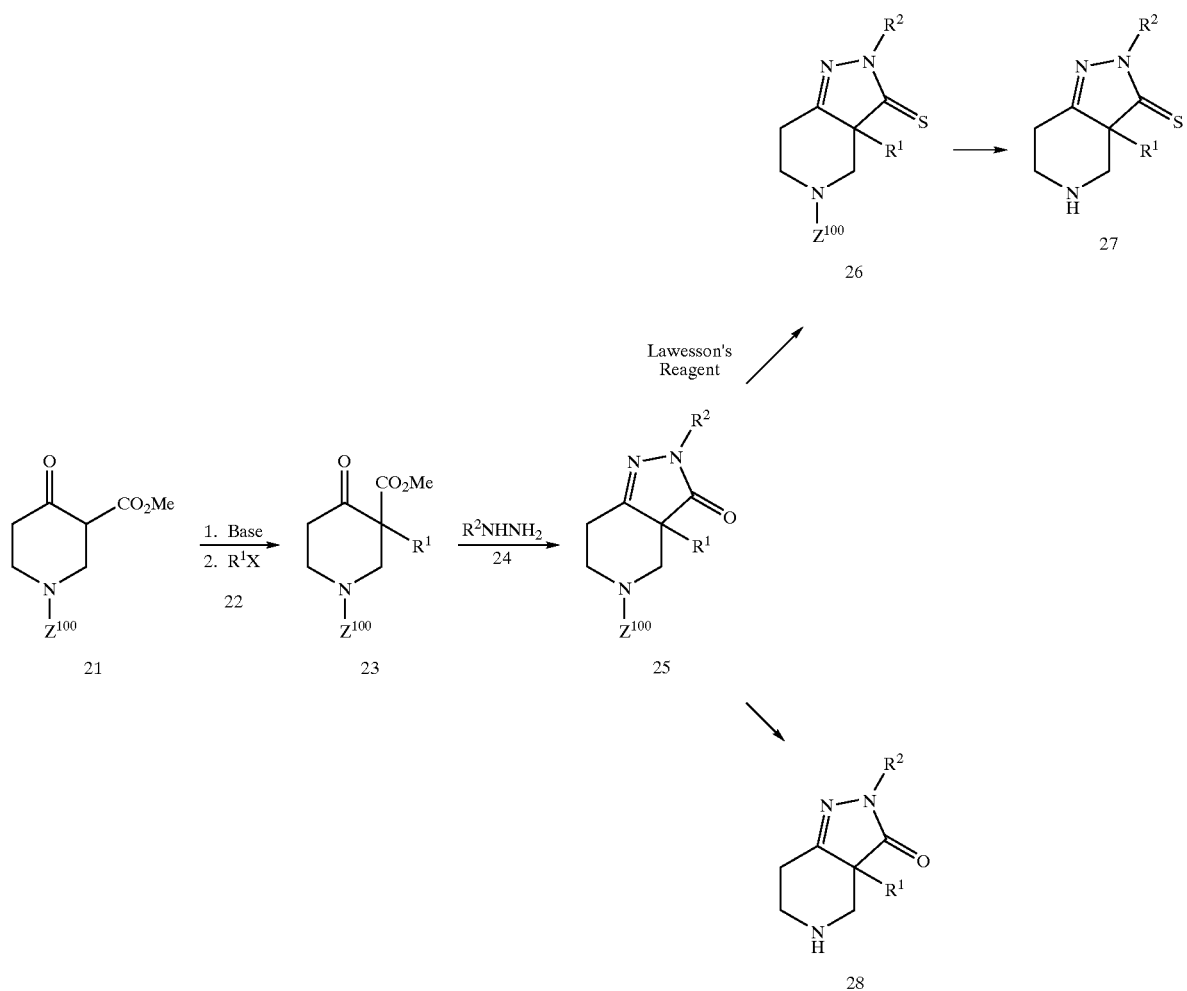

SCHEME 7

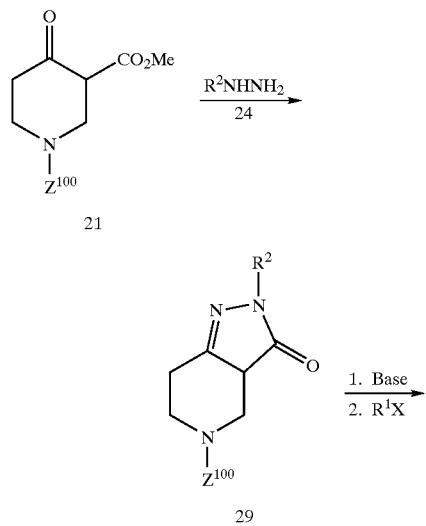

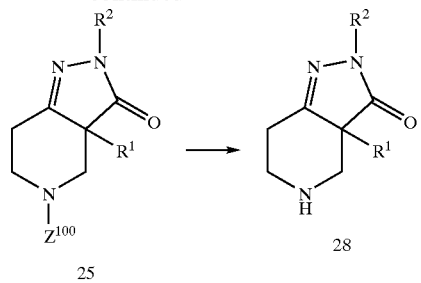

SCHEME 7: Treatment of a compound of formula 21 with a hydrazine of formula 24 in a solvent such as refluxing ethanol, followed by concentration and heating the residue in toluene at temperatures at or near reflux results in compounds of formula 29. Alternatively, 21 can be treated with a salt of a hydrazine in the presence of sodium acetate in refluxing ethanol to give 29. The amide of formula 29 can be treated with a base such as sodium hydride in a solvent such as DMF followed by an alkyl halide to give 25. Deprotection of the amine generates a compound of formula 28.

SCHEME 8

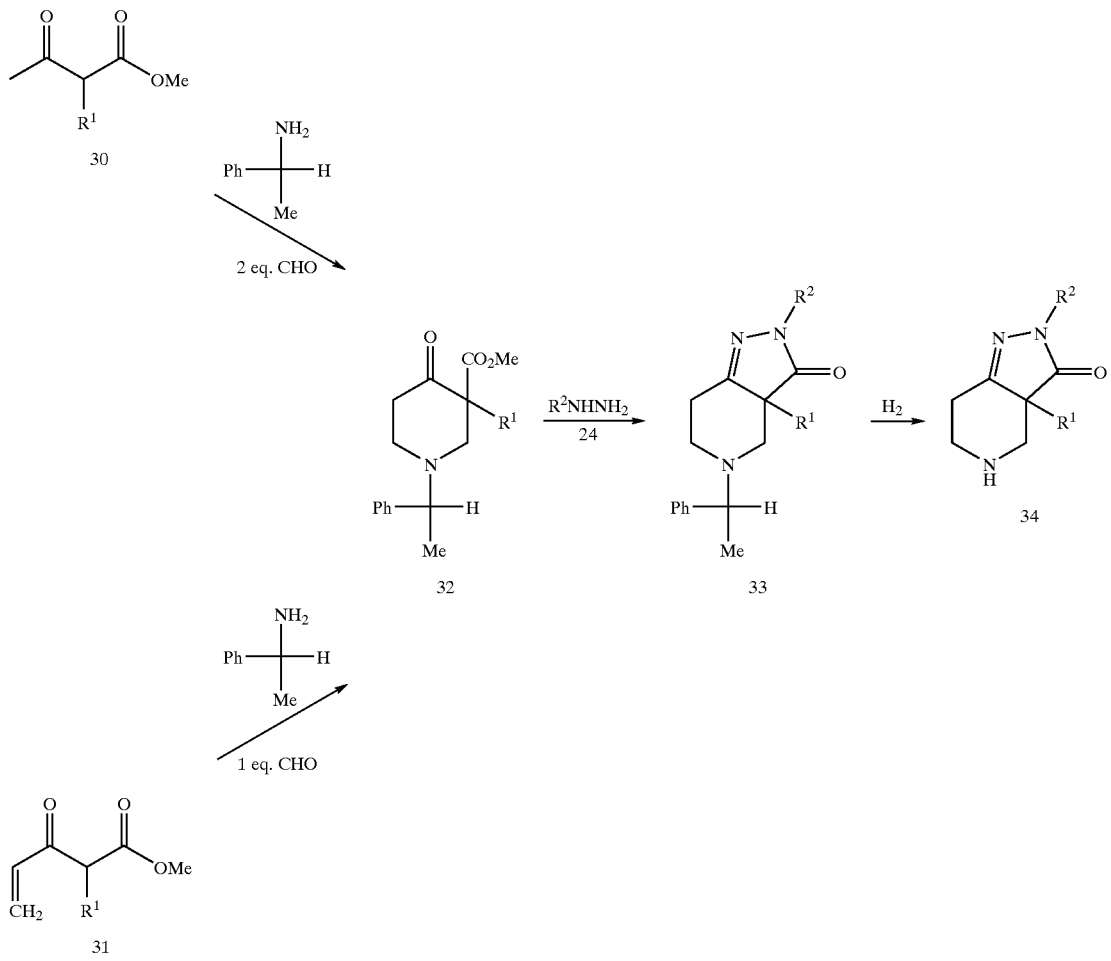

SCHEME 8: Reaction of a ketoester of formula 30 with a chiral amine such as alpha-methylbenzylamine with a suitable aldehyde such as formaldehyde, or reaction of a vinyl ketoester of formula 31 with a chiral amine such as alpha-methylbenzylamine with a suitable aldehyde such as formaldehyde, affords a compound of formula 32 via a double Mannich reaction. Reaction of 32 with a hydrazine generates a chiral compound of formula 33. Deprotection of the nitrogen with hydrogen and a suitable catalyst such as palladium affords compounds of formula 34.

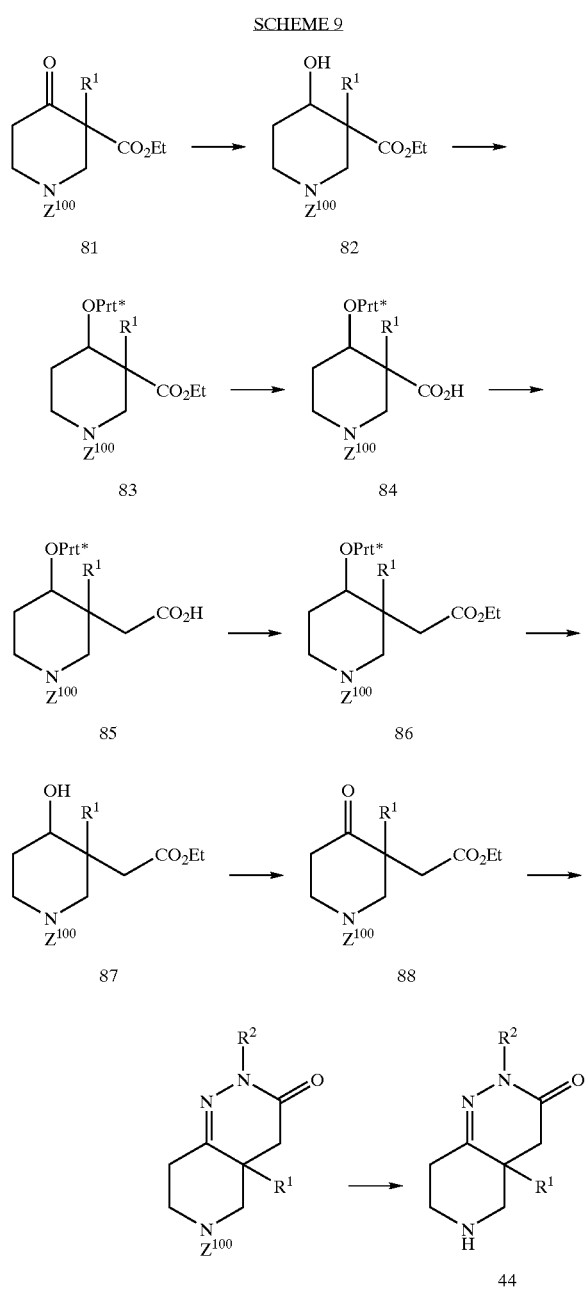

SCHEME 9: Treatment of a compound of formula 81 with a reducing agent such as sodium borohydrid and protection of the nitrogen affords a compound of formula 82. Protection of the alcohol affords 83. Saponification of the ester affords a compound of formula 84. Reaction of 84 with thionyl chloride followed by treatment with diazomethane affords the homologated acid of formula 85. Esterification of 85 affords a compound of formula 86, which is O-deprotected to give 87. Oxidation of 87 affords a ketone of formula 88. Reaction of 88 with a hydrazine, followed by nitrogen deprotection affords a compound of formula 44.

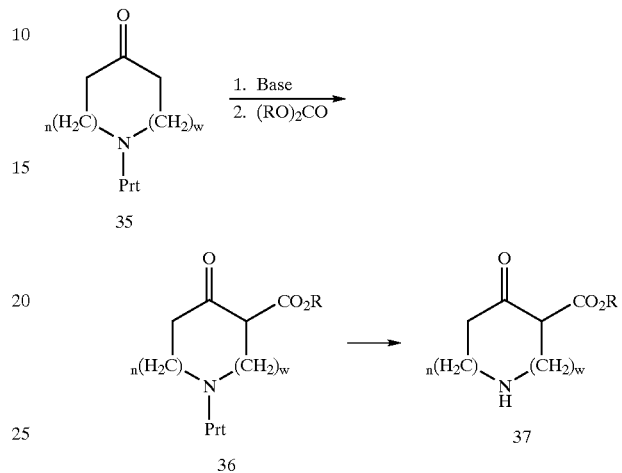

SCHEME 10: Treatment of a compound of formula 35 with a base such as sodium hydride in a solvent such as DMF followed by treatment with diethylcarbonate generates the ethyl ester of compound 36. Deprotection of the amine transforms 36 into 37.

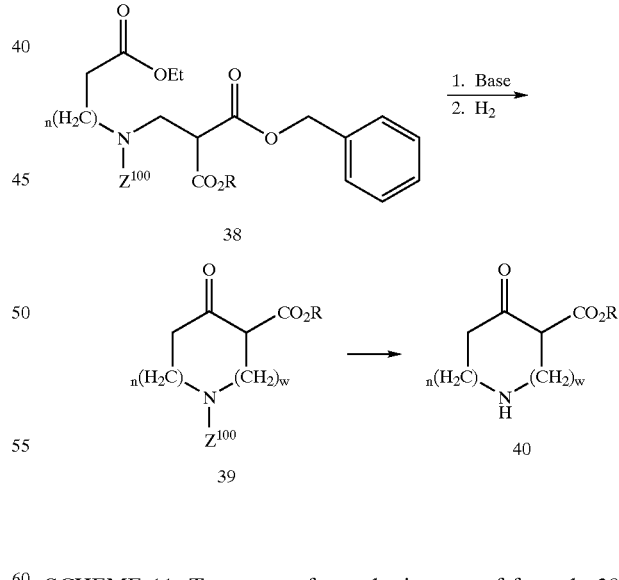

SCHEME 11: Treatment of a malonic ester of formula 38 with base such as sodium hydride in a solvent such as DMF and subsequent hydrogenolysis of the benzyl group with hydrogen and a catalyst such as palladium in a suitable solvent such as methanol produces the ester of formula 39. Deprotection of the amine generates compounds of formula 40.

SCHEME 12

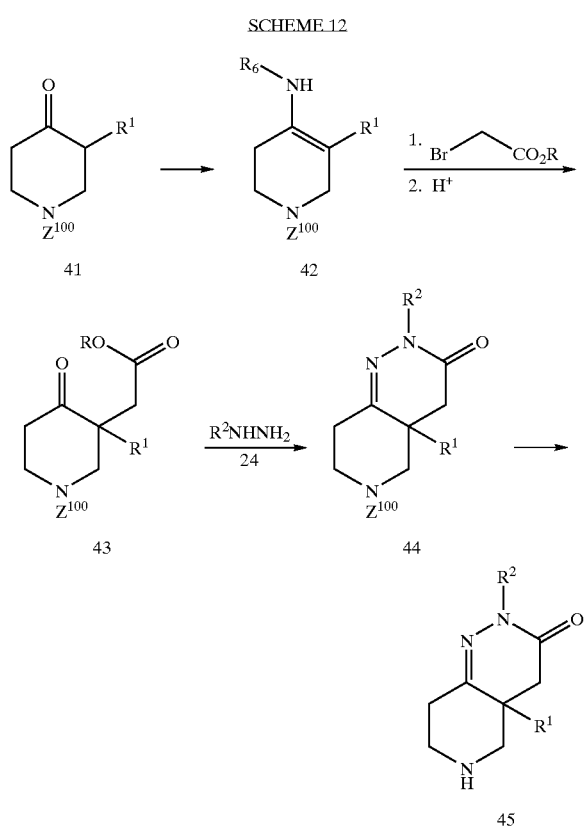

SCHEME 12: Treatment of a ketone of formula 41 with a secondary amine such as piperidine in a suitable solvent such as benzene with removal of water affords an enamine of formula 42. Alkylation of the enamine with an alpha-haloester such as ethylbromoacetate in a suitable solvent such as benzene or THF using a suitable base such as LDA or $NaN(SiMe_3)_2$ affords a ketoester of formula 43. Reaction with a hydrazine of formula 24 affords the compound of formula 44. Deprotection of the nitrogen affords compounds of formula 45.

SCHEME 13

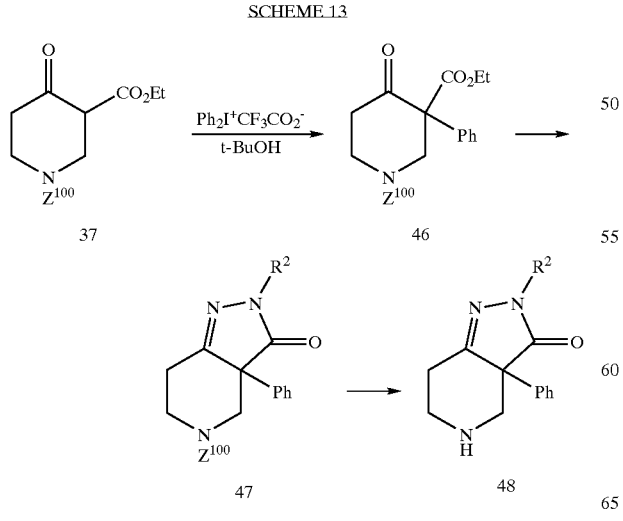

Scheme 13: Treatment of a ketoester of formula 37 with an iodonium salt such as diphenyliodonium trifluoroacetate in a suitable solvent such as t-butanol generates a ketoester of formula 46. Reaction of 46 with a hydrazine generates a compound of formula 47. Deprotection of the nitrogen affords compounds of formula 48, see Synthesis, (9), 1984 p. 709 for a detailed description.

SCHEME 14

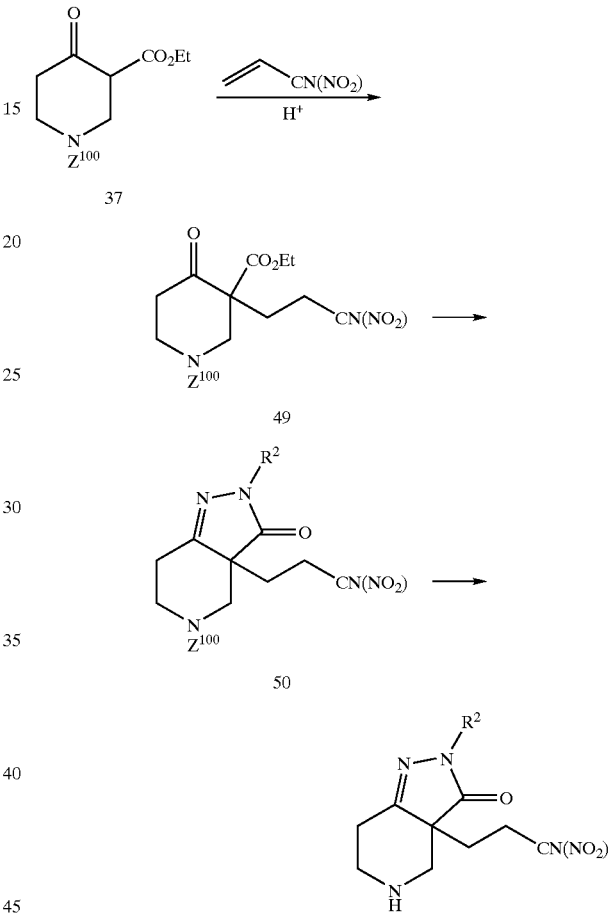

SCHEME 14: Treatment of a ketoester of formula 37 with an olefin such as acrylonitrile generates a ketoester of formula 49. Reaction of 49 with a hydrazine generates a compound of formula 50. Deprotection of the nitrogen affords compounds of formula 51.

SCHEME 15

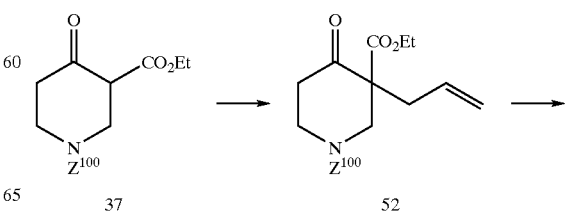

formula 56 with an isocyanate or carbamate affords a urea of formula 57. Deprotection of the nitrogen affords compounds of formula 58.

SCHEME 16

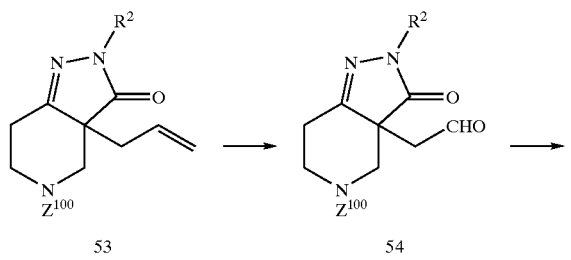

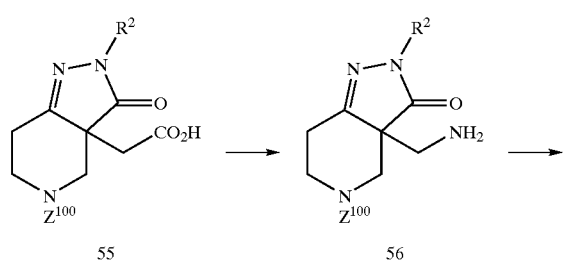

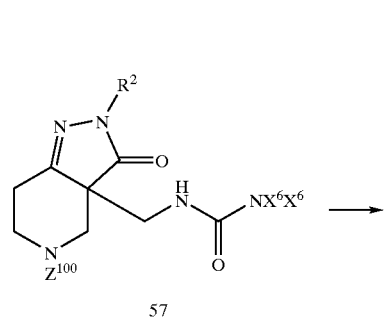

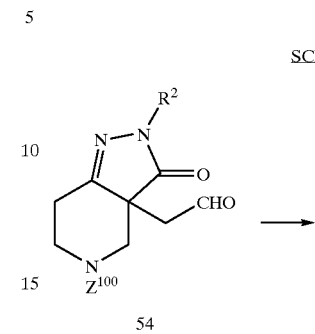

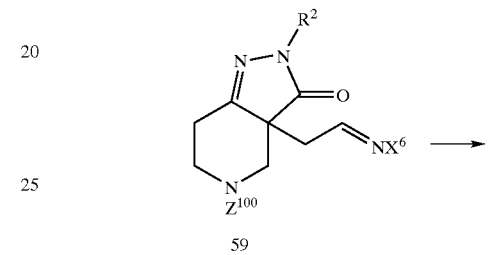

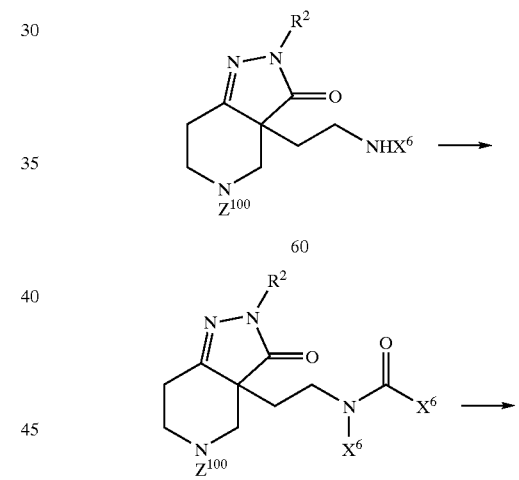

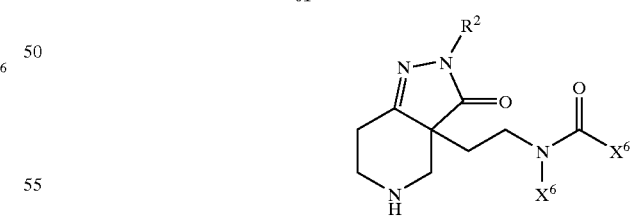

SCHEME 15: Treatment of a ketoester of formula 37 with allyl bromide and a suitable base such as sodium hydride in a suitable solvent such as DMF affords a ketoester of formula 52. Reaction of 52 with a hydrazine generates a compound of formula 53. Ozonolysis of 53 in a suitable solvent such as methylene chloride followed by treatment with a reducing agent such as dimethylsulfide affords an aldehyde of formula 54. Oxidation of 54 affords a carboxylic acid of formula 55. Curtius rearrangement of 55, followed by hydrolysis of the intermediate isocyanate affords a primary amine of formula 56. Treatment of a compound of SCHEME 16: Treatment of a compound of formula 54 with a primary amine affords an imine of formula 59. Reduction of a compound of formula 59 affords a compound of formula 60. Treatment of a compound of formula 60 with an acylating agent affords a compound of formula 61. Deprotection of the nitrogen affords compounds of formula.

SCHEME 17

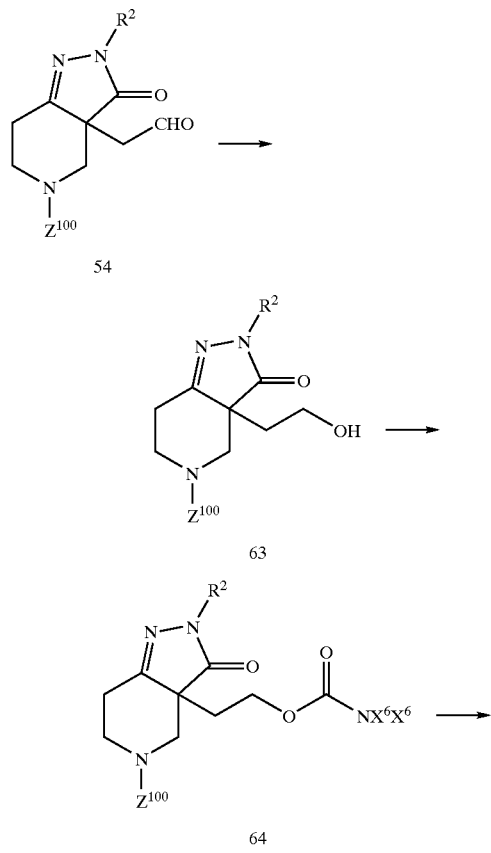

SCHEME 17: Treatment of a compound of formula 54 with a reducing agent such as sodium borohydride affords a compound of formula 63. Reaction of 63 with an acylating agent such as an isocyanate or carbamate affords compounds of formula 64. Deprotection of the nitrogen affords compounds of formula 65.

SCHEME 18

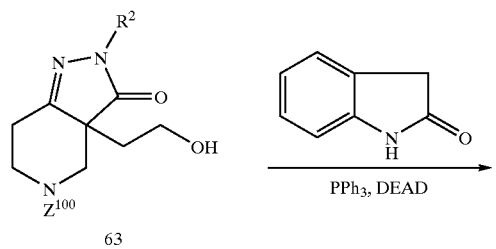

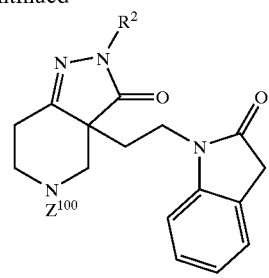

SCHEME 18: Treatment of a compound of formula 63 with a phosphine such as triphenyl phosphine and an azo compound such as diethylazodicarboxylate and an oxindole affords a compound of formula 66. Deprotection of the nitrogen affords the compound of formula 67.

SCHEME 19

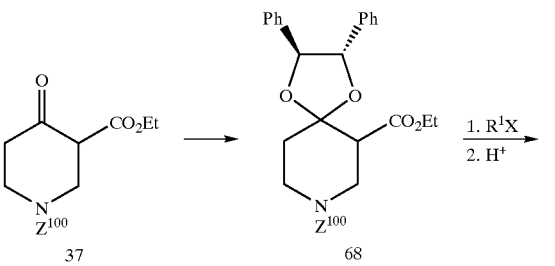

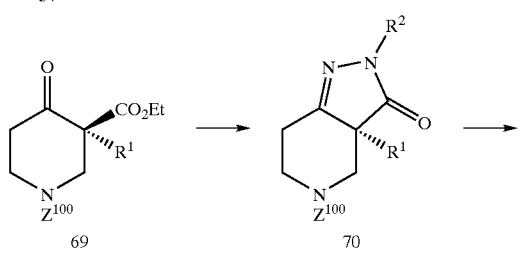

SCHEME 19: Treatment of a ketoester of formula 37 with a chiral diol and acid catalyst with removal of water in a suitable solvent such as benzene affords a chiral ketal of formula 68. Alkylation of 68 with an alkyl halide in the presence of a base such as LDA followed by acid-catalyzed hydrolysis of the ketal affords chiral ketoesters of formula 69. Reaction of 69 with a hydrazine generates chiral compounds of formula 70. D protection of the nitrogen affords compounds of formula 71.

SCHEME 20

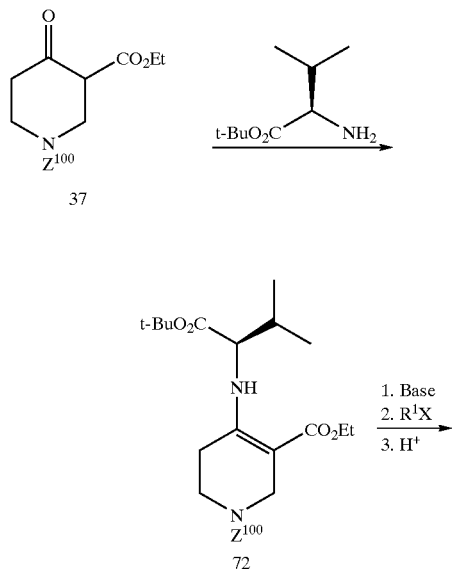

SCHEME 21

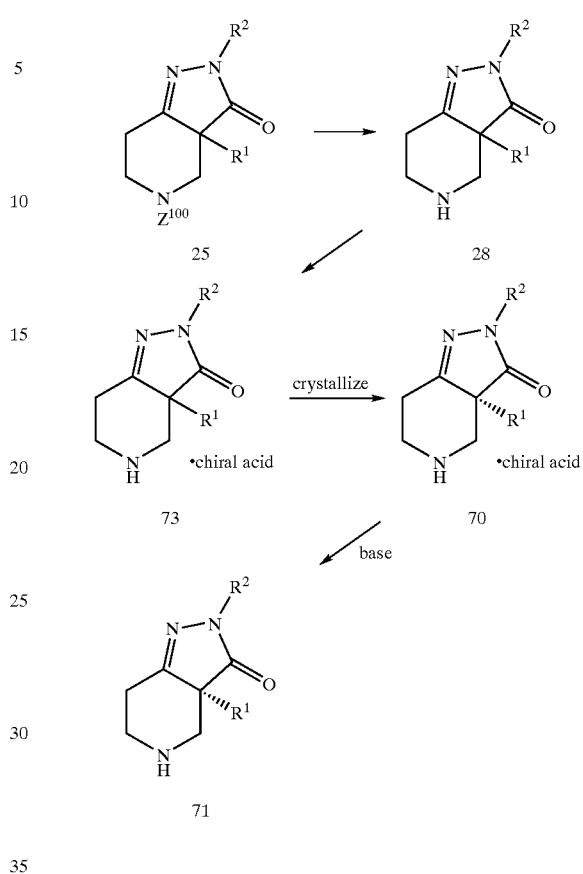

SCHEME 21: Deprotection of the nitrogen of 25 affords compounds of formula 28. Salt formation of 28 with a chiral add affords a mixture of diastereomeric salts of formula 73. Crystallization of the diastereomeric salts affords the acid salt of chiral compounds of formula 70. Decomposition of the salt 70 with base liberates chiral compounds of formula 71.

SCHEME 22

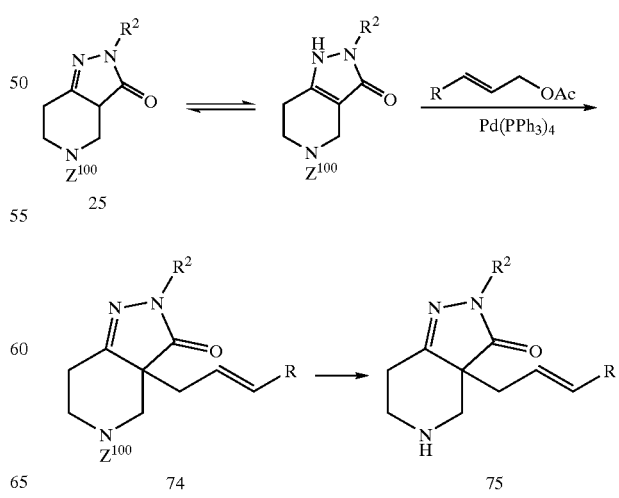

SCHEME 20: Treatment of a ketoester of formula 37 with a chiral amino add ester such as valine t-butyl ester affords a chiral enamine of formula 72. Alkylation of 72 with an alkyl halide in the presence of a base such as LDA followed by add-catalyzed hydrolysis of the enamine affords chiral ketoesters of formula 69. Reaction of 69 with a hydrazine generates chiral compounds of formula 70. Deprotection of the nitrogen affords compounds of formula 71.

SCHEME 22: Alkylation of compounds of formula 25 with an allylic acetate in the presence of a suitable catalyst such as palladium tetrakis(triphenylphosphine) affords compounds of formula 74. Deprotection of the nitrogen affords compounds of formula 75, see Tetrahedron (50) p. 515, 1994 for a detailed discussion.

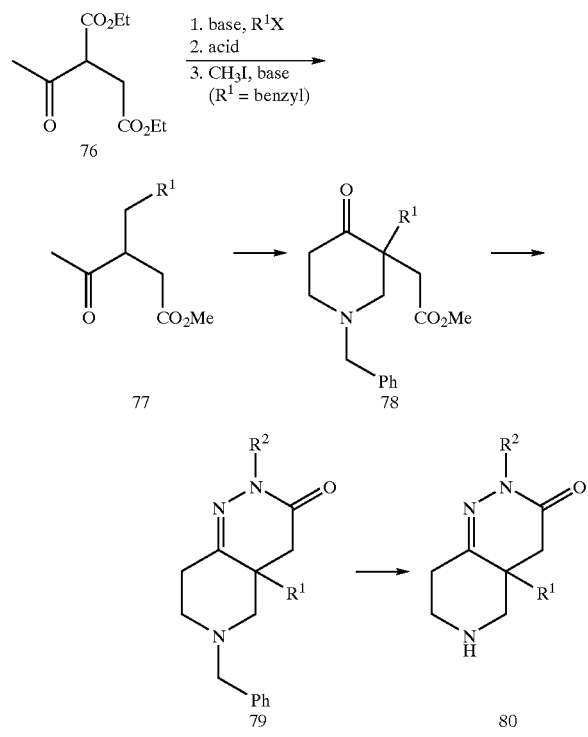

SCHEME 23: Treatment of a ketodiester of formula 76 with an alkyl halide in the presence of a base such as sodium hydride followed by acid-catalyzed hydrolysis and decarboxylation, followed by esterification with methyliodide and a suitable base affords a compound of formula 77. Reaction of a compound of formula 77 with a suitable aldehyde such as formaldehyde and benzylamine affords a compound of formula 78. Reaction of a compound of formula 78 with a hydrazin generates chiral compounds of formula 79. Deprotection of the nitrogen affords compounds of formula 80.

SCHEME 24

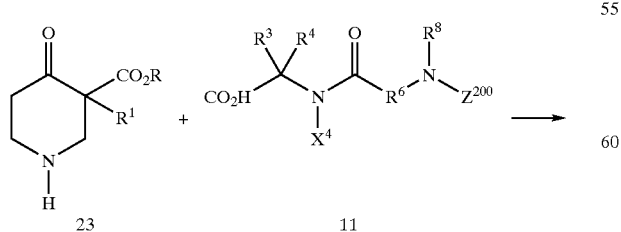

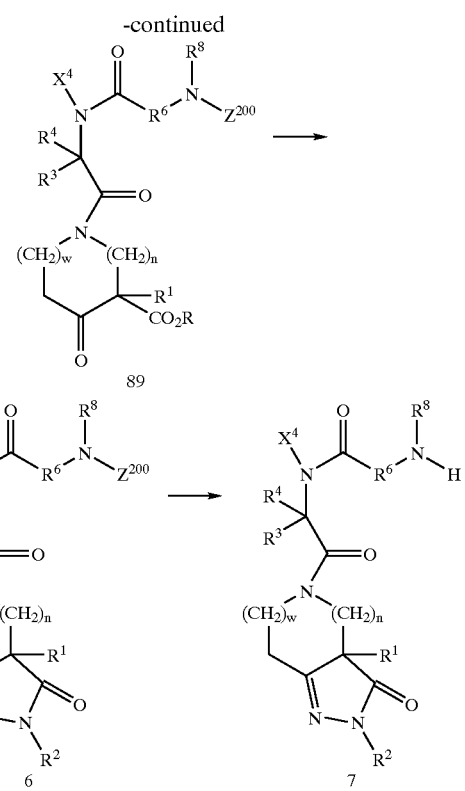

SCHEME 24: Treatment of an amine of formula 23 with an acid of formula 11 in an inert solvent such as dichloromethane or DMF by a coupling reagent such as EDC or DCC in the presence of HOBT affords compounds of formula 89. Reaction of compounds of formula 89 with a hydrazine generates compounds of formula 6. Deprotection of the nitrogen affords compounds of formula 7.

SCHEME 25

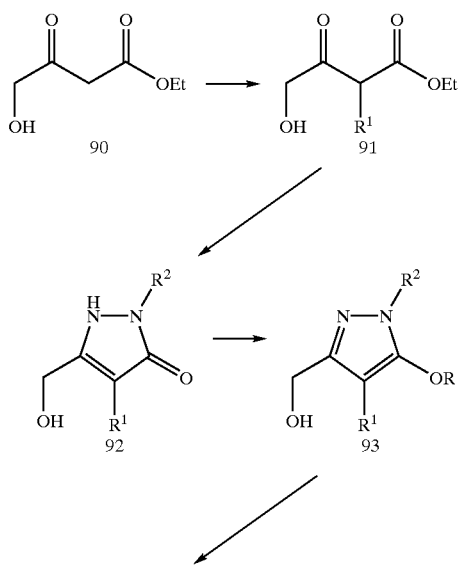

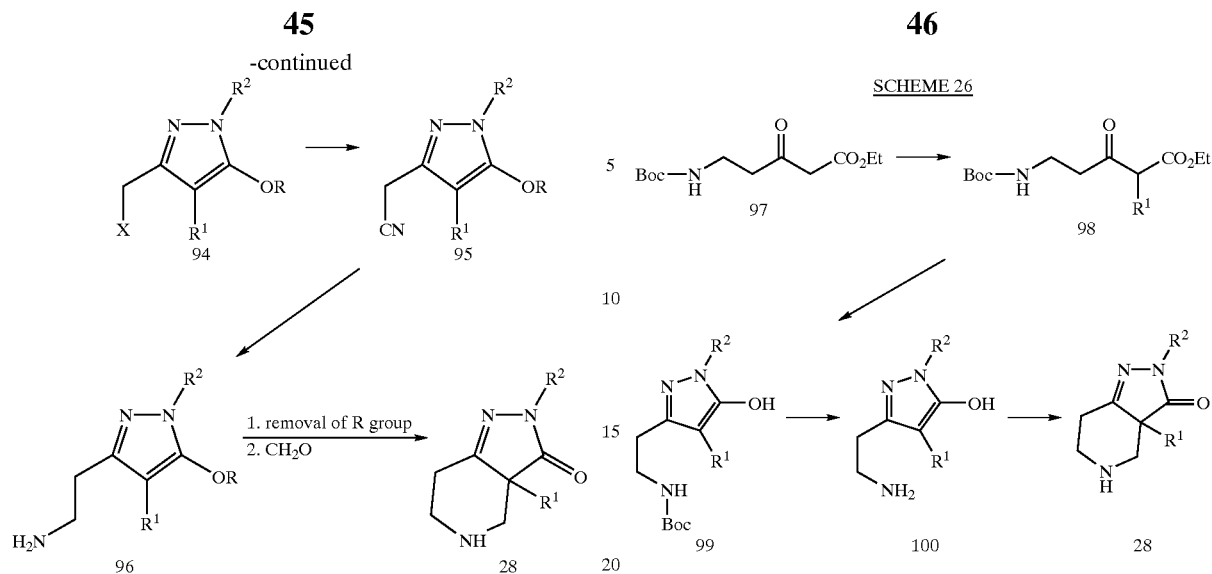

SCHEME 25: Treatment of a hydroxyacetoacetate ester of formula 90 with an alkyl halide in the presence of a suitable base such as sodium hydride affords compounds of formula 91. Reaction of 91 with a hydrazine generates compounds of formula 92. O-Alkylation of the carbonyl oxygen of 92 affords 93 which is converted to the halide 94. Displacement of the halide X by cyanide ion affords the nitrile 95. Reduction of 95 gives the primary amine 96 which is deprotected and cyclized in the presence of formaldehyde to afford 28.

SCHEME 26: Treatment of a beta-keto-protected aminovalerate such as 97 with an alkyl halide in the presence of a suitable base such as sodium hydride affords compounds of formula 98. Reaction of compounds of formula 98 with a hydrazine generates compounds of formula 99. Deprotection of compounds of formula 99 affords primary amines of formula 100. Cyclization of compounds of formula 100 in the presence of formaldehyde affords compounds of formula 28.

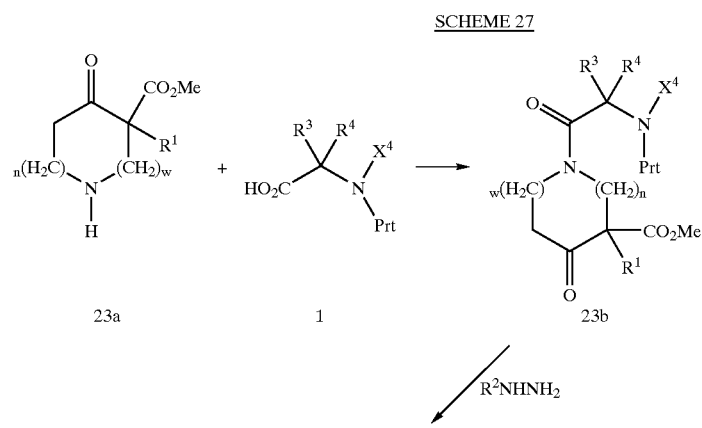

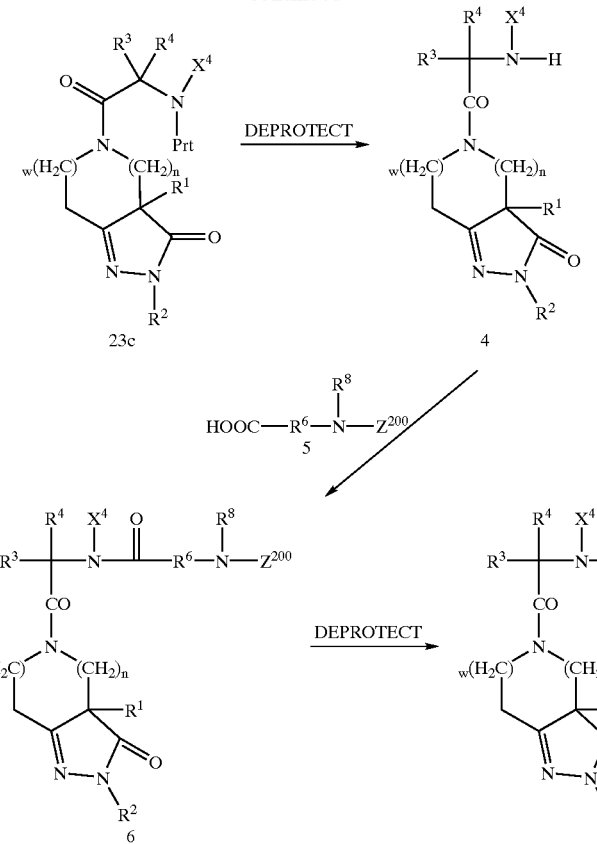

SCHEME 27: Treatment of the amine of formula 23a with an acid such as 1 in the presence of EDC and HOAT in a suitable solvent provides keto-esters of formula 23b. The keto-ester 23b can be treated with a salt of hydrazine in the presence of sodium acetate in refluxing ethanol to give hydrazines of formula 23c. Deprotection under suitable conditions gives amines of formula 4. Coupling of intermediates of formula 4 to amino acids of formula 5 can be effected as described above to give intermediates of formula 6. Deprotection of amine 6 affords compounds of formula 7.

SCHEME 28

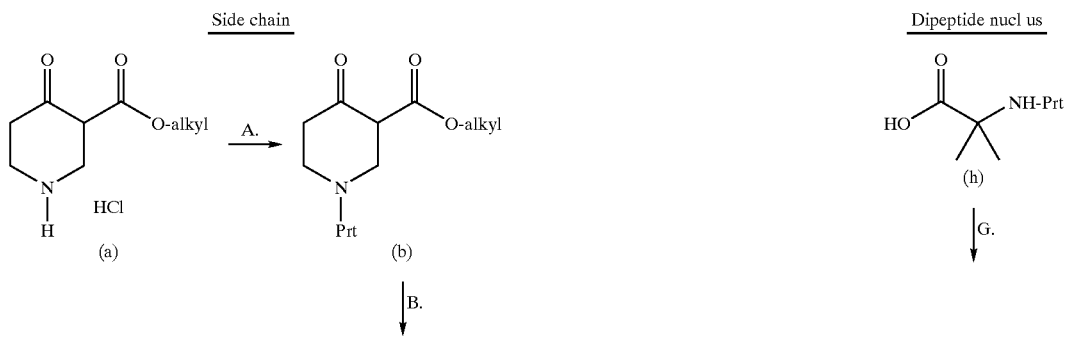

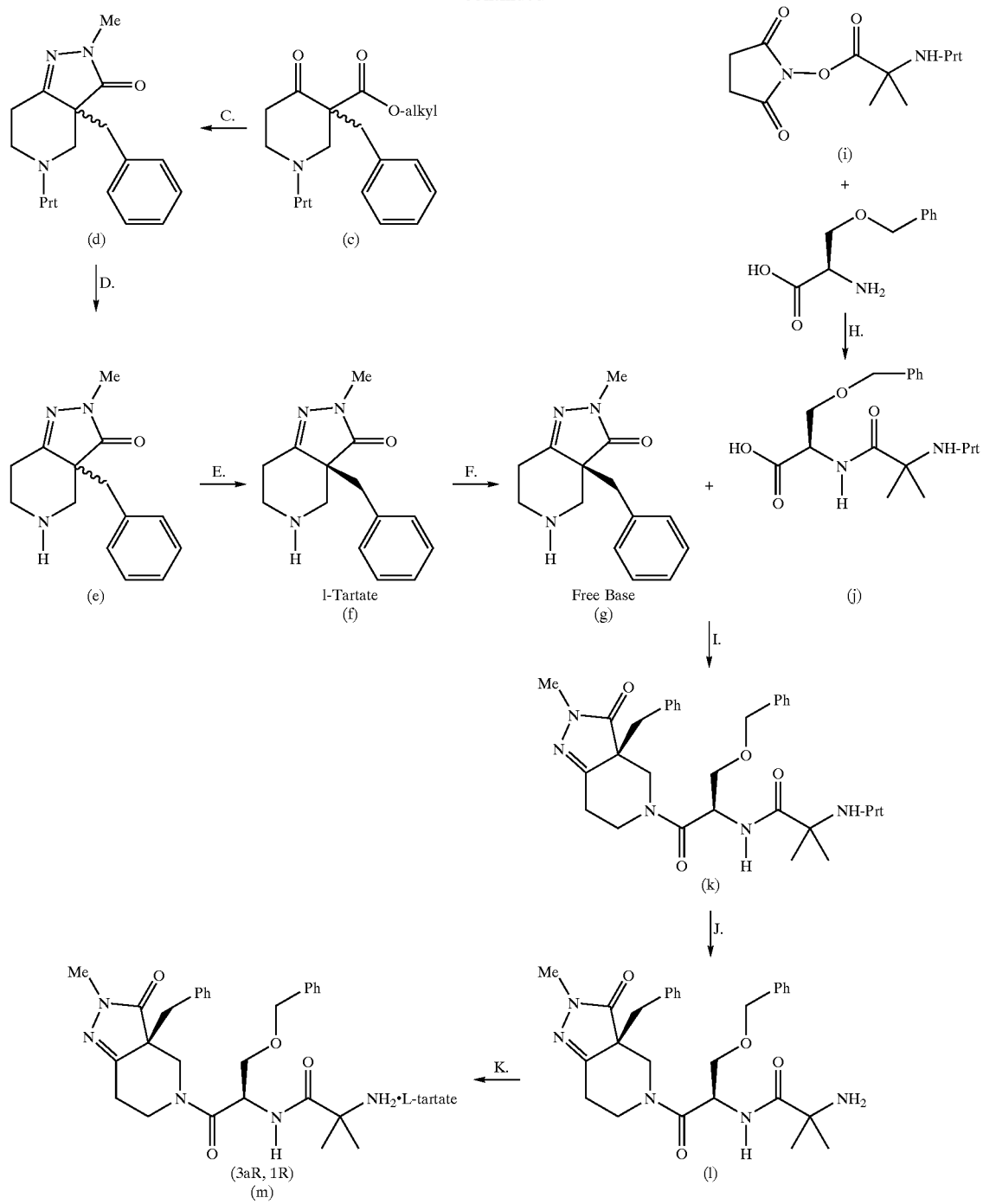

SCHEME 28: Prt represents an amino protecting group that will be known to one skilled in the art BOC has been used for Prt to illustrate the preferred protecting group but the use of BOC should not be taken as limiting the scope of this disclosure. Further, although the scheme illustrates the synthesis of the compound of formula m using particular isomers, other isomers and/or isomeric mixtures are also within the scope the instant disclosure.

Step A.

To a solution of 4-oxo-piperidine-3-carboxylic acid ethyl ester hydrochloride in a reaction inert organic solvent such as IPE, THF, methylene chloride and EtOAc with or without water as a cosolvent, preferably IPE and water, is added an inorganic or organic base such as TEA, DMAP, an hydroxide or a carbonate, preferably TEA, followed by an amine protecting group, preferably $(Boc)_2O$. The mixture is stirred for about 1–24 hours, preferably overnight, preferably under nitrogen. The organic phase is separated and worked-up according to standard procedures known to those skilled in the art and concentrated to afford the desired product as crystals.

Step B.

To a solution of 4-oxo-piperidine-1,3-dicarboxylic acid 1-tert-butyl ester 3 ethyl ester in an organic solvent such as THF, IPE, an alcohol, DNF, or DMSO, preferably DMF, an inorganic or organic base such as TEA, DMAP, an hydroxide or a carbonate, preferably lithium carbonate, is added, followed by benzyl bromide. The mixture is heated to about 25–100° C., preferably 60° C., and stirred for about 1–24 hours, preferably 20 hours. The reaction mixture is then cooled to room temperature and extracted with an organic solvent such as IPE, toluene, THF or EtOAc and worked-up according to standard procedures known to those skilled in the art to yield the desired compound.

Step C.

To a solution of 3-benzyl-4-oxo-piperidine-1,3-dicarboxylic acid 1-tert-butyl ester 3-ethyl ester in an organic solvent such as an alcohol, THF or toluene is added methylhydrazine, followed by an add such as sulfuric acid, HCl, AcOH or TsOH, preferably acetic acid at about 0° C. to room temperature. The reaction mixture is heated slowly to about 40–100° C., preferably about 65° C. and stirred for about 3–10 hours, preferably about 7.5 hours. After cooling to room temperature, the organic layer is washed with 10% sodium bicarbonate and worked-up according to standard procedures known to those skilled in the art and concentrated to yield the desired compound.

Step D.

The concentrated solution from step C is mixed with, an organic solvent such as IPE, cooled to about −10–10° C., preferably 0° C., an acid such as $MeSO_2H$, TFA or HCl, preferably HCl gas, is introduced repeatedly and stirred at room temperature until the hydrolysis is complete. The mixture is concentrated, an organic solvent such as methylene chloride, IPE or THF is added, followed by a base such as a hydroxide, a carbonate, preferably $NH_4OH$. The mixture is then extracted with methylene chloride, IPE or THF and concentrated to yield the desired compound.

Step E.

To a solution of 3a-benzyl-2-methyl-2,3a,4,5,6,7-hexahydro-pyrazolo[4,3-c]pyridin-3-one in a mixture of acetone/water (1% to 11% water, preferably 5% water in acetone) is added L-tartaric acid. The mixture is heated to 250° C., preferably about 50° C., and stirred, preferably overnight. The reaction mixture is cooled to preferably about 10–15° C. and precipitates are filtered, washed with cold acetone/water and dried to yield the desired compound.

Step G.

2-Aminoisobutyric acid, a base such as a hydroxide, preferably 1N NaOH, $(Boc)_2O$ and an organic solvent such as THF, IPE or dioxane are mixed together and stirred at room temperature overnight. The reaction mixture is diluted with organic solvent such as ethyl acetate and adjusted to about pH 3 to 7 by adding an aqueous acid such as HCl. The organic phase is separated and worked-up according to standard procedures known to those skilled in the art to yield the desired compound.

Step H.

To a solution of 2-amino-3-benzyloxy-propionic acid in water and an inorganic or organic base, preferably TEA, is added 2-tert-butoxycarbonylamino-2-methyl-propionic acid 2,5-dioxo-pyrrolidin-1-yl ester in an organic solvent such as THF. The mixture is stirred preferably overnight at preferably room temperature, preferably under nitrogen. An aqueous acid such as 10% citric acid solution is added to the mixture. The mixture is stirred for several minutes, then diluted with an organic solvent such as ethyl acetate. The organic phase is separated from the mixture and worked-up according to standard procedures known to those skilled in the art and then concentrated to yield the desired compound.

Steps F and 1.

To a solution of 3a-(R)-benzyl-2-methyl-2,3a,4,5,6,7-hexahydro-pyrazolo[4,3-c]pyridin-3-one, L-tartrate in organic solvent such as ethyl acetate at about −78 to −20° C., preferably about −66° C., is added a base such as TEA. The mixture is stirred for 1–24 hours, preferably about 1.5 hours. After removal of the precipitated salt, 3-benzyloxy-2-(2-tert-butoxycarbonylamino-2-methyl-propionylamino)-propionic acid and a base such as TEA are added at about −50 to 0° C., preferably about −35° C., followed by the addition of a peptide coupling reagent, preferably 50% 1-propane phosphonic acid cyclic anhydride (PPAA) in ethyl acetate. The mixture is stirred for about 1–6 hours, preferably about 2 hours at −50 to 0° C., preferably about −20° C. to about −27° C., then the temperature was slowly raised to preferably about 0° C. The reaction mixture is poured into water and extracted with an organic solvent such as IPE and the organic layer is separated and worked-up according to standard methods known to those skilled in the art to yield the desired compound.

Step J.

To a solution of {1-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethylcarbamoyl]-methyl-ethyl}-carbamic acid tert-butyl ester in an organic solvent such as methylene chloride at about −10 to 10° C., preferably about 0–5° C. is added TFA, preferably the temperature is maintained below about 5° C. The temperature is then raised to room temperature. The mixture is stirred for about 1–6 hours, preferably about 3 hours. Methylene chloride is replaced with another organic solvent such as ethyl acetate. The mixture is then adjusted to about pH 7 to pH 9, preferably pH 8, with an aqueous base such as saturated sodium bicarbonate solution and then worked-up according to standard methods known to those skilled in the art to yield the desired compound.

Step K.

To a solution of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]2-methyl-propionamide from step I in an alcohol such as methanol is added L-(+)-tartaric acid and the mixture is stirred overnight. The resulting solution is filtered and concentrated. An organic solvent such as IPE or ethyl acetate is added and the remaining alcohol is removed azeotropically. The solid that is isolated is dissolved in ethyl acetate and the solution is refluxed, then allowed to cool to room temperature to yield crystals of the desired product.

The following examples are provided for the purpose of further illustration only and are not intended to be limitations on the disclosed invention.

General Experimental Procedures:

Amicon silica 30 $\mu M$, 60 Å pore size, was used for column chromatography. Melting points were taken on a Buchi 510 apparatus and are uncorrected. Proton and carbon NMR spectra were recorded on a Varian XL-300, Bruker AC-300, Varian Unity 400 or Bruker AC-250 at 25° C. Chemical shifts are expressed in parts per million down field from trimethylsilane. Particle beam mass spectra were obtained on a Hewlett-Packard 5989A spectrometer using ammonia as the source of chemical ionization. For initial sample dissolution, chloroform or methanol was employed. Liquid secondary ion mass spectra (LSIMS) were obtained on a Kratos Concept-1S high resolution spectrometer using cesium ion bombardment on a sample dissolved in a 1:5 mixture of dithioerythritol and dithiothreitol or in a thioglycerol matrix. For initial sample dissolution chloroform or methanol was employed. Reported data are sums of 320 scans calibrated against cesium iodide. TLC analyses were performed using E. Merck Kieselgel 60 F254 silica plates visualized (after elution with the indicated solvent(s)) by staining with 15% ethanolic phosphomolybdic acid and heating on a hot plate.

General Procedure A (Peptide coupling using EDC): A 0.2–0.5 M solution of the primary amine (1.0 equivalent) in dichloromethane (or a primary amine hydrochloride and 1.0–1.3 equivalents of triethylamine) is treated sequentially with 1.0–1.2 equivalents of the carboxylic acid coupling partner, 1.5–1.8 equivalents hydroxybenzotriazole hydrate (HOBT) or HOAT and 1.0–1.2 equivalents (stoichiometrically equivalent to the quantity of carboxylic acid) 1-(3 dimethylaminopropyl)-3-ethylcarbodiimide hydrochloride (EDC) and the mixture is stirred overnight in an ice bath (the ice bath is allowed to warm, thus the reaction mixture is typically held at about 0–20° C. for about 46 h and about 20–25° C. for the remaining period). The mixture is diluted with ethyl acetate or other solvent as specified, and the resulting mixture washed twice with 1N NaOH, twice with 1N HCl (if the product is not basic), once with brine, dried over $Na_2SO_4$, and concentrated giving the crude product which is purified as specified. The carboxylic acid component can be used as the dicyclohexylamine salt in coupling to the primary amine or hydrochloride of the latter; in this case no triethylamine is employed.

EXAMPLE 1

2-Amino-N-{1(R)-benzyloxymethyl-2-[3a-(R)-(4-fluoro-benzyl)-2-methyl-3-oxo-2,3,3a,4,6,7-hexahydro-pyrazolo[4,3-c]pyridin-5-yl]-2-oxo-ethyl}-isobutyramide hydrochloride and
2-Amino-N-{1(R)-benzyloxymethyl-2-[3a-(S)-(4-fluoro-benzyl)-2-methyl-3-oxo-2,3,3a,4,6,7-hexahydro-pyrazolo[4,3 c]pyridin-5-yl]-2-oxo-ethyl}isobutyramide hydrochloride A. 4-Oxo-piperidine-1,3-dicarboxylic acid 1-tert-butyl ester 3-ethyl ester A mixture of 8.00 g (38.5 mmol) of 4-oxo-piperidine-3-carboxylic acid ethyl ester hydrochloride, 9.23 g (42.4 mmol) of di-tert-butyldicarbonate, and 3.89 g (38.5 mmol) of triethylamine in 150 mL of THF was stirred at room temperature for about 72 h. The mixture was concentrated and the residue was dissolved in ethyl acetate and washed three times each with 10% aqueous HCl, saturated aqueous sodium bicarbonate solution, and brine, dried over $MgSO_4$, and concentrated to give 10.0 g of 1A as a white solid. MS (Cl, $NH_3$) 272 ($MH^+$).

B. 3(R,S)-(4-Fluoro-benzyl)-4-oxo-piperidine-1,3-dicarboxylic acid 1-tert-butyl ester 3-ethyl ester To a solution of 2.00 g (7.4 mmol) 1A in 10 mL of DMF was added 282 mg (7.4 mmol) of sodium hydride (60% oil dispersion) and the mixture was stirred at room temperature for about 15 min. A solution of 1.39 g (7.4 mmol) 4-fluorobenzyl bromide in 7 mL of DMF was added to the stirring solution and the mixture was stirred for about 72 h at room temperature. The mixture was diluted with ethyl acetate and washed once with water and four times with brine, dried over $MgSO_4$, and concentrated to give 2.8 g of 1B. MS (Cl, $NH_3$) 380 ($MK^+$).

C. 3a-(R,S)-(4-Fluoro-benzyl)-2-methyl-3-oxo-2,3,3a,4,6,7-hexahydro-pyrazolo[4,3-c]pyridine-5-carboxylic acid tert-butyl ester A mixture of 2.54 g (6.7 mmol) of 1B and 309 mg (6.7 mmol) of methylhydrazine in 100 mL of ethanol was heated at reflux for about 8 h. The mixture was concentrated and the residue was dissolved in 100 mL toluene and heated at reflux for about 17 h. The mixture was concentrated and the residue was purified by silica gel chromatography using an elution gradient of (18.82 v/v ethyl acetate:hexane) to (75:25 v/v ethyl acetate:hexane) to give 1.0 g of 1C as a clear colorless oil. MS (Cl, $NH_3$) 362 ($MH^+$).

D. 3a-(R,S)-(4-Fluoro-benzyl)-2-methyl-2,3a,4,5,6,7-hexahydro-pyrazolo[4,3-c]pyridin-3-one trifluoroacetate To 1.00 g (2.8 mmol) of 1C was added 10 mL of trifluoroacetic acid at about 0° C. and the mixture was stirred for about 1 h. Ethyl acetate was added and the mixture was concentrated to give 1.0 g of 1D. MS (Cl, $NH_3$) 263 ($MH^+$).

E. (R)-3-Benzyloxy-2-(2-tert-butoxycarbonylamino-2-methyl-propionylamino)-propionic acid To 1.83 g (6.2 mmol of N-t-BOC-O-benzyl-D-serine in 35 mL of DMF was added 1.02 g (7.4 mmol) of potassium carbonate followed by 0.92 g (6.5 mmol) of iodomethane. The mixture was stirred overnight at about 24° C. under an atmosphere of nitrogen. The reaction mixture was diluted with 200 mL of water, and extracted three times with ethyl acetate. The combined organics were washed five times with water and once with brine, dried over $MgSO_4$ and concentrated. The crude (R)-3-benzyloxy-2-tert-butoxycarbonyl-amino-propionic acid methyl ester was dissolved in 15 mL of cold trifluoroacetic acid at about 0° C. and the mixture was stirred for about 2 h. The mixture was concentrated and the residue was diluted with 1N NaOH and extracted three times with ethyl acetate. The combined organic extracts were washed with brine and dried over $Na_2SO_4$ to give 0.84 g (4.02 mmol) of the resulting (R)-2-amino-3-benzyloxy-propionic acid methyl ester which was coupled to 0.81 g (4.02 mmol) of N-t-BOC-α-methylalanine to give 1.80 g of (R)-3-benzyloxy-2-(2-tert-butoxycarbonylamino-2-methyl-propionylamino)-propionic acid methyl ester. The crude product was dissolved in 20 mL of 4:1 THF water and a solution of 335 mg (7.98 mmol) of lithium hydroxide hydrate in 1 mL of water was added to the solution and the mixture was stirred overnight at room temperature. The mixture was concentrated and the residue was diluted with ethyl acetate and acidified with aqueous HCl and extracted three times with ethyl acetate. The organic extracts were combined and washed once with brine, dried over $Na_2SO_4$ and concentrated to give 1.60 g of 1E as an oil which solidified on standing. $^1H$ NMR ($CDCl_3$ 300 MHz) δ 7.30 (m, 5H), 7.10 (d, 1H), 5.07 (bs, 11K), 4.68 (m, 1H), 4.53 (q, 2H) 4.09 (m, 1H), 3.68 (m, 1H), 1.3–1.5 (m, 15H).

F. (1-{1(R)-Benzyloxymethyl-2-[3a-(R,S)-fluoro-benzyl)-2-methyl-3-oxo-2,3,3a,4,6,7-hexahydro-prazolo[4,3-c]pyridin-5-yl]-2-oxo-ethylcarbamoyl}-methyl-ethyl)-carbamic acid tert-butyl ester According to the method outlined in General Procedure A, 193 mg (0.51 mmol) of 1D and 196 mg (0.51 mmol) of 1E were coupled to give a mixture of diastereomers. The residue was purified by silica gel chromatography using an elution gradient of (1:1 v/v ethyl acetate:hexane) to 100% ethyl acetate to give 60 mg of less polar 1F isomer 1 and 100 mg of more polar 1F isomer 2. MS (Cl, $NH_3$) 624 ($MH^+$) for both isomers.

G. 2-Amino-N-{1(R)-benzyloxymethyl-2-[3a-(R)-(4-fluoro-benzyl)-2-methyl-3-oxo-2,3,3a,4,6,7-hexalhydro-pyrazolo[4,3-c]pyridin-5-yl]-oxo-ethyl}-isobutyramide hydrochloride To 60 mg (0.10 mmol) of 1F isomer 1 in 10 mL of ethanol was added 4 mL of concentrated HCl and the mixture was stirred at room temperature for about 2 h. The mixture was concentrated and the residue was precipitated from ethanol/hexane to give 50 mg of 1 G isomer 1 as a white powder. MS (Cl, $NH_3$) 524 ($MH^+$). $^1HNMR$ ($CD_3OD$): (partial) δ 7.32

(m, 5H), 7.12 (m, 2H), 6.91 (m, 2H), 5.15 (m, 1H), 4.54 (s, 2H), 3.78 (m, 2H)3.02 (m, 7H), 2.66 (m, 2H), 1.57 (s, 6H).

H. 2-Amino-N-{1(R)-benzyloxymethyl-2-[3a-(S)-(4-fluoro-benzyl)-2-methyl-3-oxo-2,3,3a,4,6,7-hexahydropyrazolo[4,3-c]pyridin-5-yl]-2-oxo-ethyl}-isobutyramide hydrochloride To 100 mg (0.16 mmol) of 1F isomer 2 in 10 mL of ethanol was added 4 mL of concentrated HCl and the mixture was stirred at room temperature for about 2 h. The mixture was concentrated and the residue was precipitated from ethanol/hexane to give 60 mg of 1H isomer 2 as a white powder. MS (Cl, $NH_3$) 524 (MH$^+$). $^1$HNMR (CD$_3$OD): (partial) δ 7.32 (m, 5H), 7.08 (m, 2H), 6.95 (m, 2H), 6.80 (m, 2H), 5.30 (m, 1H), 4.61 (m, 3H), 3.80 (m, 2H), 2.58 (m, 3H), 1.58 (s, 6H).

EXAMPLE 2
2-Amino-N-[2-[3a-(R,S)-(4-fluoro-benzyl)-2-methyl-3-oxo-2,3,3a,4,6,7-hexahydro-pyrazolo[4,3-c]pyridin-5-yl]-1-(R)-(1H-indol-3-ylmethyl)-2-oxo-ethyl]isobutyramide hydrochloride A. (R)-2-Amino-3-[(1H-indol-3-yl)-propionic acid methyl ester To 4.92 g (16.2 mmol) of N-α-t-BOC-D-tryptophan in 100 mL of DMF was added 2.46 g (17.8 mmol) of potassium carbonate followed by 2.41 g (17.0 mmol) of iodomethane, and the mixture was stirred overnight at 24° C. under an atmosphere of nitrogen. The reaction mixture was diluted with water, and extracted three times with ethyl acetate. The combined organics were washed five times with 500 mL of water and once with brine, dried over MgSO$_4$ and concentrated to give 4.67 g of a white solid. To the crude (R)-2-tert-butoxycarbonylamino-3-(1H-indol-3-yl) propionic acid methyl ester was added 15 mL of cold trifluoroacetic acid at about 0° C. and the mixture was stirred for about 2 h. The mixture was concentrated and the residue was diluted with 1N NaOH and extracted three times with ethyl acetate. The combined organic extracts were washed with brine and dried over Na$_2$SO$_4$ to give (R)-2-amino-3-(1H-indol-3-yl)-propionic acid methyl ester as an orange oil in quantitative yield.

B. (R)-2-(2-tert-Butoxcarbonylamino-2-methyl-propionylamino)-3-(1H-indol-3-yl)-propionic acid methyl ester.

The crude product from 2A 1.55 g (7.1 mmol) was coupled to 1.44 g (7.1 mmol of N-t-BOC-α-methylalanine according to Procedure A to give an oil which was purified by silica gel chromatography using a gradient of 10%, 20%, 30%, 40% and 50% ethyl acetate in hexane to elute. Recovered 1.32 g of (R)-2-(2-tert-butoxycarbonylamino-2-methyl-propionylamino)-3-(1H-indol-3-yl)-propionic acid methyl ester.

C. (R)-2-(2-tert-Butoxycarbonylamino-2-methyl-propionylamino)-3-(1H-indol-3-yl)-propionic acid To a solution of 1.03 g (2.64 mmol) of 2B in 10 mL of THF was added 381 mg (9.1 mmol) of lithium hydroxide hydrate in 2 mL of water and the mixture was stirred overnight at room temperature. Excess THF was removed by evaporation, and the basic aqueous mixture was extracted three times with ethyl acetate, and then acidified to pH 4 with dilute acetic or hydrochloric acid. The product was extracted with ethyl acetate and the combined organic extracts were washed with brine, dried over MgSO$_4$ and evaporated to give 1.03 g of 2C as an orange foam. MS (Cl, NH$_3$) 390 (MH$^+$). $^1$H NMR (CDCl$_3$ 300 MHz) δ 7.61 (d, 1H), 7.48 (d, 1H), 7.27 (t, 1H), 7.10 (t, 1H), 4.81 (bs, 1H), 3.35 (m, 1H), 1.49 (s, 6H), 1.32 (s, 9H).

D. {1-[2-[3a-(R,S)-(4-Fluoro-benzyl)-2-methyl-3-oxo-2,3,3a,4,6,7-hexahydro-pyrazolo[4,3-c]pyridin-5-yl]-1-(R)-(1H-indol-3-ylmethyl)-2-oxo-ethylcarbamoyl]-1-methyl-ethyl}-carbamic acid tert-butyl ester According to the method outlined in General Procedure A, 193 mg (0.51 mmol) of 1D and 200 mg (0.51 mmol) of 2C were coupled and the residue was purified by silica gel chromatography using an elution gradient of (1:1 v/v ethyl acetate:hexane) to 100% ethyl acetate to give 230 mg of 2D. MS (Cl, NH$_3$) 633 (MH$^+$).

E. 2-Amino-N-[2-[3a-(R,S)-(4-fluoro-benzyl)-2-methyl-3-oxo-2,3,3a,4,6,7-hexahydro-pyrazolo[3,4-c]pyridin-5-yl]-1(R)-(1H-indol-3-ylmethyl)-2-oxo-ethyl]-isobutyramide hydrochloride To 230 mg (0.36 mmol) of 2D in 10 mL of ethanol was added 4 mL of concentrated HCl and the mixture was stirred at room temperature for about 2 h. The mixture was concentrated and the residue was precipitated from ethanol/hexane to give 130 mg of 2E as a white powder. MS (Cl, NH$_3$) 533 (MH$^+$). $^1$HNMR (CD$_3$OD): (partial) δ 7.79 (d, 1H), 7.48 (m, 1H), 7.33 (m, 2H), 7.19–6.77 (m, 7H), 6.54 (m, 1H), 5.17 (m, 1H), 4.02 (m, 1H), 3.11–2.68 (m, 6H), 2.47 (m, 2H), 2.03 (m, 2H), 1.59 (m, 6H).

EXAMPLE 3
2-Amino-N-[2-(3a-(R,S)-benzyl-2-methyl-3-oxo-2,3,3a,4,6,7-hexahydro-pyrazolo[3,4-c]pyridin-5-yl)-1R-(1H-indol-3-ylmethyl)-2-oxo-ethyl]isobutyramide A. 4-Oxo-piperidine-1,3-dicarboxylic acid 1-tert-butyl ester 3-methyl ester To a mixture of 7.00 g (36.2 mmol) of 4-oxo-piperidine-3-carboxylic acid methyl ester and 8.82 g (72.3 mmol) of 4,4-dimethylaminopyridine in 200 mL of methylene chloride at about 0° C. was added a solution of 7.88 g (36.2 mmol) of di-tert-butyldicarbonate in 150 mL of methylene chloride over about 30 min. The mixure was warmed to room temperature and then stirred for about 17 h. The mixture was concentrated and the residue was diluted with chloroform and washed three times each with 10% aqueous HCl, saturated aqueous sodium bicarbonate solution and brine, dried over MgSO$_4$ and concentrated to give 9.18 g of a dear yellow oil.

B. 3(R,S)-Benzyl-4-oxo-piperidine-1,3-dicarboxylic acid 1-tert-butyl ester 3-methyl ester To a solution of 5.00 g (19.4 mmol 3A in 10 mL of DMF was added 745 mg (7.4 mmol) of sodium hydride (60% oil dispersion) and the mixture was stirred at room temperature for about 15 min. A solution of 3.32 g (19.4 mmol) benzylbromide in 15 mL of DMF was added to the stirring solution by cannula and the mixture was stirred for about 42 h at room temperature. The mixture was diluted with ethyl acetate and washed once with water and four times with brine, dried over MgSO$_4$, and concentrated to give 6.0 g of 3B as a yellow oil. MS (Cl, NH$_3$) 348 (MK$^+$).

C. 3a-(R,S)-Benzyl-2-methyl-3-oxo-2,3,3a,4,6,7-hexahydro-pyrazolo[4,3-c]-pyridine-5-carboxylic acid tert-butyl ester A mixture of 4.00 g (11.5 mmol) of 3B and 530 mg (11.5 mmol) of methylhydrazine in 100 mL of ethanol was heated at reflux for about 8 h. The mixture was concentrated and the residue was dissolved in 100 mL toluene and heated at reflux for about 17 h. The mixture was concentrated and the residue was purified by silica gel chromatography using an elution gradient of (15:85 v/v ethyl acetate:hexane) to (75:25 v/v ethyl acetate:hexane) to give 2.6 g of 3C as a clear colorless oil. MS (Cl, NH$_3$) 344 (MH$^+$).

D. 3a-(R,S)-Benzyl-2-methyl-2,3a,4,5,6,7-hexahydro-pyrazolo[4,3-c]pyridin-3-one

To 2.60 g (7.6 mmol) of 3C was added 20 mL of trifluoroacetic acid at about 0° C. and the mixture was stirred for about 2.5 h. Ethyl acetate was added and the solution was washed with 6N NaOH, dried over MgSO$_4$ and concentrated to give 1.8 g of 3D. MS (Cl, NH$_3$) 244 (MH$^+$).

E. {1-[2-(3a-(R,S)-Benzyl-2-methyl-3-oxo-2,3,3a,4,6,7-hexahydro-pyrazolo[4,3-c]pyridin-5-yl)-1R-(1H-indol-3-ylmethyl)-2-oxo-ethycarbamoyl]-1-methyl-ethyl}-carbamic acid tert-butyl ester According to the method outlined in General Procedure A, 125 mg (4.6 mmol) of 3C and 1.75 g (0.51 mmol) of 2C were coupled and the residue was purified by silica gel chromatography using an elution gradient of (6:4 v/v ethyl acetate:hexane) to 7% methanol in ethyl acetate to give 150 mg of 3E.

F. 2-Amino-N-[2-(3a-(R,S)-benzyl-2-methyl-3-oxo-2,3,3a,4,6,7-hexahydro-pyrazolo[4,3-c]pyridin-5-yl)-1R-(1H-indol-3-ylmethyl)-2-oxo-ethyl]-isobutyramide hydrochloride To 150 mg (0.24 mmol) of 3E in 15 mL of ethanol was added 5 mL of concentrated HCl and the mixture was stirred at room temperature for about 3 h. The mixture was concentrated and the residue was crystallized from ethanol/hexane to give 100 mg of 3F. MS (Cl, NH$_3$) 515 (MH$^+$). $^1$HNMR (CD$_3$OD): δ 7.20–6.91 (m, 9H), 6.56 (m, 1), 5.17 (m, 1H), 4.05 (m, 1H), 2.96 (s, 3H), 2.62 (m, 1H), 2.38 (m, 1H), 2.06 (m, 2H), 1.61 (m, 8H).

EXAMPLE 4

2-Amino-N-[2(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide hydrochloride and 2-Amino-N-[2-(3a-(S)-benzyl-2-methyl-3-oxo-2,3,3a,4,6,7-hexahydro-pyrazolo[4,3-c]pryridin-5-yl)-1-(R)-benzyloxymethyl-2-oxo-ethyl]-isobutyramide hydrochloride A. {1-[2-(3a-(R,S)-Benyl-2-methyl-3-oxo-2,3,3a,4,6,7-hexahydro-pyrazolo[4,3-c]pyridin-5-yl)-1-(R)-benzyloxymethyl-2-oxo-ethylcarbamoyl]-1-methyl-ethyl}carbamic acid tert-butyl ester According to the method outlined in General Procedure A, 1.12 g (4.6 mmol) of 3C and 1.75 g (0.51 mmol) of 1E were coupled to give a mixture of diastereomers. The residue was purified by silica gel chromatography using an elution gradient of (1:1 v/v ethyl acetate:hexane) to 100% ethyl acetate to give 350 mg of less polar 4A isomer 1 and 250 mg of more polar 4A isomer 2. MS (Cl, NH$_3$) 606 (MH$^+$) for both isomers.

B. 2-Amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]isobutyramide hydrochloride To 250 mg (0.41 mmol) of 4A isomer 1 in 15 mL of ethanol was added 5 mL of concentrated HCl and the mixture was stirred at room temperature for about 5 h. The mixture was concentrated and the residue was precipitated from ethanol/hexane and dried under vacuum to give 130 mg of 4B isomer 1. MS (Cl, NH$_3$) 506 (MH$^+$). $^1$HNMR (CD$_3$OD): δ 7.33 (m, 5H), 7.14 (m, 5H), 5.22 (m, 1H), 4.57 (m, 3H), 3.80 (m, 2H) 3.14 (m, 1H), 3.04 (s, 3H), 2.96 (m, 2H), 2.61 (m, 2H), 1.63 (m, 7H).

C. 2-Amino-N-[2-(3a-(S)-benzyl-2-methyl-3-oxo-2,3,3a,4,6,7-hexahydro-pyrazolo[4,3-c]pyridin-5-yl)-1-(R)-benzyloxymethyl-2-oxo-ethyl]isobutyramide hydrochloride To 250 mg (0.41 mmol) of 4A isomer 2 in 15 mL of ethanol was added 5 mL of concentrated HCl and the mixture was stirred at room temperature for about 5 h. The mixture was concentrated and the residue was precipitated from ethanol/hexane and dried under vacuum to give 120 mg of 4C isomer 2. MS (Cl, NH$_3$) 506 (MH$^+$). $^1$HNMR (CD$_3$OD): δ 7.31 (m, 5H), 7.13 (m, 5H), 6.78 (m, 1H), 5.28 (m $_1$H), 4.62 (m, 3H), 3.81 (M, 2H), 3.14 (m, 1H), 2.62 (m, 3H). 1.58 (m, 7H).

D. 2-Amino-N-[2-(3a-(R)-benzyl-2-methyl-oxo-2,3,3a,4,6,7-hexahydro-pyrazolo[4,3-c]pyridin-5-yl)-1-(R)-benzyloxymethyl-2-oxo-ethyl]isobutyramide methanesulfonate Saturated aqueous sodium bicarbonate was added to 3.60 g (6.6 mmol) of 4B isomer 1 and the mixture was extracted with ethyl acetate. The organic layer was dried over MgSO$_4$ and concentrated. The residue was dissolved in ethyl acetate, cooled to about 0° C. and 0.43 mL (6.6 mmol) of methanesulfonic acid was added and the mixture was stirred for about 0.5 h. Hexane (200 mL) was added to the solution and the mixture was stirred for about 1 h and filtered to give 3.40 g of a white solid. The solid was recrystallized from 3% aqueous ethyl acetate to give 2.55 g of 4D isomer 1 as a white crystalline solid. MS (Cl, NH$_3$) 506 (MH$^+$).

EXAMPLE 5

2-Amino-N-[1-(3a-(R)-benzyl-2-methyl-3-oxo-2,3,3a,4,6,7-hexahydro-pyrazolo[4,3-c]pyridine-5-carbonyl)-4-phenyl-(R)-butyl]-isobutyramide hydrochloride and 2-Amino-N-[1-(3a-(S)-benzyl-2-methyl-3-oxo-2,3,3a,4,6,7-hexahydro-pyrazolo[4,3-c]pyridine-5-carbonyl)-4-phenyl-(R)-butyl]-isobutyramide hydrochloride A. 2-Oxo-5,6-diphenyl-3-(3-phenyl-allyl)-morpholine-4-carboxylic acid t-butyl ester To an about −78° C. solution of 13.8 g (70.0 mmol) of cinnamyl bromide and 4.94 g (14.0 mmol) of t-butyl-(2S, 3R)-(+)-6-oxo-2,3-diphenyl-4-morpholine carboxylate in 350 mL of anhydrous THF was added 28 mL (28 mmol) of 1M sodium bistrimethylsilylamide in THF. The mixture was stirred at about −78° C. for about 1.5 h and then poured into 750 mL of ethyl acetate. The mixture was washed twice with brine, dried over MgSO$_4$ and concentrated to give a yellow oil. The oil was stirred in 150 mL of hexane overnight and the precipitated solid was then collected by filtration to give 3.2 g of 5A as a white solid.

B. 5(S),6(R)-Diphenyl-3(R)-(3-phenyl-allyl)-morpholin-2-one

To 2.97 g (6.33 mmol) of 5A was added 20 mL of trifluoroacetic acid at about 0° C. and the mixture was stirred for about 2 h and then concentrated. The residue was dissolved in water and basified with aqueous NaOH until a pH of 10 was maintained. The mixture was extracted three times with ethyl acetate and the combined organic extracts were washed with brine, dried over MgSO$_4$ and concentrated to give an orange oil which was purified by silica gel chromatography (10:90 v/v ethyl acetate:hexane) to give 880 mg of 5B as a white solid.

C. 2-(R)-Amino-5-phenyl-pentanoic acid

A mixture of 440 mg (1.19 mmol) of 5B and 120 mg of palladium chloride in 20 mL of ethanol and 10 mL of THF was hydrogenated at 45 psi, for about 16 h. The mixture was filtered through diatomaceous earth and concentrated, and the residue was triturated with ether to give 240 mg of 5C as a white solid.

D. 2-tert-Butoxycarbonylamino-2-methyl-propionic acid 2,5-dioxo-pyrrolidin-1-yl ester To a slurry of 5.0 g (24.6 mmol) of N-t-BOC-α-methylalanine in 13.5 mL of methylene chloride was added 3.40 g (29.6 mmol) of N-hydroxysuccinimide and 5.65 g (29.6 mmol) of EDC. The slurry was stirred for about 17 h at room temperature. The mixture was diluted with ethyl acetate and washed twice each with water, saturated sodium bicarbonate solution and brine. Dried over MgSO$_4$ and concentrated. The product was purified by silica gel chromatography (1:1 v/v ethyl acetate:hexanes) to give 5.2 g of the tile compound of this part D as a whit solid.

E. (R)-2-(2-tert-Butoxycarbonylamino-2-methyl-propionylamino-5-phenyl-pentanoic acid A mixture of 203 mg (1.05 mmol) of 5D, 378 mg (1.26 mmol) of 5C and 434 mg (3.36 mmol) of diisopropylethylamine in 2 mL of DMF was stirred over-night. The mixture was diluted with ethyl acetate and extracted twice with 1N HCl. The aqueous phase was extracted once with ethyl acetate. The pooled organic extracts were washed three times with water and once with brine. The mixture was dried over MgSO$_4$ and concentrated. The residue was purified by silica gel chromatography using 80% chloroform in hexane followed by 100% chloroform followed by 10% methanol in chloroform to give 127 mg of 5E.

F. {1-[1-(3a-(R,S)-Benzyl-2-methyl-3-oxo-2,3,3a,4,6,7-hexahydro-pyrazolo[4,3-c]pyridine-5-carbonyl)-4-phenyl-(R)-butylcarbamoyl]-1-methyl-ethyl}-carbamic acid tert-butyl ester According to the method outlined in General Procedure A, 130 mg (0.53 mmol) of 3C and 200 mg (0.53 mmol) of 5E were coupled to give a mixture of diastereomers. The residue was purified by silica gel chromatography using an elution gradient of (1:1 v/v ethyl acetate:hexane) to 100% ethyl acetate to give 40 mg of less polar 5F isomer 1 and 40 mg of more polar 5F isomer 2. MS (Cl, NH$_3$) 604 (MH$^+$) for both isomers.

G. 2-Amino-N-[1-(3a-(R)-benzyl-2-methyl-3-oxo-2,3,3a,4,6,7-hexahydro-pyrazolo[4,3-c]pyridin-5-carbonyl)-4-phenyl-(R)-butyl]isobutyramide hydrochloride To 40 mg (0.07 mmol) of 5F isomer 1 in 10 mL of ethanol was added 4 mL of concentrated HCl and the mixture was stirred at room temperature for about 4 h. The mixture was concentrated and the residue was precipitated from methylene chloride/hexane and dried under vacuum to give 30 mg of 5G isomer 1. MS (Cl, NH$_3$) 504 (MH$^+$). $^1$HNMR (CD$_3$OD): (partial) δ 7.19 (m, 10H), 4.37 (m, 1H), 3.02 (m. 6H), 2.67 (m, 4H), 1.83 (m, 4H). 1.62 (s, 6H), 1.28 (m, 1H).

H. 2-Amino-N-[1-(3a-(S)-benzyl-2-methyl-3-oxo-2,3,3a,4,6,7-hexahydro-pyrazolo[4,3-c]pyridine-5-carbonyl)-4-phenyl-(R)-butyl]-isobutyramide hydrochloride To 40 mg (0.07 mmol) of 5F isomer 2 in 10 mL of ethanol was added 4 mL of concentrated HCl and the mixture was stirred at room temperature for about 4 h. The mixture was concentrated and the residue was precipitated from methylene chloride/hexane and dried under vacuum to give 30 mg of 5H isomer 2. MS (Cl, NH$_3$) 504 (MH$^+$). $^1$HNMR (CD$_3$OD): (partial) 7.25 (m, 9H), 6.88 (m, 1H), 3.04 (s, 3H), 2,71 (m, 4H), 2.48 (m, 2H), 1.75 (m, 4H), 1.62 (m, 6H), 1.28 (m, 1H).

EXAMPLE 6

2-Amino-N-[2-(3a-(R,S)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide hydrochloride A. {1-[2-(3a-(R,S)-Benzyl-2-methyl-3-oxo-2,3,3a,4,6,7-hexahydro-pyrazolo[4,3-c]pyridin-5-yl)1-(R)-benzyloxymethyl-2-oxo-ethylcarbamoy]-1-methyl-ethyl}-carbamic acid tert-butyl ester According to the method outlined in General Procedure A, 200 mg (0.82 mmol) of 3C and 320 mg (0.82 mmol) of 1E were coupled to give a mixture of diastereomers. The residue was purified by silica gel chromatography using an elution gradient of (1:1 v/v ethyl acetate:hexane) to 10% methanol in ethyl acetate to give 170 mg of 6A.

B. 2-Amino-N-[2-(3a-(R,S)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide hydrochloride To 170 mg (0.28 mmol) of 6A in 20 mL of ethanol was added 5 mL of concentrated HCl and the mixture was stirred at room temperature for about 2.5 h. The mixture was concentrated and the residue was precipitated from ethanol/hexane to give 70 mg of 6B. MS (Cl, NH$_3$) 506 (MH$^+$).

$^1$HNMR (CD$_3$OD): δ 7.32 (m, 5H); 7.16 (m, 5H), 522 (m, 1H), 4.67 (m, 1H), 4.55 (m, 2H), 3.79 m, 2H), 3.12 (m, 2H), 3.00 (m, 6H), 2.71 (m, 3H), 1.56 (m, 8H).

EXAMPLE 7

2-Amino-N-[2-(3a-(R,S)-benzyl-2-ethyl-3-oxo-2,3,3a,4,6,7-hexahydro-pyrazolo[4,3-c]pyridin-5-yl)-1-(1H-indol-3-ylmethyl)-2-oxo-ethyl]isobutyramide hydrochloride A. 3a-(R,S)-Benzyl-2-ethyl-3-oxo-2,3,3a,4,6,7-hexahydro-pyrazolo[4,3-c]pyridine-5-carboxylic acid tert-butyl ester To 555 mg (1.60 mmol) of 3B in 27 mL of ethanol was added 240 mg (1.60 mmol) of ethylhydrazineoxalate and the mixture was heated at reflux for about 4 h. The mixture was concentrated and the residue was purified by silica gel chromatography using an elution gradient of (10:1 v/v hexane:ethyl acetate) to (3:7 v/v hexane:ethyl acetate) to give 357 mg of 7A MS (Cl, NH$_3$) 358 (MH$^+$).

B. 3a-(R,S)-Benzyl-2-ethyl-2,3a,4,5,6,7-hexahydro-pyrazolo[4,3-c]pyridin-3-one

To 350 mg (0.98 mmol) of 7A in 3 mL of ethanol was added 1.5 mL of concentrated HCl and the mixture was stirred at room temperature for about 2 h. The mixture was concentrated to give 257 mg of 7B. MS (Cl, NH$_3$) 258 (MH$^+$).

C. {1-[2-(3a-(R,S)-Benzyl-2-ethyl-3-oxo-2,3,3a,4,6,7-hexahydro-pyrazolo[4,3-c]pyridin-5-yl)-1-(R)-(1H-indol-3-ylmethyl)-2-oxo-ethylcarbamoyl]-1-methyl-ethyl}-carbamic acid tert-butyl ester According to the method outlined in General Procedure A, 82 mg (0.28 mmol) of 7B and 100 mg (0.26 mmol) of 2C were coupled and the residue was purified by silica gel chromatography using an elution gradient of 100% methylene chloride to 2% methanol in methylene chloride to give 110 mg of 7C. MS (Cl, NH$_3$) 629 (MH$^+$).

D. 2-Amino-N-[2-(3a-(R,S)-benzyl-2-ethyl-3-oxo-2,3,3a,4,6,7-hexahydro-pyrazolo[4,3-c]pyridin-5-yl)-1-(R)-(1H-indol-3-ylmethyl)-2-oxo-ethyl]-isobutyramide hydrochloride To 100 mg (0.15 mmol) of 7C in 2 mL of ethanol was added 1 mL of concentrated HCl and the mixture was stirred at room temperature for about 2 h. The mixture was concentrated to give 72 mg of 7D as a colorless foam. MS (Cl, NH$_3$) 529 (MH$^+$).

EXAMPLE 8

2-Amino-N-[2-(3a-(R)-benzyl-2-ethyl-3-oxo-2,3,3a,4,6,7-hexahydro-pyrazolo[4,3-c]pyridin-5-yl)-1-(R)-benzyloxymethyl-2-oxo-ethyl]-isobutyramide hydrochloride and 2-Amino-N-[2-(3a-(S)-benzyl-2-ethyl-3-oxo-2,3,3a,4,6,7-hexahydro-pyrazolo[4,3-c]pyridin-5-yl)-1-(R)-benzyloxymethyl-2-oxo-ethyl]-isobutyramide hydrochloride A. {1-[2-(3a-(S)-Benzyl-2-ethyl-3-oxo-2,3,3a,4,6,7-hexahydro-pyrazolo[4,3-c]pyridin-5-yl)-1-(R)-benzyloxymethyl-2-oxo-ethylcarbamoyl]-1-methyl-ethyl}-carbamic acid tert-butyl ester According to the method outlined in General Procedure A, 85 mg (0.29 mmol) of 7B and 100 mg (0.26 mmol) of 1E were coupled to give a mixture of diast r omers. Th residue was purified by silica gel chromatography using an elution gradient of 100% methylene chloride to 2% methanol in methylene chloride to give 6 mg of less polar 8A isomer 1 and 11 mg of more polar BA isomer 2. MS (Cl, NH$_3$) 620 (MH$^+$) for both isomers.

B. 2-Amino-N-[2-(3a-(R)-benzyl-2-ethyl-3-oxo-2,3,3a,4,6,7-hexahydro-pyrazolo[4,3-c]pyridin-5-yl)-1-(R)-benzyloxymethyl-2-oxo-ethyl]-isobutyramide hydrochloride To 5.7 mg (0.009 mmol) of 8A isomer 1 in 1 mL of ethanol was added 0.4 mL of concentrated HCl and the mixture was stirred at room temperature for about 3 h. The mixture was concentrated to give 4.7 mg of 8B isomer 1. MS (Cl, NH$_3$) 520 (MH$^+$). $^1$HNMR (CD$_3$OD): (partial) δ 7.41–7.05 (m, 10H), 5.20 (m, 1H), 4.61 (m, 1H), 4.52 (s, 2H), 3.71 (m, 1H), 3.60 (m, 1H), 2.61 (m, 3H), 1.39 (m, 9H).

C. 2-Amino-N-[2-(3a-(S)-benzyl-2-ethyl-3-oxo-2,3,3a,4,6,7-hexahydro-pyrazolo[4,3-c]pyridin-5-yl)-1-(R)-benzyloxymethyl-2-oxo-ethyl]-isobutyramide hydrochloride To 10 mg (0.016 mmol) of 8A isomer 2 in 1 mL of ethanol was added 0.4 mL of concentrated HCl and the mixture was stirred at room temperature for about 3 h. The mixture was concentrated to give 8 mg of 8C isomer 2. MS (Cl, NH$_3$) 520 (MH$^+$). $^1$HNMR (CD$_3$OD): (partial) δ 7.43–7.00 (m, 10H), 6.81 (m, 1H), 5.32 (m, 1H), 4.63 (m, 2H), 4.53 (m, 1H), 3.72 (m, 1H), 1.37 (m, 9H).

EXAMPLE 9

2-Amino-N-[2-(2-benzyl-3-oxo-2,3,3a,4,6,7-hexahydro-pyrazolo[4,3-c]pyridin-5-yl)-1-(R)-benzyloxymethyl-2-oxo-ethyl]-isobutyramide hydrochloride A. 2-Benzyl-3-hydroxy-2,4,6,7-tetrahydro-pyrazolo[4,3-c]pyridine-carboxylic acid tert-butyl ester A mixture of 800 mg (3.11 mmol) of 3B and 495 mg (3.11 mmol) of benzythydrazine dihydrochloride and 423 mg (3.11 mmol) of sodium acetate trihydrate in 15 mL of ethanol was heated at reflux for about 17 h. The mixture was concentrated and the residue was dissolved in 100 mL of toluene and heated at reflux for about 48 h. The mixture was diluted with ethyl acetate and washed with brine, dried over MgSO$_4$ and concentrated and the residue was purified by silica gel chromatography using 100% ethyl acetate followed by 5% methanol in methylene chloride to give 530 mg of 9A as a light brown solid. MS (Cl, NH$_3$) 330 (MH$^+$).

B. 2-Benzyl-4,5,6,7-tetrahydro-2H-pyrazolo[4,3-c]pyridin-3-ol

To 411 mg (1.24 mmol) of 3E in 30 mL of ethanol was added 10 mL of concentrated HCl and the mixture was stirred at room temperature for about 30 min. The mixture was concentrated and the residue was crystallized from methanol/ethyl acetate to give 353 mg of 9B. MS (Cl, NH$_3$) 230 (MH$^+$).

C. {1-[2-(2-Benzyl-3-hydroxy-2,4,6,7-tetrahydro-pyrazolo[4,3-c]pyridin-5-yl)-1-R-benzyloxymethyl-2-oxo-ethylcarbamoyl]-methyl-ethyl-}-carbamic acid tert-butyl ester According to the method outlined in General Procedure A, 100 mg (0.38 mmol) of 9B and 145 mg (0.38 mmol) of 1E were coupled and the residue was purified by silica gel chromatography (95:5 v/v methanol:methylene chloride) to give 42 mg of 9C as a white solid. MS (Cl, NH$_3$) 592 (MH$^+$).

D. 2-Amino-N-[2-(2-benzyl-3-oxo-2,3,3a,4,6,7-hexahydro-pyrazolo[4,3-c]pyridin-5-yl)-1-(R)-benzyloxymethyl-2-oxo-ethyl]-isobutyramide hydrochloride To 42 mg (0.07 mmol) of 9D in 20 mL of ethanol was added 6 mL of concentrated HCl and the mixture was stirred at room temperature for about 30 min. The mixture was diluted with ethanol concentrated and the residue was precipitated from methanol/ethyl acetate to give 35 mg of 9D as a white solid. MS (Cl, NH$_3$) 492 (MH$^+$). $^1$HNMR (CD$_3$OD): partial) 7.41–7.16 (m, 10H), 5.19 (m, 3H), 4.48 (m, 4H), 3.88 (m, 1H), 3.74 (m, 2H), 2.68 (m, 2H), 1.58 (m, 6H).

EXAMPLE 10

2-Amino-N-{2-[3a-(R)-benzyl-3-oxo-2-(2,2,2-trifluoro-ethyl)-2,3,3a,4,6,7-hexahydro pyrazolo[4,3-c]pyridin-5-yl]-1-(R)-benzyloxymethyl-2-oxo-ethyl}isobutyramide hydrochloride and 2-Amino-N-{2-[3a-(S)-benzyl-3-oxo-2-(2,2,2-trifluoro-ethyl)-2,3,3a,4,67-hexahydro-pyrazolo[4,3-c]pyridin-5-yl]-(R)-benzyloxymethyl-2-oxo-ethyl}isobutyramide hydrochloride A. 3a-(R,S)-Benzyl-3-oxo-2,2,2-fluoro-ethyl)-2,3,3a,4,6,7-hexahydro pyrazolo[4,3-c]pyridine-5-carboxylic acid tert-butyl ester A mixture of 840 mg (2.42 mmol) of 3B and 276 mg (2.42 mmol) of 2,2,2-trifluoroethylhydrazine (70% in water) in 20 mL of ethanol was heated at reflux for about 5 h and then concentrated. The residue was dissolved in 40 mL of toluene and heated at reflux for about 17 h. The mixture was concentrated and the residue was purified by silica gel chromatography (9:1 v/v hexane:ethyl acetate) to give 703 mg of 10A as a yellow oil. MS (Cl, NH$_3$) 412 (MH$^+$).

B. 3a-(R,S)-Benzyl-2-(2,2,2-trifluoro-ethyl)-2,3a,4,5,6,7-hexahydro-pyrazolo[4,3-c]pyridin-3-one To 600 mg (1.46 mmol of 10A at about 0° C. was added 3 mL of cold trifluoroacetic acid and the mixture was stirred for about 3 h, allowing the solution to reach room temperature as it did so. The mixture was concentrated and the residue was dissolved in water and the solution was basified to pH 11 with 5N NaOH and then saturated with potassium carbonate. The solution was extracted three times with ethyl acetate and the combined organic extracts were washed with brine, dried over MgSO$_4$ and concentrated to give 345 mg of 10B as an opaque oil. MS (Cl, NH$_3$) 312 (MH$^+$).

C. (1-{2-[3a-(R,S)-Benzyl-3-oxo-2-(2,2,2-trifluoro-ethyl)-2,3,3a,4,6,7-hexahydro-pyrazolo[4,3-c]pyridin-5-yl]-1-(R)-benzyloxymethyl-2-oxo ethylcarbamoyl)-1-methyl-ethyl)-carbamic acid tert-butyl ester According to the method outlined in General Procedure A, 137 mg (0.44 mmol of 10B and 167 mg (0.44 mmol) of 1E were coupled to give a mixture of diastereomers. The residue was purified by silica gel chromatography using an elution gradient 100% methylene chloride to 5% methanol in methylene chloride to give 128 mg of less polar 10C isomer 1 and 63 mg of more polar 10C isomer 2. MS (Cl, NH$_3$) 674 (MH$^+$) for both isomers D. 2-Amino-N-{2-(3a-(R)-benzyl-3-oxo-2-(2,2,2-trifluoro-ethyl)-2,3,3a,4,6,7-hexahydro-pyrazolo[4,3-c]pyridin-5-yl]-1-(R)-benzyloxymethyl-2-oxo-ethyl}-isobutyramide hydrochloride To 120 mg (0.18 mmol of 10C isomer 1 in 3.5 mL of ethanol was added 1.5 mL of concentrated HCl and the mixture was stirred at room temperature for about 2 h. The mixture was concentrated to give 94 mg of 10D isomer 1 as an off-white powder. MS (Cl, NH$_3$) 574 (MH$^+$). $^1$HNMR (CD$_3$OD): (partial) δ 7.31 (m, 5H), 7.18 (m, 5H), 5.21 (m, 1H), 4.57 (m, 3H), 4.26 (m, 1H), 4.08 (m, 1H), 3.79 (m, 2H), 3.09 (m, 4H), 2.65 (m, 2H), 1.63 (m, 6H).

E. 2-Amino-N-{2-[3a-(S)-benzyl-3-oxo-2-(2,2,2-trifluoro-ethyl)-2,3,3a,4,6,7-hexahydro-pyrazolo[4,3-c]pyridin-5-yl]-1-(R)-benzyloxymethyl-2-oxo-ethyl}-isobutyramide hydrochloride To 53 mg (0.079 mmol) of 10C isomer 2 in 3.5 mL of ethanol was added 1.5 mL of concentrated HCl and the mixture was stirred at room temperature for about 2 h. The mixture was concentrated to give 41 mg of 10E isomer 2 as a light yellow solid. MS (Cl, NH$_3$) 574 (MH$^+$). $^1$HNMR (CD$_3$OD): (partial) δ 7.33 (m, 5H), 7.15 (m, 4H), 6.81 (m, 1H), 5.30 (m, 1H), 4.67 (m, 4H), 4.15 (m, 2H), 3.77 (m, 2H), 3.09 (m, 3H), 2.64 (m, 3H), 1.58 (m, 6H).

EXAMPLE 11

2-Amino-N-[2-(3a-(R)-benzyl-2-tert-butyl-3-oxo-2,3,3a,4,6,7-hexahydro-pyrazolo[4,3-c]pyridin-5-yl)-1-(R)- benzyloxymethyl-2-oxo-ethyl]-isobutyramide methanesulfonate and 2-Amino-N-[2-(3a-(S)-benzyl-2-tert-butyl-3-oxo-2,3,3a,4,6,7-hexahydro pyrazolo[4,3-c]pyridin-5-yl)-1-(R)-benzyloxymethyl-2-oxo-ethyl]-isobutyramide methanesulfonate A. 3a-(R,S)-Benzyl-2-tert-butyl-3-oxo-2,3,3a,4,6,7-hexahydro-pyrazolo[4,3-c]pyridine-5-carboxylic acid tert-butyl ester To 2.07 g (5.95 mmol) of 14B in 40 mL of ethanol was added 0.97 g (7.7 mmol) of tert-butylhydrazine hydrochloride and 0.63 g (7.7 mmol) of sodium acetate and the mixture was heated at about 70° C. for about 17 h. The mixture was cooled and the solution decanted from the precipitate and concentrated. The residue was dissolved in 80 mL of toluene and heated at reflux for about 6 h. The mixture was concentrated and the residue was purified by silica gel chromatography (9:1 v/v hexane:ethyl acetate) to give 1.7 g of 11A MS (Cl, NH$_3$) 386 (MH$^+$).

B. 3a-(R,S)-Benzyl-2-tert-butyl-2,3a,4,5,6,7-hexahydro-pyrazolo[4,3-c]pyridin-3-one To 535 mg (1.39 mmol) of 11A in 20 mL of methylene chloride was added 225 µL of methanesulfonic acid and the mixture was stirred for about 1.5 h at room temperature. The mixture was diluted with ethyl acetate and washed twice with 1 N NaOH and once with brine, dried over Na$_2$SO$_4$ and concentrated to give 246 mg of 11B. MS (Cl, NH$_3$) 286 (MH$^+$).

C. {1-[2-(3a-(R,S)-Benzyl-2-tert-butyl-3-oxo-2,3,3a,4,6,7-hexahydro-pyrazolo[4,3-c]pyridin-5-yl)-1-(R)-benzyloxymethyl-2-oxo-ethylcarbamoyl]-1-methyl-ethyl}-carbamic acid tert-butyl ester According to the method outlined in General Procedure A, 246 mg (0.86 mmol) of 11B and 328 mg of 14F were coupled to give a mixture of diastereomers. The residue was purified by silica gel chromatography (6:4 v/v hexane/ethyl acetate) to give 250 mg of less polar 11C isomer 1 and 90 mg more polar 11C isomer 2. MS (Cl, NH$_3$) 648 (MH$^+$) for both isomers.

D. 2-Amino-N-[2-(3a-(R)-benzyl-2-tert-butyl-3-oxo-2,3,3a,4,6,7-hexahydro-pyrazolo[4,3-c]pyridin-5-yl)1-(R)-benzyloxymethyl-2-oxo-ethyl]-isobutyramide methanesulfonate To 210 mg (0.32 mmol) of 11C isomer 1 in 15 mL of methylene chloride at about 0° C. was added 28 µL (0.44 mmol) of methanesulfonic acid. The ice bath was removed and the mixture was stirred for about 3 h, diluted with 15 mL of diethyl ether and the precipitated solid was collected by filtration to give 100 mg of 11D isomer 1. MS (Cl, NH$_3$) 548 (MH$^+$). $^1$H NMR (CD$_3$OD): (partial) δ 7.33 (m, 5H), 7.27–7.07 (m, 5H), 5.21 (m, 1H), 4.54 (m, 3H), 3.86 (m, 3H), 3.10 (m, 4H), 2.61 (s, 3H), 1.62 (m, 6H), 1.18 (s, 9H).

E. 2-Amino-N-[2-(3a-(S)-benzyl-2-tert-butyl-3-oxo-2,3,3a,4,6,7-hexahydro-pyrazolo[4,3-c]pyridin-5-yl)-1-(R)-benzyloxymethyl-2-oxo-ethyl]-isobutyramide methanesulfonate To 85 mg (0.13 mmol) of 11C isomer 2 in 10 mL of methylene chloride at about 0° C. was added 21 µL (0.32 mmol) of methanesulfonic add. The ice bath was removed and the mixture was stirred for about 3 h, diluted with 20 mL of diethyl ether and the precipitated solid was collected by filtration to give 46 mg of 11E isomer 2. MS (Cl, NH$_3$) 548 (MH$^+$). $^1$H NMR (CD$_3$OD): (partial) δ 8.28 (br d, 1H), 7.32 (m, 5 K), 7.1B (m, 4H), 6.84 (m, 1H), 5.31 (m, 1H), 4.60 (m, 3H), 3.70 (m, 3H), 3.18–2.92 (m, 3H), 2.68 (s, 3H), 1.57 (m, 6H), 1.13 (s, 9H).

EXAMPLE 12

2-Amino-N-[1-(R)-(1H-indol-3-ylmethy)-2-(2-methyl-3-oxo-3a-(R,S)-pyridin-2-ylmethyl-2,3,3A,4,6,7-hexahydro-pyrazolo[4,3-c]pyridin-5-yl)-oxo-ethyl]-isobutyramide dihydrochloride A. 4-Oxo-3-(R,S)-pyridin-2-ylmethyl-piperidine-1,3-dicarboxylic acid 1-tert-butyl ester 3-methyl ester To a solution of 2.00 g (7.8 mmol) of 3A in 32 mL of THF was added 468 mg (11.7 mmol) of sodium hydride (60% oil dispersion) at about 0° C. and the mixture was stirred for about 30 min. A solution of 762 mg (6.0 mmol) 2-picolyl chloride in 5 mL of THF was added to the stirring solution over about 5 min., followed by the addition of 432 mg (2.6 mmol) of potassium iodide. The ice bath was removed and the mixture was heated for about 17 h at reflux. The mixture was diluted with ethyl acetate and washed once with water and once with brine, dried over MgSO$_4$, and concentrated. The residue was purified by silica gel chromatography using (6:4 v/v ether:hexane) followed by (6:4 v/v ethyl acetate:hexane) to give 1.2 g of 12A. MS (Cl, NH$_3$) 349 (MH$^+$).

B. 2-Methyl-3-oxo-3a-(R,S)-pyridin-2-ylmethyl-2,3,3a,4,6,7-hexahydro-pyrazolo[4,3-c]pyridine-5-carboxylic acid tert-butyl ester A mixture of 1.20 g (3.45 mmol) of 12A and 159 mg (3.45 mmol) of methylhydrazine in 20 mL of ethanol was heated at reflux for about 6.5 h. The mixture was concentrated and the residue was dissolved in 25 mL toluene and heated at reflux for about 17 h. The mixture was concentrated and the residue was purified by silica gel chromatography (65:35 v/v ethyl acetate:hexane) to give 450 mg of 12B. MS (Cl, NH$_3$) 345 (MH$^+$).

C. 2-Methyl-3a-(R,S)-pyridin-2-ylmethyl-2,3a,4,5,6,7-hexahydro-pyrazolo[4,3-c]pyridin-3-one dihydrochloride A mixture of 450 mg (1.30 mmol) of 12B in 2 mL of 4M HCl/dioxane was stirred at room temperature for about 4.5 h. The mixture was concentrated to give 450 mg of 12C. MS (Cl, NH$_3$) 245 (MH$^+$).

D. {1-[(1-(R)-H-indol-3-ylmethyl)-2-(2-methyl-3-oxo-3a-(R,S)-pyridin-2-ylmethyl-2,3,3a,4,6,7-hexahydro-pyrolo[4,3-c]pyridin-5-yl)-2-oxo-ethylcarbamoyl]1-methyl-ethyl}-carbamic acid tert-butyl ester According to General Procedure A, 108 mg (0.31 mmol) of 12C and 122 mg (0.31 mmol) of 2C were coupled and the residue was purified by silica gel chromatography (95:5 v/v ethyl acetate:methanol) to give 118 mg of 12D. MS (Cl, NH$_3$) 616 (MH$^+$).

E. 2-Amino-N-[1-(R)-(1H-indol-3-ylmethyl)-2-(2-methyl-3-oxo-3a-(R,S)-pyridin-2-ylmethyl-2,3,3a,4,6,7-hexahydro-pyrazolo[4,3-c]pyridin-5-yl)-2-oxo-ethyl]-isobutyramide dihydrochloride A mixture of 110 mg (0.18 mmol) of 12D in 1 mL of 4M HCl/dioxane was stirred at room temperature for 17 h. The mixture was concentrated to give 51 mg of 12E. MS (Cl, NH$_3$) 516 (MH$^+$). $^1$HNMR (CD$_3$OD): (partial) δ 8.91–8.52 (m, 2H), 8.04 (m, 2H), 7.76–7.50 (m, 3H), 6.82 (m, 1H), 4.62 (m, 1H), 3.36 (s, 3H), 1.63 (s, 6H).

EXAMPLE 13

2-Amino-N-[1-(R)-benzyloxymethyl-2-(2-methyl-3-oxo-3a-(R,S)-pyridin-2-ylmethyl-2,3,3a,4,6,7-hexahydro-pyrazolo[4,3-c]pyridin-5-yl)-2-oxo-ethyl]-isobutyramide dihydrochloride A. {1-[1-(R)-Benzyloxyrmethyl-2-(2-methyl-3-oxo-3a-(R,S)-pyridin-2-ylmethyl-2,3,3a,4,6,7-hexahydro-pyrazolo[4,3-c]pyridin-5-yl)-2-oxo-ethylcarbamoyl]-1-methyl-ethyl}-carbamic acid tert-butyl ester According to General Procedure A, 86 mg (0.27 mmol) of 12C and 103 mg (0.27 mmol) of 1E were coupled and the residue was purified by silica gel chromatography (95:5 v/v ethyl acetate:hexane) to give 82 mg of 13A.

B. 2-Amino-N-[1-(R)-benzyloxymethyl-2-(2-methyl-3-oxo-3a-(R,S)-pyridin-2-ylmethyl-2,3,3a,4,6,7-hexahydro-pyrazolo[4,3-c]pyridin-5-yl)-2-oxo-ethyl]-isobutyramide dihydrochloride A mixture of 75 mg (0.12 mmol) of 13A in 1 mL of 4M HCl/dioxane was stirred at room temperature for about 17 h. The mixture was concentrated to give 80 mg of 13B. MS (Cl, NH$_3$) 507 (MH$^+$). $^1$HNMR (CD$_3$OD): (partial) δ 8.78 (m, 1H), 8.46 (m, 1H), 8.13–7.82 (m, 2H), 7.32 (m, 5H), 4.57 (m, 3H), 3.96 (m, 1H), 3.82 (m, 2H), 1.63 (m, 6H).

EXAMPLE 14

2-Amino-N-[2-(3a-(R)-benzyl-2-methyl-3-oxo-2,3,3a,4,6,7-hexahydro-pyrazolo[4,3-c]pyridin-5-yl)-1-(R)-(benzyloxymethyl)-2-oxo-ethyl]-isobutyramide A. 4-Oxo-piperidine-1,3-dicarboxylic acid 1-tert-butyl ester 3-methyl ester To a mixture of 100.0 g (516.4 mmol) of 4-oxo-piperidine-3-carboxylic acid methyl ester and 63 g (516.4 mmol) of 4,4-dimethylaminopyridine in 1 L of methylene chloride at about 0° C. was added a solution of 113.0 g (516.4 mmol) of di-tert-butyldicarbonate in 100 mL of methylene chloride over about 90 min. The mixture was slowly warmed to room temperature and then stirred for about 19 h. The mixture was washed three times each with 10% aqueous HCl, saturated aqueous sodium bicarbonate solution and brine, dried over MgSO$_4$ and concentrated to give 130.5 g of 14A as an amorphous solid. $^1$HNMR (CDCl$_3$): δ 4.03 (br, 2H); 3.74 (s, 3H), 3.56 (t, 2H), 2.38 (t, 2H), 1.42 (s, 9H).

B. 3-(R)-Benzyl-4-oxo-piperidine-1,3-dicarboxylic acid 1-tert-butyl ester 3-methyl ester To a stirred suspension of 11.7 g (293 mmol) of sodium hydride (60% oil dispersion washed twice with 100 mL of hexane) in 100 mL of DMF was added a solution of 65.4 g (254 mmol) of 14A in 150 mL of DMF at about 0° C. over about 45 min. The ice bath was removed and the mixture was stirred at room temperature for about 45 min. The mixture was recooled to about 0° C. and 35.2 mL (296 mmol) of benzylbromide in 200 mL of DMF was added dropwise to the stirring solution and the mixture was stirred for about 23 h at room temperature. To the solution was carefully added 550 mL of water and the mixture was stirred for about 30 min. The mixture was extracted three times with ethyl acetate and the combined organic extracts were washed five times with water, once with brine, dried over MgSO$_4$ and concentrated to give 98 g of a yellow oil. The oil was crystallized from hexane to give 71 g of 14B as a white solid. MS (Cl, NH$_3$) 348 (MH$^+$). $^1$HNMR (CDCl$_3$): (partial) δ 7.23 (m, 3H), 7.13 (m, 2H), 4.58 (br m, 1H), 4.18 (br, 1H), 3.63 (s, 3H), 3.28–2.96 (m, 4H), 2.72 (m, 1H), 2.43 (m, 1H), 1.44 (s, 9H).

C. 3a-(R)-Benzyl-2-methyl-3-oxo-2,3,3a,4,6,7-hexahydro-pyrazolo[4,3-c]pyridine-5-carboxylic acid tert-butyl ester A mixture of 47.0 g (135 mmol) of 14B, 38.9 g (270 mmol) of methylhydrazine sulfate and 44.3 g (540 mmol) of sodium acetate in 900 mL of ethanol was heated at reflux for about 17 h under nitrogen. The mixture was concentrated and the residue was dissolved in ethyl acetate and washed three times with water and once with brine, dried over MgSO$_4$ and concentrated to give a yellow oil. The oil was stirred in 750 mL of hexane for about 3 h to give 41.17 g of 14C as a white solid. MS (Cl, NH$_3$) 344 (MH$^+$). $^1$H NMR (CDCl$_3$): (partial)δ 7.19 (m, 3H), 7.05 (m, 2H), 4.61 (br m, 2H), 3.24 (m, 1H), 3.09 (s, 3H), 3.01 (m, 1H), 2.62 (m, 4H), 1.52 (s, 9H).

D. 3a-(R,S)-Benzyl-2-methyl-2,3a,4,5,6,7-hexahydro-pyrazolo[4,3-c]pyridin-5-one hydrochloride Anhydrous HCl was bubbled through a solution of 24.55 g (71.5 mmol) of 14C in 800 mL of diethyl ether at about 0° C. for about 12-min. The mixture was stirred for about 3 h, during which time a white precipitate formed. The precipitated solid was collected by filtration and to give 19.2 g of 14D. MS (Cl, NH$_3$) 244 (MH$^+$). $^1$HNMR (CD$_3$OD): (partial) δ 7.25 (m, 3H), 7.05 (m, 2H), 3.77 (m, 2H), 3.51 (d, 1H), 3.25 (m, 1H), 3.17 (m, 3H), 3.03 (s, 3H), 2.81 (m, 1H).

E. 2-tert-Butoxycarbonylamino-2-methyl-propionic acid 2,5-dioxo-pyrrolidin-1-yl ester To a stirring solution of 100.0 g (492 mmol) of Boca-methylalanine and 94.0 g (492 mmol) of EDC in 2 L of methylene chloride at about 0° C. was added 56.63 g (492 mmol) of N-hydroxysuccinimide in portions and the reaction was then allowed to warm to room temperature. The mixture was stirred for about 24 h and washed twice each with saturated aqueous sodium bicarbonate solution and brine, dried over Na$_2$SO$_4$ and concentrated to give 124.0 g of 14E as a white solid. $^1$HNMR (CDCl$_3$): δ 4.96 (br, 1H), 2.82 (s, 4H), 1.66 (s, 6H), 1.48 (s, 9H).

F. 3-(R)-Benzyloxy-2-(2-tert-butoxycarbonylamino-2-methyl-propionylamino)-propionic acid A mixture of 50.5 g (168 mmol) of 14E, 33.5 g (168 mmol) of O-benzyl-D-serine, and 51.05 g (505 mmol) of triethylamine in 400 mL of dioxane and 100 mL of water was heated at about 45° C. for about 16 h. The mixture was diluted with ethyl acetate and acidified to pH 2 with acetic add. The layers were separated and the organic phase was washed with brine, dried over Na$_2$SO$_4$ and concentrated to give 650 g of 14F as a white solid. $^1$HNMR (CD$_3$OD): (partial) a 7.55 (d, 1H), 7.29 (m, 5H). 4.52 (m, 1H), 4.48 (s, 2H), 3.84 (d of d, 1H), 3.69 (d of d, 1H), 1.42 (s, 6H), 1.38 (s, 9H).

G. 3a-(R)-Benzyl-2-methyl-2,3a,4,5,6,7-hexahydro-pyrazolo[4,3-c]pyridin-3-one L-tartrate To a mixture of 5.00 g (20.6 mmol) of the free base of 14D and 3.09 g (20.6 mmol) of L-tartaric acid in 80 mL of acetone and 3.2 mL of water was heated under nitrogen at about 70° C. for about 70 h, during which time the reaction mixture became a thick suspension and an additional 20 mL of acetone was added. The reaction mixture was cooled slowly to room temperature and then filtered. The solid that was collected was washed with acetone and dried under vacuum to give 7.03 g of 14G as a white solid.

H. 3a-(R)-Benzyl-2-methyl-2,3a,4,5,6,7-hexahydro-pyrazolo[4,3-c]pyridin-3-one

To a suspension of 5.00 g (12.7 mmol) of 14G in 80 mL of methylene chloride at about 0° C. was added 1.72 mL (25.4 mmol) of ammonium hydroxide and th mixture was stirred for about 15 min. The cold solution was filtered and used immediately in the next step.

I. {1-[2-(3a-(R)-Benzyl-2-methyl-3-oxo-2,3,3a,4,6,7-hexahydro-pyrazolo[4,3-c]pyridin-5-yl)-1-(R)-(benzyloxymethyl)-2-oxo-ethylcarbamoyl]-1-methyl-ethyl}-carbamic acid tert-butyl ester A mixture of 4.83 g (12.7 mmol)of 14F, the solution from 14H, 2.60 g (19.1 mmol) of HOAT, and 2.45 g (12.8 mmol) of EDC was stirred at about 0° C. under nitrogen for about 1 h and then warmed to room temperature and stirred for about 16 h. The mixture was filtered and the filtrate was washed with saturated aqueous sodium bicarbonate and water, dried over MgSO$_4$ and concentrated to give 7.35 g of 141 as a white solid.

J. 2-Amino-N-[2-(3a-(R)-benzyl-2-methyl-3-oxo-2,3,3a,4,6,7-hexahydro-pyrazolo[4,3-c]pyridin-5-yl)-1-(R)-(benzyloxymethyl)-2-oxo-ethyl]isobutyramide To 755 mg (1.25 mmol) of 14I in 7 mL of methylene chloride at about 0° C. was added 3.5 mL of cold trifluoroacetic acid and the mixture was stirred for about 1 h at about 0° C. The mixture was allowed to warm to room temperature and stirred for about 2 h. The mixture was concentrated and co-evaporated twice with toluene. The residue was dissolved in chloroform and washed twice with saturated aqueous sodium bicarbonate and once each with water and brine. The mixture was dried over $MgSO_4$ and concentrated to give 594 mg of 14J as an oil.

EXAMPLE 15

2-Amino-N-[1-(R)-benzyloxymethyl-2-(2-methyl-3-oxo-2, 3,3a,4,6,7-hexahydro-pyrazolo[4,3-c]pyridin-5-yl)-2-oxo-ethyl]-isobutyramide hydrochloride A. 2-Methyl-3-oxo-2,3,3a,4,6,7-hexahydro-pyrazolo[4,3-c]pyridine-5-carboxylic acid tert-butyl ester A mixture of 3.00 g (11.66 mmol) of 3A and 537 mg (11.66 mmol) of methylhydrazine in 100 mL of ethanol was heated at reflux for about 17 h. Th mixture was concentrated and the residue was dissolved in 100 mL toluene and heated at reflux for about 17 h. The mixture was diluted with ethyl acetate, and washed twice with brine, dried over $MgSO_4$ and concentrated. The residue was purified by silica gel chromatography using an elution gradient of 100% ethyl acetate to 5% methanol in methylene chloride to give 2.28 g of 15A as a white solid. $^1$HNMR ($CD_3OD$): δ 4.20 (s, 2H), 3.67 (t, 2H), 3.43 (s, 3H), 2.58 (t, 2H), 1.48 (s, 9H).

B. 2-Methyl-2,3a,4,5,6,7-hexahydro-pyrazolo[4,3-c]pyridin-3-one hydrochloride

To 510 mg (2.01 mmol) of 15A in 30 mL of ethanol was added 10 mL of concentrated HCl and the mixture was stirred at room temperature for about 35 min. The mixture was concentrated and the residue was crystallized from methanol/ethyl acetate to give 425 mg of 15B as a yellow solid. $^1$HNMR ($CD_3OD$): δ 4.27 (S, 2H), 3.71 (S. 3H), 3.56 (T. 2H), 3.05 (T, 2H).

C. {1-[1-(R)-Benzyloxymethyl-2-(2-methyl-3-oxo-2,3,3a,4,6,7-hexahydro-pyrazolo[4,3-c]pyridin-5-yl)-2-oxo-ethylcarbamoyl]-1-methyl-ethyl}-carbamic acid tert-butyl ester According to the method outlined in General Procedure A. 100 mg (0.53 mmol) of 15 B and 202 mg (0.53 mmol of 1E were coupled and the residue was purified by silica gel chromatography (95:5 v/v methylene chloride:methanol) to give 54 mg of 15C as a white solid. MS (Cl, $NH_3$) 516 ($MH^+$).

D. 2-Amino-N-[1-R-benzyloxymethyl-2-(2-methyl-3-oxo-2,3,3a,4,6,7-hexahydro-pyrazolo[4,3-c]pyridin-5-yl)-2-oxo-ethyl]-isobutyramide hydrochloride To 54 mg (0.10 mmol) of 15C in 30 mL of ethanol was added 10 mL of concentrated HCl and the mixture was stirred at room temperature for about 40 min. The mixture was concentrated and the residue was precipitated from methanol/ethyl acetate to give 50 mg of 15D. MS (Cl, $NH_3$) 416 ($MH^+$). $^1$HNMR ($CD_3OD$): (partial) δ 7.28 (m, 5H), 5.18 (m, 1 H), 4.69–4.38 (m, 4H), 3.88 (m, 1H), 3.73 (m, 2H), 3.68 (s, 2H), 3.61 (m, 1H), 2.67 (m, 1H), 1.57 (s, 6H).

EXAMPLE 16

2-Amino-N-[2-(2-benzyl-3-oxo-2,3,3a,4,6,7-hexahydro-pyrazolo[4,3-c]pyridin-5-yl)-1(R)-(1H-indol-3-ylmethyl)-2-oxo-ethyl]-isobutyramide hydrochloride A. 2-Benzyl-3-oxo-2,3,3a,4,67-hexahydro-pyrazolo[4,3-c]pyridine-5-carboxylic acid tert-butyl ester A mixture of 800 mg (3.11 mmol) of 3A and 495 mg (3.11 mmol) of benzyl-hydrazine dihydrochloride in 15 mL of ethanol was heated at reflux for about 17 h. The mixture was concentrated and the residue was dissolved in 100 mL toluene and heated at reflux for about 48 h. The mixture was diluted with ethyl acetate, and washed twice with brine, dried over $Na_2SO_4$ and concentrated. The residue was purified by silica gel chromatography using an elution gradient of 100% ethyl acetate to 5% methanol in methylene chloride to give 530 mg of 16A as a tan solid. MS (Cl, $NH_3$) 330 ($MH^+$).

B. 2-Benzyl-2,3a,4,5,6,7-hexahydro-pyrazolo[4,3-c]pyridin-3-one hydrochloride

To 411 mg (1.24 mmol) of 16A in 30 mL of ethanol was added 10 mL of concentrated HCl and the mixture was stirred at room temperature for about 30 min. The mixture was concentrated and the residue was crystallized from methanol/ethyl acetate to give 353 mg of 16B as a yellow solid. MS (Cl, $NH_3$) 230 ($MH^+$). $^1$HNMR ($CD_3OD$): δ 7.26–7.40 (m, 5H), 5.22 (s, 2H), 4.12 (s, 2H), 3.53 (t, 2H), 3.00 (t, 2H).

C. (R)-2-(2-tert-Butoxycarbonylamino-2-methyl-propionylamino)-3-(1H-indol-3-yl)-propionic acid To a stirring solution of 30.6 g (0.15 mol) of D-tryptophan, 30.4 g (0.30 mol) of N-methylmorpholine in 450 mL of (4:1) dioxane:water, was added 45.0 g (0.15 mol) of 14E and the mixture was stirred for about 72 h. Excess dioxane was removed by evaporation and water and ethyl acetate were added to the mixture. The pH of the solution was adjusted to 3 with concentrated HCl and the layers were separated. The organic layer was washed with water and brine, dried over $MgSO_4$ and concentrated. The residue was crystallized from ethyl acetate/hexanes to give 37.0 g of an off-white solid.

D. {1-[2-(2-Benzyl-3-oxo-2,3,3a,4,6,7-hexahydro-pyrazolo[4,3-c]pyridin-5-yl)-1-(R)-(1H-indol-3-ylmethyl)-2-oxo-ethylcarbamoyl]-1-methyl-ethyl}-carbamic acid tert-butyl ester According to the method outlined in General Procedure A, 100 mg (0.38 mmol) of 16B and 202 mg (0.53 mmol) of 16C were coupled and the residue was purified by silica gel chromatography (95:5 v/v methylene chloride:methanol) to give 45 mg of 16D as a white solid. MS (Cl, $NH_3$) 601 ($MH^+$).

E. 2-Amino-N-[2-(2-benzyl-3-oxo-2,3,3a,4,6,7-hexahydro-pyrazolo[4,3-c]pyridin-5-yl)-1-(R)-(1H-indol-3-ylmethyl)-2-oxo-ethyl]-isobutyramide hydrochloride To 45 mg (0.07 mmol) of 16D in 60 mL of ethanol was added 20 mL of concentrated HCl and the mixture was stirred at room temperature for 35 min. The mixture was concentrated and the residue was precipitated from methanol/ethyl acetate to give 30 mg of 16E. $^1$HNMR ($CD_3OD$): (partial) δ 7.40 (m, 4H), 7.25 (m, 3H), 7.11 (m, 2H), 6.96 (m, 2H), 6.81 (m, 1H), 5.38–4.93 (m, 3H), 4.46 (m, 1H), 4.22 (m, 1H), 3.96 (m, 1H), 3.69 (m, 1H), 3.18 (m, 1H), 2.28 (m, 1H), 1.57 (m, 6H),1.38 (m, 1H).

EXAMPLE 17

2-Amino-N-[1-benzyloxymethyl-2-(2,3a-dimethyl-3-oxo-2,3,3a,4,6,7-hexahydro-pyrazolo[4,3-c]pyridin-5-yl)-2-oxo-ethyl]-isobutyramide hydrochloride A. 3-Methyl-4-oxo-piperidine-1,3-dicarboxylic acid 1-tert-butyl ester 3-(R,S)-methyl ester To a solution of 2.00 g (7.77 mmol) 3A in 30 mL of DMF was added 308 mg (7.77 mmol) of sodium hydride (60% oil dispersion) and the mixture was stirred at room temperature for about 25 min. To the stirring solution was added 0.50 mL (7.77 mmol) of methyl iodide and the mixture was stirred for about 17 h at room temperature. The mixture was diluted with ethyl acetate and washed once with water and four times with brine, dried over $MgSO_4$, and concentrated. The residue was purified by silica gel chromatography (7:3 v/v hexane:ethyl acetate) to give 1.75 g of 17A as a clear oil. MS (Cl, NH$_3$) 272 (MH$^+$).

B. 2,3a-(R,S)-Dimethyl-3-oxo-2,3,3a,4,6,7-hexahydro-pyrazolo[4,3-c]pyridine-5-carboxylic acid tert-butyl ester A mixture of 1.62 g (9.50 mmol) of 17A and 435 mg (9.50 mmol) of methylhydrazine in 30 mL of ethanol was heated at reflux for about 4 h. The mixture was concentrated and the residue was dissolved in 50 mL toluene and heated at reflux for about 14 h. The mixture was diluted with ethyl acetate, and washed twice with brine, dried over Na$_2$SO$_4$ and concentrated. The residue was purified by silica gel chromatography (7:3 v/v hexane:ethyl acetate) to give 1.00 g of 17B as a white solid. MS (Cl, NH$_3$) 268 (MH$^+$).

C. 2,3a-(R,S)-Dimethyl-2,3a,4,5,6,7-hexahydro-pyrazolo[4,3-c]pyridin-3-one hydrochloride To 1.00 g (3.74 mmol) of 17B in 40 mL of ethanol was added 8 mL of concentrated HCl and the mixture was stirred at room temperature for about 35 min. The mixture was concentrated and the residue was crystallized from methanol/ethyl acetate to give 850 mg of 17C as a white solid. MS (Cl, NH$_3$) 168 (MH$^+$).

D. {1-[1-(R)-Benzyloxymethyl-2-(2,3a-(R,S)-dimethyl-3-oxo-2,3,3a,4,6,7-hexahydro-pyrazolo[4,3-c]pyridin-5-yl)-2-oxo-ethylcarbamoyl]-1-methyl-ethyl}-carbamic acid tert-butyl ester According to the method outlined in General Procedure A, 150 mg (0.74 mmol) of 17C and 514 mg (1.35 mmol) of 1E were coupled and the residue was purified by silica gel chromatography (85:15 v/v hexane:ethyl acetate) to give 185 mg of 17D as a white solid.

E. 2-Amino-N-[1-(R)-benzyloxymethyl-2-(2,3a-(R,S)-dimethyl-3-oxo-2,3,3a,4,6,7-hexahydro-pyrazolo[4,3-c]pyridin-5-yl)-2-oxo-ethyl]isobutyramide hydrochloride To 173 mg (0.33 mmol) of 17B in 40 mL of ethanol was added 15 mL of concentrated HCl and the mixture was stirred at room temperature for about 1 h. The mixture was concentrated and the residue was diluted with chloroform and washed with saturated aqueous sodium bicarbonate and brine, dried over Na$_2$SO$_4$ and the residue was purified by silica gel chromatography using an elution gradient of 100% ethyl acetate to 10% diethylamine in ethyl acetate. The residue was dissolved in ethanol and acidified with aqueous HCl. The mixture was concentrated and the residue was crystallized from methanol/ethyl acetate to give 65 mg of 17E as a white solid. MS (Cl, NH$_3$) 502 (MH$^+$). $^1$HNMR (CD$_3$OD): (partial) δ 7.32 (m, 5H), 5.14 (m, 1H), 4.53 (m, 3H), 3.71 (m, 3H), 2.97 (m, 1H), 2.83 (m, 1H); 2.57 (m, 1H), 1.98 (m, 2H), 1.61 (m, 6H), 1.38 (s, 3H).

EXAMPLE 18

2-Amino-N-[2-(3a-(R)-benzyl-3-oxo-2,3,3a,4,6,7-hexahydro-pyrazolo[4,3-c]pyridin-5-yl)-1-(R)-benzyloxymethyl-2-oxo-ethyl]-isobutyramide hydrochloride and 2-Amino-N-[2-(3a-(S)-benzyl-3-oxo-2,3,3a,4,6,7-hexahydro-pyrazolo[4,3-c]pyridin-5-yl)-1-(R)-benzyloxymethyl-2-oxo-ethyl]isobutyramide hydrochloride A. 3-Benzyl-4-oxo-piperidine-3-carboxylic acid methyl ester To 200 mg (0.58 mmol) of 36 at about 0° C. was added 5 mL of cold trifluoroacetic acid and the mixture was stirred for about 1 h. The mixture was concentrated and the residue was co-evaporated with ethyl acetate and hexane. To the residue was added 2N NaOH to make it basic and the mixture was extracted with chloroform. The combined organic extracts were dried over MgSO$_4$ and concentrated to give 18A in quantitative yield.

B. 3-(R,S)-Benzyl-1-[3-benzyloxy-2-(R)-(2-tert-butoxycarbonylamino-2-methyl-propionylamino)-propionyl]-4-oxo-piperidine-3-carboxylic acid methyl ester According to the method outlined in General Procedure A, 1.77 g (7.16 mmol) of 18A and 3.04 g (8.0 mmol) of 14F were coupled to give a mixture of diastereomers. The residue was purified by silica gel chromatography (7:3 v/v hexane:ethyl acetate) to give 820 mg of less polar 18B isomer 1 and 1.14 g more polar 18B isomer 2. MS (Cl, NH$_3$) 611 (MH$^+$) for both isomers.

C. {1-[2-(3a-(R,S)-Benzyl-3-oxo-2,3,3a,4,6,7-hexahydro-pyrazolo[4,3-c]pyridin-5-yl)-1-(R)-benzyloxymethyl-2-oxo-ethylcarbamoyl}-1methyl-ethyl-]-carbamic acid tert-butyl ester To a solution of 820 mg (1.32 mmol) of 18B isomer 1 in 13 mL of ethanol was added 342 mg (2.63 mmol) of hydrazine sulfate and 431 mg (5.26 mmol) of sodium acetate and the mixture was heated at reflux for about 17 h. The mixture was concentrated and the residue was diluted with ethyl acetate and washed with saturated aqueous sodium bicarbonate and brine, dried over MgSO$_4$ and concentrated. The residue was purified by silica gel chromatography using an elution gradient of 75% ethyl acetate in hexane to 100% ethyl acetate to give 550 mg of 18C isomer 1.

To a solution of 1.14 g (1.86 mmol) of 18B isomer 2 in 20 mL of ethanol was added 485 mg (3.73 mmol) of hydrazine sulfate and 613 mg (7.48 mmol) of sodium acetate and the mixture was heated at reflux for about 17 h. The mixture was concentrated and the residue was diluted with ethyl acetate and washed with saturated aqueous sodium bicarbonate and brine, dried over MgSO$_4$ and concentrated. The residue was purified by silica gel chromatography (75:25 v/v ethyl acetate/hexane) to give 710 mg of 18C isomer s D. 2-Amino-N-[2-(3a-(R)-benzyl 3-oxo-2,3,3a,4,6,7-hexahydro-pyrazolo[4,3-c]pyridin-5-yl)-1-(R)-benzyloxymethyl-2-oxo-ethyl]-isobutyramide hydrochloride To 200 mg (0.34 mmol) of 18C isomer 1 in 12 mL of ethanol was added 6 mL of concentrated HCl and the mixture was stirred at room temperature for about 2.5 h. The mixture was concentrated and co-evaporated three times with ethanol to give 20 mg of 18D isomer 1. MS (Cl, NH$_3$) 492 (MH$^+$). $^1$HNMR (CD$_3$OD): (partial)δ 8.42 (br d, 1H). 7.35 (m, 5H), 7.18 (m, 5H), 5.23 (m, 2H), 4.91 (m, 1H), 4.54 (m, 4H), 3.80 (m, 2H), 3.63 (m, 1H), 3.12 (m, 1H), 3.07 (m, 3H), 2.61 (m, 3H), 1.62 (m, 6H), 1.39 (m, 1H).

E. 2-Amino-N-[2(3a-(S)-benzyl-3-oxo-2,3,3a,4,67-hexahydro-pyrazolo[4,3-c]pyridin-5-yl)-1-(R)-benzyloxymethyl-2-oxo-ethyl]-isobutyramide hydrochloride To 200 mg (0.34 mmol) of 18C isomer 2 in 20 mL of ethanol was added 10 mL of concentrated HCl and the mixture was stirred at room temperature for about 2.5 h. The mixture was concentrated and coevaporated three times with ethanol to give 30 mg of 18E isomer 2. MS (Cl, NH$_3$) 492 (MH$^+$). $^1$HNMR (CD$_{300}$): (partial) δ 8.29 (br d, 1H), 7.30 (m, 5H), 7.11 (m, 4H), 6.88 (m, 1H), 5.29 (m, 1H), 4.92 (m, 1H), 4.62 (m, 3H), 3.91–3.70 (m, 3H), 3.22–2.95 (m, 3H), 2.66 (m, 3H), 1.57 (m, 6H), 1.30 (m, 1H), 0.89 (m, 1H).

EXAMPLE 19

2-Amino-N-[1-(R)-benzyloxymethyl-2-(2-methyl-3-oxo-3a-(R,S)-thiazol-4-ylmethyl-2,3,3a,4,6,7-hexahydro-pyrazolo[4,3-c]pyridin-5-yl)-2-oxo-ethyl]-isobutyramide dihydrochloride A. 4-Oxo-3-(R,S)-thiazol-4-ylmethyl-piperidine-1,3-dicarboxylic acid 1-tert-butyl ester 3-ethyl ester To a solution of 300 mg (1.10 mmol) of 1A in 5 mL of THF at about 0 °C was added 67 mg (1.66 mmol) of sodium hydride (60% oil dispersion) and the mixture was stirred for about 30 min. A solution of 204 mg (1.21 mmol) of 4-chloromethyl-thiazole (Hsiao, C. N; Synth. Comm. 20, p. 3507 (1990)) in 5 mL of THF was added to the cold solution, followed by 87 mg (0.53 mmol) of potassium iodide and the mixture was heated at reflux for about 17 h. The mixture was diluted with water and extracted with ethyl acetate. The combined organic extracts were dried over $Na_2SO_4$ and concentrated and the residue was purified by silica gel chromatography (7:3 v/v hexane:ethyl acetate) to give 90 mg of the title compound. MS (Cl, $NH_3$) 648 ($MH^+$).

B. 2-M thyl-3-oxo-3a-(R,S)-thiazol-4-ylmethyl-2,3,3a,4,6,7-hexahydro-pyrazolo[4,3-c]pyridine-5-carboxylic acid tert-butyl ester To 90 mg (0.24 mmol) of 19A in 2 mL of ethanol was added 11.2 mg (0.24 mmol) of methylhydrazine and the mixture was heated at reflux for about 17 h. An additional 33.6 mg (0.72 mmol) of methylhydrazine was added and the mixture was heated at reflux for about 7 h. The mixture was concentrated and the residue was dissolved in 3 mL of toluene and heated at reflux for about 17 h. The mixture was concentrated and the residue was purified by silica gel chromatography (6:4 v/v hexane:ethyl acetate) to give 44 mg of 199. MS (Cl, $NH_3$) 648 ($MH^+$).

C. 2-Methyl-3a-(R,S)-thiazol-4-ylmethyl-2,3a,4,5,6,7-hexahydro-pyrazolo[4,3-c]pyridine-3-one dihydrochloride A mixture of 44 mg (0.10 mmol) of 19B in 1 mL of 4M HCl in dioxane was stirred at room temperature for about 4 h. The mixture was concentrated and co-evaporated with methylene chloride to give 40 mg of 19C. MS (Cl, $NH_3$) 251 ($MH^+$).

D. {1-[1-(R)-Benzyloxymethyl-2-(2-methyl-3-oxo-3a-(R,S)-thiazol-4-ylmethyl-2,3,3a,4,6,7-hexahydro-pyrazolo[4,3-c]pyridin-5-yl)-2-oxo-ethylcarbamoyl]-methyl-ethyl}carbamic acid tert-butyl ester According to the method outlined in General Procedure A, 40 mg (0.12 mmol) of 19C and 39 mg (0.12 mmol) of 14F were coupled and the residue was purified by silica gel chromatography (9:1 vN ethyl acetate:hexane) to give 40 mg of 19D. MS (Cl, $NH_3$) 613 ($MH^+$).

E. 2-Amino-N-[1-(R)-benzyloxymethyl-2-(2-methyl-3-oxo-3a-(R,S)-thiazol-4-ylmethyl-2,3,3a,4,6,7-hexahydro-pyrazolo[4,3-c]pyridin-5-yl)-2-oxo-ethyl]isobutyramide dihydrochloride A mixture of 40 mg (0.06 mmol) of 19D in 1 mL of 4M HCl in dioxane was stirred at room temperature for about 5 h. The mixture was concentrated and co evaporated with methylene chloride to give 40 mg of 19E. MS (Cl, $NH_3$) 513 ($MH^+$).

EXAMPLE 20

2-Amino-N-[2-(3a-(R)-benzyl-2-methyl-3-oxo-2,3,3a,4,6,7-hexahydro-pyrazolo[4,3-c]pyridine-5-yl)1-(R)-(benzyloxymethyl)-2-oxo-ethyl]-isobutyramide L-tartaric acid salt To 4.6 g of the title compound of Example 14 in 20 mL of methanol, a solution of 1.36 g of L-tartaric acid in 20 mL of methanol was added at about 0° C. The mixture was warmed to room temperature, stirred for about 40 min. and concentrated in vacuo. The residue was diluted with 220 mL of ethyl acetate, heated at reflux for about 1.5 h, then stirred at about 72° C. for about 18 h. The mixture was cooled to room temperature, and filtered to give 5.78 g of the tide compound as a colorless crystalline solid.

EXAMPLE 21

3-Benzyl-3-methoxycarbonylmethyl-4-oxo-piperidine-1-carboxylic acid tert-butyl ester A. 3-Benzyl-4-oxo-piperidine-1-carboxylic acid tert-butyl ester A mixture of the β-ketoester (4480 mg, 12.9 mmol) and LiCl (1100 mg, 25.8 mmol) was heated in DMF (2.0 mL) at about 120 CC for about 17 h. The reaction mixture was cooled to room temperature and extracted with EtOAc (3×100 mL). The combined extracts were dried and concentrated in vacuo. The crude product was chromatographed on $SiO_2$ using 20% ethyl acetate/hexanes to give 1320 mg of the desired product as a yellow oil. $^1$H NMR (250 MHz. $CDCl_3$): d: 7.4 (m, 5H), 4.2 (m, 1H), 3.4 (m, 1H), 3.3 (dd, 1H), 3.05 (dd, $_1$H), 2.7 (m, 1H), 2.55 (m, 4H), 1.5 (s, 9H); MS (APCI): 190 (M+1–BOC).

B. 3-Benzyl-3-methoxycarbonylmethyl-4-oxo-piperidine-1-carboxylic acid tert-butyl ester A solution of the product from Step A of Example 21 above (1320 mg, 4.56 mmol), pyrrolidine (972 mg, 13 mmol) and p-toluenesulfonic acid (33 mg) in benzene (30 mL) was refluxed through 3 Å molecular sieves for about 17 h. The reaction mixture was cooled to room temperature and concentrated in vacuo. The residue was dissolved in benzene (10 mL) and cooled to about 0° C. Methyl bromoacetate (1530 mg, 10 mmol) was added dropwise. The reaction mixture was slowly allowed to warm to room temperature and then was heated under reflux for about 17 h at which point $H_2O$ (5 mL) was added. After refluxing for about another 2 h, the reaction mixture was cooled to room temperature and extracted with EtOAc (3×100 mL). The combined organic extracts were dried and concentrated in vacuo. The crude residue was chromatographed on $SiO_2$-gel using 15% ethyl acetate/hexanes to give 280 mg of product $^1$H NMR (250 MHz, $CDCl_3$): d 7.35 (m, 5H), 4.5 (m, 1H), 3.8 (s, 3H), 3.4 (dd, 1H), 3.1 (m, 1H), 2.85 (m, 4H), 2.6 (m, 1H), 2.4 (m, 1H), 1.5 (s, 9H); MS (APCI): 362 (M+1).

EXAMPLE 22

6-Oxo-1-phenyl-cyclohexane-1,3-dicarboxylic acid 3-tert-butyl ester 1-methyl ester A solution of diphenylmercury (890 mg, 2.5 mmol) in $CHCl_3$ (4 mL) under $N_2$ was heated to about 40° C. Lead tetraacetate (1110 mg, 2.5 mmol) was added in small portions and the greenish yellow solution was stirred at about 40° C. for about 0.5 h. The β-ketoester (520 mg, 2.0 mmol) was then added, followed by pyridine (0.2 mL, 2.5 mmol). After about 5 h at about 40° C., the reaction mixture was concentrated in vacuo and the residue was dissolved in ether (100 mL) and filtered. The filtrate was washed with $3NH_2SO_4$ (3×), dried and concentrated to give 616 mg of a yellow solid. Flash chromatography over $SiO_2$-gel using 25% ethyl acetate/hexanes provided 368 mg of the desired product. $^1$H NMR (400 MHz, $CDCl_3$): d 7.15 (m, 5H), 4.4 (s, 2H), 3.7 (s, 5H), 2.6 (s, 2H), 1.5 (s, 9H); MS (APCI): 334 (M+1)

EXAMPLE 23

(D)-2-Amino-3-(2,4-dichloro-benzyloxy)-propionic acid hydrochloride

A. (D2-tert-Butoxycarbonylamino-3-(2,4-dichloro-benzyloxy)-propionic acid

To a stirred solution of Boc-D-serine (8.2 g, 40 mmol) in DMF (75 mL) at about 0° C. was added NaH (60% dispersion, 3.2 g, 80 mmol) over about a 10 minute period. The reaction mixture was stirred for about 1.75 h at about 0° C., then about 0.25 h at room temperature. After cooling to about 0° C., a solution of 2,4-dichlorotoluene (5.56 mL 40 mmol) in DMF (5 mL) was added dropwise. The reaction mixture was allowed to warm to about 23° C. and was stirred for about 17 h, then was partitioned between di-isopropylether and 10% HCl. The aqueous solution was extracted with di-isopropyl ether (2×). The combined extracts were washed with saturated aqueous brine, dried and concentrated to give 14.75 g of crude product which was used without further purification. $^1$H NMR (400 MHz, CDCl$_3$): d 7.67.2 (m, 3H), 5.4 (d, 1H). 4.6 (s, 2H), 4.0 (d, 1H), 3.8 (dd, 2H), 1.1 (s, 9H); MS (APCI): 264,266 (M+1, M+2).

B. (D)-2-Amino-3-(2,4-dichloro-benzyloxy)-propionic acid hydrochloride

The product from step A of Example 23 above (14.7 g, 40 mmol) was stirred in 4 M HCl/dioxane (100 mL) for about 17 h. The reaction mixture was concentrated in vacuo to give 12 g of a pale yellow solid (100%). MS (APCI): 265 (M+1).

EXAMPLE 24

Example 24 having the formula shown below,

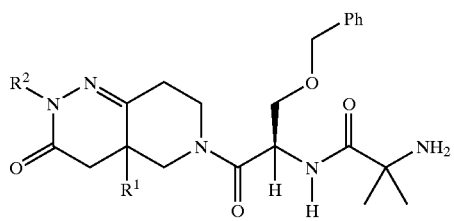

wherein R$^1$ is —CH$_2$-phenyl and R$^2$ is methyl, was synthesized in an analogous manner to the procedures described in Examples 3C to 3F using the title compound of Example 21 as starting material. Both the R,R and S,R diastereomers (* indicates the other stereoisomer center at the C-3 carbon of the above structure) were isolated. Mass spec. (M+1)=520; MS method particle bombardment

EXAMPLES 25 AND 26

Examples 25 and 26 having the formula shown below,

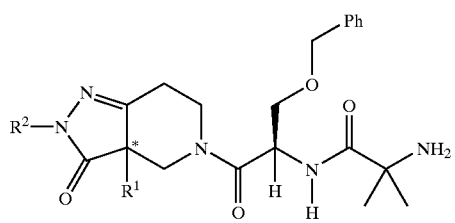

wherein for both examples 25 and 26 R$^1$ is phenyl and R$^2$ is methyl, where example 25 is the R,R isomer and example 26 is the S,R isomer. Examples 25 and 26 were synthesized in an analogous manner to the procedures described in Examples 3C to 3F using the title compound of Example 22 as starting material followed by chromatographic separation of the two separate isomers. Mass sp c. of each example (M+1)=493, MS method≈particle bombardment

EXAMPLES 27–159

Examples 27 to 159 listed in the table below, were prepared according to the scheme illustrated below by coupling the appropriately substituted pyrazalone-piperidine of formula I (in the below scheme) with the (D)OBnSer derivative II (On the below scheme) in an analogous manner to the procedures described in Examples 3E and 3F.

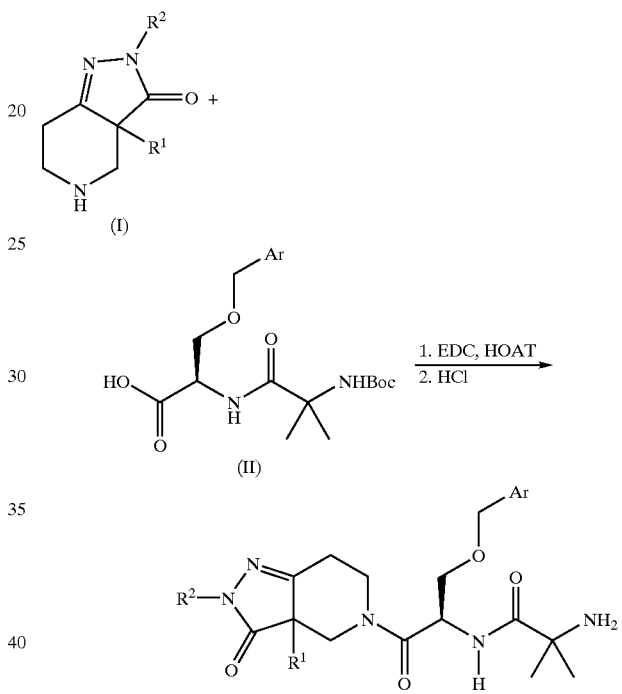

The pyrazalone-piperidines of formula I were prepared analogously according to the procedures described in Examples 3B and 3C starting with the appropriate alkylating agent and alkylhydrazine; the (D)-OBnSer derivatives (II) were prepared steps analogously to the procedures described in Example 23A, Example 23 and Example 5F.

| Ex. # | Isomer | R$^2$ | R$^1$ = —CH$_2$-A$^1$<br>A$^1$ | Ar | MS | MS Method |
|---|---|---|---|---|---|---|
| 27 | d1 | H | 2-pyridyl | phenyl | 493 | PB |
| 28 | d1 | H | 4-thiazolyl | phenyl | 499 | PB |

-continued

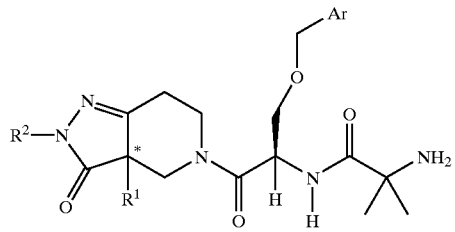

| Ex. # | Isomer | R² | R¹ = —CH₂-A¹ <br> A¹ | Ar | MS | MS Method |
|---|---|---|---|---|---|---|
| 29 | d2 | H | 4-thiazolyl | phenyl | 499 | PB |
| 30 | d1 | H | 5-thiazolyl | phenyl | 499 | APCI |
| 31 | d1 | Me | phenyl | 2,4-di-Cl-Ph | 574.5 | APCI |
| 32 | d1 | Me | phenyl | 2,4-di-F-Ph | 542 | PB |
| 33 | d1 | Me | phenyl | [2,3-O—CH₂—O]Phenyl | 550.2 | PB |
| 34 | d1 | Me | phenyl | 2-CF₃-Ph | 575 | PB |
| 35 | d1 | Me | phenyl | 2-Me-Ph | 520 | PB |
| 36 | d1 | Me | phenyl | 2-pyridyl | 507 | PB |
| 37 | d1 | Me | phenyl | 3,4-di-F-Ph | 542 | PB |
| 38 | d1, 2 | Me | phenyl | 3,5-di-CF₃-Ph | 642 | PB |
| 39 | d1 | Me | phenyl | 3,5-di-Cl-Ph | 576 | APCI |
| 40 | d2 | Me | phenyl | 3-CF₃-Ph | 575 | APCI |
| 41 | d1 | Me | phenyl | 3-Cl-Ph | 540 | APCI |
| 42 | d1 | Me | phenyl | 3-Cl-thiophene | 546, 548 | APCI |
| 43 | d1 | Me | phenyl | 3-F-4-Cl-Ph | 560 | APCI |
| 44 | d1 | Me | phenyl | 3-Me-Ph | 520 | PB |
| 45 | d1 | Me | phenyl | 4-Cl-Ph | 540 | PB |
| 46 | d1 | Me | phenyl | 4-pyridyl | 507 | PB |
| 47 | d1 | Me | phenyl | 4-thiazolyl | 513 | PB |
| 48 | d1 | Me | phenyl | 5-thiazolyl | 513 | APCI |
| 49 | d1, 2 | Me | phenyl | benzisoxazolyl | 547 | PB |
| 50 | d1 | Me | phenyl | 4-pyrimidinyl | 508 | PB |
| 51 | d1, 2 | Me | 4-Ph-Ph | 4-thiazolyl | 589 | APCI |
| 52 | d1, 2 | Me | 4-Ph-Ph | 2-pyridyl | 583 | APCI |
| 53 | d1 | Me | 4-F-Ph | phenyl | 524 | PB |
| 54 | d2 | Me | 4-F-Ph | phenyl | 524 | PB |
| 55 | d1 | Me | 4-F-Ph | 3-Cl-Ph | 558 | PB |
| 56 | d2 | Me | 4-F-Ph | 3-Cl-Ph | 558 | PB |
| 57 | d1 | Me | 4-F-Ph | 3,4-di-F-Ph | 560 | APCI |
| 58 | d2 | Me | 4-F-Ph | 3,4-di-F-Ph | 560 | APCI |
| 59 | d1, 2 | Me | 4-F-Ph | 2-pyridyl | 525 | APCI |
| 60 | d1, 2 | Me | 4-F-Ph | 2-CF₃-Ph | 592 | APCI |
| 61 | d1 | Me | 4-CF₃-Ph | 4-Cl-Ph | 609 | APCI |
| 62 | d1, 2 | Me | 4-CF₃-Ph | 4-Cl-Ph | 609 | APCI |
| 63 | d1, 2 | Me | 3-pyridyl | phenyl | 508 | PB |
| 64 | d1 | Me | phenyl | 3-pyridyl | 508 | PB |
| 65 | d1 | Me | 2-quinolinyl | phenyl | 594 | PB |
| 66 | d2 | Me | 2-quinolinyl | phenyl | 594 | PB |
| 67 | d1 | Me | 2-pyridyl | phenyl | 506 | PB |
| 68 | d2 | Me | 2-pyridyl | phenyl | 506 | PB |
| 69 | d1, 2 | Me | 2-pyridyl | 3-F-4-Cl-Ph | 559, 581 | APCI |
| 70 | d1 | Me | 2-pyridyl | 3-Cl-thiophene | 547, 549 | APCI |
| 71 | d1 | Me | 2-pyridyl | 3-CF₃-Ph | 575 | PB |
| 72 | d1, 2 | Me | 2,4-di-F-Ph | 3,4-di-F-Ph | 579 | APCI |
| 73 | d1, 2 | Me | 2,4-di-F-Ph | 2-pyridyl | 544 | PB |
| 74 | d1 | Me | 4-thiazolyl | phenyl | 513 | APCI |
| 75 | d2 | Me | 4-thiazolyl | phenyl | 513 | PB |
| 76 | d1 | Me | 5-thiazolyl | phenyl | 513 | PB |
| 77 | d1 | Et | 2-pyridyl | phenyl | 521 | PB |
| 78 | d1, 2 | Et | phenyl | 4-thiazolyl | 541 | APCI |
| 79 | d1 | Et | phenyl | 3,5-di-CF₃-Ph | 656 | PB |
| 80 | d1, 2 | Et | phenyl | 3,4-di-F-Ph | 556 | PB |
| 81 | d1 | Et | 2,4-di-F-Ph | 2,4-di-F-Ph | 593 | APCI |
| 82 | d2 | Et | 2,4-di-F-Ph | 2,4-di-F-Ph | 593 | APCI |
| 83 | d1 | Et | 2,4-di-F-Ph | 2-CF₃-Ph | 625 | APCI |
| 84 | d2 | Et | 2,4-di-F-Ph | 2-CF₃-Ph | 625 | APCI |
| 85 | d1 | Et | 2,4-di-F-Ph | 3,4-di-F-Ph | 593 | APCI |
| 86 | d2 | Et | 2,4-di-F-Ph | 3,4-di-F-Ph | 593 | APCI |
| 87 | d1 | Et | 2-pyridyl | 3,4-di-F-Ph | 607 | PB |
| 88 | d2 | Et | 2-pyridyl | 3,4-di-F-Ph | 607 | PB |
| 89 | d1 | Et | 4-CF₃-Ph | 2,4-di-F-Ph | 625 | APCI |
| 90 | d2 | Et | 4-CF₃-Ph | 2,4-di-F-Ph | 625 | APCI |
| 91 | d1 | Et | 4-CF₃-Ph | 3-Cl-Ph | 623 | APCI |
| 92 | d1 | Et | 4-CF₃-Ph | 4-Cl-Ph | 623 | APCI |

-continued

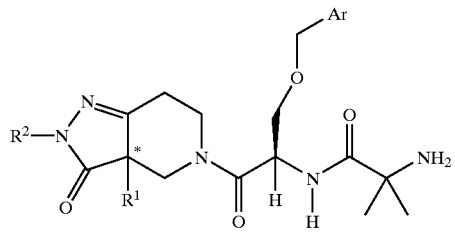

| Ex. # | Isomer | R² | R¹ = —CH₂-A¹<br>A¹ | Ar | MS | MS Method |
|---|---|---|---|---|---|---|
| 93 | d2 | Et | 4-CF₃-Ph | 4-Cl-Ph | 623 | APCI |
| 94 | d1 | Et | 4-CF₃-Ph | 3-Cl-Ph | 568 | APCI |
| 95 | d2 | Et | 4-CF₃-Ph | 3-Cl-Ph | 568 | APCI |
| 96 | d1 | Et | 4-Cl-Ph | 3,4-di-F-Ph | 590 | PB |
| 97 | d2 | Et | 4-Cl-Ph | 3,4-di-F-Ph | 590 | PB |
| 98 | d1 | Et | 4-Cl-Ph | 3-5-di-Cl-Ph | 622 | PB |
| 99 | d2 | Et | 4-Cl-Ph | 3-5-di-Cl-Ph | 622 | PB |
| 100 | d1 | Et | 4-Cl-Ph | 3-Cl-Ph | 589 | PB |
| 101 | d2 | Et | 4-Cl-Ph | 3-Cl-Ph | 589 | PB |
| 102 | d1 | Et | 4-F-Ph | 3,4-di-F-Ph | 574 | PB |
| 103 | d2 | Et | 4-F-Ph | 3,4-di-F-Ph | 574 | PB |
| 104 | d1 | Et | 4-F-Ph | 3-Cl-Ph | 572 | APCI |
| 105 | d2 | Et | 4-F-Ph | 3-Cl-Ph | 572 | APCI |
| 106 | d1, 2 | Et | 4-Me-Ph | 2-CF₃-Ph | 602 | APCI |
| 107 | d1, 2 | Et | 4-Me-Ph | 3,4-di-F-Ph | 570 | APCI |
| 108 | d1, 2 | CF₃CH₂ | phenyl | 4-thiazolyl | 595 | APCI |
| 109 | d1 | CF₃CH₂ | phenyl | 3-CF₃-Ph | 642.3 | APCI |
| 110 | d1 | CF₃CH₂ | phenyl | 3,5-di-Cl-Ph | 643 | APCI |
| 111 | d2 | CF₃CH₂ | phenyl | 3,5-di-Cl-Ph | 644 | APCI |
| 112 | d1 | CF₃CH₂ | phenyl | 3,4-di-F-Ph | 610.2 | APCI |
| 113 | d2 | CF₃CH₂ | phenyl | 3,4-di-F-Ph | 610.2 | APCI |
| 114 | d1 | CF₃CH₂ | phenyl | 3,5-di-Cl-Ph | 643 | APCI |
| 115 | d2 | CF₃CH₂ | phenyl | 3,5-di-Cl-Ph | 644 | APCI |
| 116 | d1 | CF₃CH₂ | phenyl | 3-CF₃-Ph | 642.3 | APCI |
| 117 | d1 | CF₃CH₂ | phenyl | 3,4-di-F-Ph | 610.2 | APCI |
| 118 | d2 | CF₃CH₂ | phenyl | 3,4-di-F-Ph | 610.2 | APCI |
| 119 | d1, 2 | CF₃CH₂ | phenyl | 4-thiazolyl | 595 | APCI |
| 120 | d1, 2 | CF₃CH₂ | 2,4-di-Cl-Ph | 2-pyridyl | 643 | APCI |
| 121 | d1, 2 | CF₃CH₂ | 2,4-di-Cl-Ph | 4-thiazolyl | 649 | APCI |
| 122 | d1 | CF₃CH₂ | 2,4-F-Ph | 2-CF₃-Ph | 679 | APCI |
| 123 | d2 | CF₃CH₂ | 2,4-F-Ph | 2-CF₃-Ph | 679 | APCI |
| 124 | d1 | CF₃CH₂ | 2,4-F-Ph | 3,4-di-F-Ph | 647 | APCI |
| 125 | d2 | CF₃CH₂ | 2,4-F-Ph | 3,4-di-F-Ph | 647 | APCI |
| 126 | d1, 2 | CF₃CH₂ | 2,4-F-Ph | 4-thiazolyl | 617 | PB |
| 127 | d1 | CF₃CH₂ | 2-pyridyl | 2,4-di-Cl-Ph | 643 | APCI |
| 128 | d2 | CF₃CH₂ | 2-pyridyl | 2,4-di-Cl-Ph | 643 | APCI |
| 129 | d1 | CF₃CH₂ | 2-pyridyl | 2,4-di-F-Ph | 611 | PB |
| 130 | d2 | CF₃CH₂ | 2-pyridyl | 2,4-di-F-Ph | 611 | PB |
| 131 | d1 | CF₃CH₂ | 2-pyridyl | 2-CF₃-4-F-Ph | 661 | APCI |
| 132 | d1 | CF₃CH₂ | 2-pyridyl | 2-CF₃-Ph | 643 | PB |
| 133 | d2 | CF₃CH₂ | 2-pyridyl | 2-CF₃-Ph | 643 | PB |
| 134 | d1 | CF₃CH₂ | 2-pyridyl | 3,4-di-F-Ph | 611 | PB |
| 135 | d2 | CF₃CH₂ | 2-pyridyl | 3,4-di-F-Ph | 611 | PB |
| 136 | d1 | CF₃CH₂ | 2-pyridyl | 3,5-di-Cl-Ph | 643 | APCI |
| 137 | d1 | CF₃CH₂ | 2-pyridyl | 3-Cl-Ph | 609 | PB |
| 138 | d1 | CF₃CH₂ | 2-pyridyl | 3-Cl-thiophene | 615, 617 | APCI |
| 139 | d1, 2 | CF₃CH₂ | 2-pyridyl | 3-F-4-Cl-Ph | 627, 629 | APCI |
| 140 | d1 | CF₃CH₂ | 2-pyridyl | 3-OCF₃-Ph | 659 | APCI |
| 141 | d1 | CF₃CH₂ | 2-pyridyl | 4-Cl-Ph | 609 | PB |
| 142 | d2 | CF₃CH₂ | 2-pyridyl | 4-Cl-Ph | 609 | PB |
| 143 | d1, 2 | CF₃CH₂ | 3-pyridyl | 2,4-di-F-Ph | 612 | APCI |
| 144 | d1, 2 | CF₃CH₂ | 3-pyridyl | 2-CF₃-Ph | 644 | APCI |
| 145 | d1, 2 | CF₃CH₂ | 3-pyridyl | 4-Cl-Ph | 610 | APCI |
| 146 | d1 | CF₃CH₂ | 4-CH₃-Ph | 3-Cl-Ph | 622 | APCI |
| 147 | d2 | CF₃CH₂ | 4-CH₃-Ph | 3-Cl-Ph | 622 | APCI |
| 148 | d1 | CF₃CH₂ | 4-Cl-Ph | 3,4-di-F-Ph | 644 | PB |
| 149 | d2 | CF₃CH₂ | 4-Cl-Ph | 3,4-di-F-Ph | 644 | PB |
| 150 | d1 | CF₃CH₂ | 4-Cl-Ph | 3,5-di-Cl-Ph | 675 | PB |
| 151 | d2 | CF₃CH₂ | 4-Cl-Ph | 3,5-di-Cl-Ph | 675 | PB |
| 152 | d2 | CF₃CH₂ | 4-Cl-Ph | 3-Cl-Ph | 642 | PB |

-continued

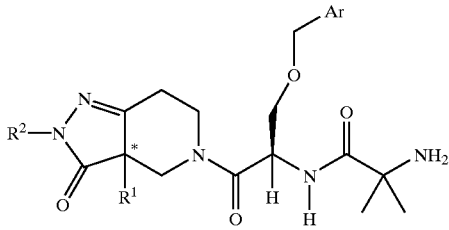

| Ex. # | Isomer | R² | R¹ = —CH₂-A¹ A¹ | Ar | MS | MS Method |
|---|---|---|---|---|---|---|
| 153 | d1 | CF₃CH₂ | 4-Cl-Ph | 3-Cl-Ph | 642 | PB |
| 154 | d1 | CF₃CH₂ | 4-F-Ph | 3,4-di-F-Ph | 628 | PB |
| 155 | d2 | CF₃CH₂ | 4-F-Ph | 3,4-di-F-Ph | 628 | PB |
| 156 | d1 | CF₃CH₂ | 4-F-Ph | 3-Cl-Ph | 626 | PB |
| 157 | d2 | CF₃CH₂ | 4-F-Ph | 3-Cl-Ph | 626 | PB |
| 158 | d1, 2 | CF₃CH₂ | 4-Me-Ph | 2-CF₃-Ph | 656 | APCI |
| 159 | d1, 2 | CF₃CH₂ | 4-Me-Ph | 3,4-di-F-Ph | 624 | APCI |

Note:
in the above table, the isomer designation refers to the stereochemistry at the C-3 position (indicated by the "*" in the structure) of the pyrazalone-piperidine group; d1 and d2 refer to isomers that were chromatographically separated; d1, 2 refers to a mixture of isomers.
Abbreviations used in the table above are: Ph is phenyl; PB is particle bombardment; and APCI is atmospheric pressure chemical ionization.
The following are NMR data for the compounds of the above table as indicated.

Example 37: $^1$H NMR (400 MHz, d4MeOH): d 7.2 (m, 5H), 5.2 (t, 1H), 4.6 (m, 3H), 3.8 (d, 2H), 3.1 (d, 1H), 3.0 (s, 3H), 2.6 (dd, 2H), 1.6 (s, 6H).

Examples 67 & 68: $^1$H NMR (300 MHz, d4-MeOH): d 8.85 (s, 1H), 8.6 (t, 1H), 8.1 (d, 1H), 8.0 (t, 1H), 7.35 (s, 5K), 5.15 (s, 1H), 4.6 (bs, 3H), 3.85 (m, 2H), 3.65 (m, 2H), 3.2 (s, 3H), 2.75 (m, 2H), 1.65 (s, 6H).

Example 128: $^1$H NMR (400 MHz, d4-MeOH):d 8.8 (s, 1H), 8.6 (s. 1H), 8.5 (t 1H), 7.96 (t 1H), 7.9 (d, 1H), 7.45 (d, 1H), 7.33 (d, 1H), 52 (s, 1H), 4.6 (a, 3H), 4.4 (m, 1H), 4.2 (m, 2H), 3.9 (m, 4H), 3.5 (m), 3.2 (m, 2H), 2.8 (dd, 2H), 1.6 (s, 6H).

Examples 129 & 130: $^1$H NMR (400 MHz, d4-MeOH): d 8.76 (s, 1H), 8.50 (t, 1H), 7.92 (dt, 2H), 7.43 (q, 1H), 6.90 (t 1H), 5.20 (m, 1H), 4.90 (m), 4.30 (m, 1H), 4.20 (m, 1H), 3.7–3.4 (m), 3.30 (s, 2H), 3.20 (m, 1H), 2.80 (dd, 2H), 1.60 (s, 6H).

Example 137: $^1$H NMR (300 MHz, d4-MeOH): d 8.7 (1, 1H), 8.45 (t, 1H), 7.9 (t, 2H), 7.25 (m, 4H), 52 (m, 1H), 4.95 (d, 1H), 4.6 (s, 2H), 4.3 (m, 1H), 3.8 (t, 2H), 3.5 (dd, 2H), 2.8 (m, 1H), 2.8 (dd, 2H), 1.6 (s, 6H).

Example 138: $^1$H NMR (400 MHz, d4MeOH): d 8.8 (dd, 1H), 8.6 (s, 1H), 8.5 (t, 1H), 7.95 (t 1H), 7.9 (s, 1H), 7.3 (s, 1H), 7.0 (s, 1H), 5.2 (s, 1H), 4.85 (s, 3H), 4.4 (ml 1H), 4.18 (m, 1H), 3.8 (m, 2H), 3.5 (dd, 2H), 3.2 (d, 2H), 2.8 (dd, 2H), 1.6 (s, 6H).

Examples 141 & 142: $^1$H NMR (300 MHz, d4MeOH): d 8.75 (m, 1H), 8.5 (m, 1H), 7.9 (m, 2H), 7.3 (s, 2H), 5.2 (m, $_1$H), 4.65 (m, 1H), 4.55(s, 2H), 4.35(m, 1H), 4.20 (m, 1H), 3.8 (t, 1H), 3.5 (dd, 2H), 3.15 (d, 1H), 2.8 (dd, 2H), 1.6 (s, 2H).

EXAMPLES 160–179

Examples 160 to 179 shown in the table below were prepared according to the scheme illustrated below by coupling the appropriately substituted pyrazalone-piperidine I (in the scheme) with the (D)-Trp derivative (III) (see Example 2C) in an analogous manner to the procedures described in Examples 3E and 3F.

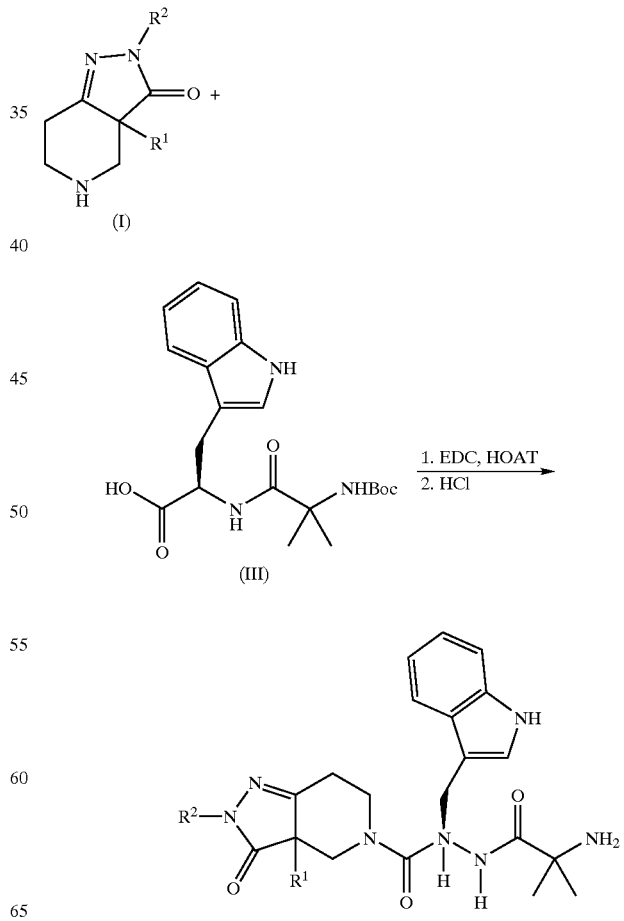

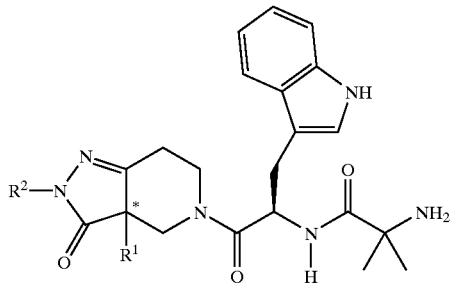

| Ex. # | Isomer | R² | R¹ = —CH₂-A¹ A¹ | MS | MS Method |
|---|---|---|---|---|---|
| 160 | d1 | Me | 4-CF₃-Ph | 584 | APCI |
| 161 | d1, 2 | Me | 4-CF₃-Ph | 584 | APCI |
| 162 | d1 | Me | 4-F-Ph | 533 | PB |
| 163 | d2 | Me | 4-F-Ph | 533 | PB |
| 164 | d1 | Me | 4-Ph-Ph | 591 | APCI |
| 165 | d1, 2 | Et | 2,4-di-Cl-Ph | 597 | APCI |
| 166 | d1, 2 | Et | 2,4-F-Ph | 566 | APCI |
| 167 | d1 | Et | 4-CF₃-Ph | 598 | APCI |
| 168 | d1, 2 | Et | 4-CF₃-Ph | 598 | APCI |
| 169 | d1 | Et | 4-Cl-Ph | 563 | PB |
| 170 | d2 | Et | 4-Cl-Ph | 563 | PB |
| 171 | d1, 2 | Et | 4-F-Ph | 547 | APCI |
| 172 | d1, 2 | Et | 4-Me-Ph | 543 | APCI |
| 173 | d1, 2 | CF₃CH₂ | 2,4-di-Cl-Ph | 651.5 | APCI |
| 174 | d1, 2 | CF₃CH₂ | 2,4-di-F-Ph | 620 | APCI |
| 175 | d1 | CF₃CH₂ | 4-Cl-Ph | 617 | PB |
| 176 | d2 | CF₃CH₂ | 4-Cl-Ph | 617 | PB |
| 177 | d1 | CF₃CH₂ | 4-F-Ph | 601 | APCI |
| 178 | d2 | CF₃CH₂ | 4-F-Ph | 601 | APCI |
| 179 | d1, 2 | CF₃CH₂ | 4-Me-Ph | 597 | APCI |

Note:
in the above table, the isomer designation refers to the stereochemistry at the C-3 position (indicated by the "*" in the structure) of the pyrazalone-piperidine group; d1 and d2 refer to isomers that were chromatographically separated; d1, 2 refers to a mixture of isomers.

EXAMPLES 180–183

Examples 180 to 183 shown in the table below were prepared according to the scheme illustrated below by coupling the appropriately substituted pyrazalone-piperidine I with the acid intermediate IV in an analogous manner to the procedures described in Examples 3E and 3F.

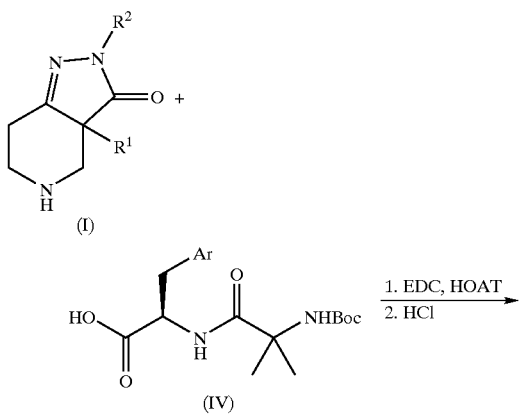

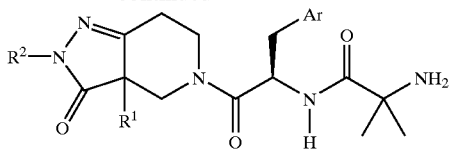

The acid intermediate (IV) was prepared by treating an amino acid with the product from Example 5D using the established procedure described in Example 5F.

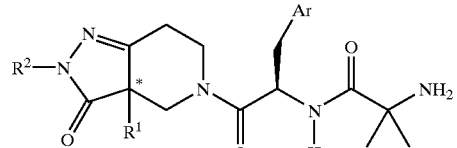

| Ex. # | Isomer | R² | R¹ = —CH₂-A¹ A¹ | Ar | MS | Method |
|---|---|---|---|---|---|---|
| 180 | d1, 2 | Me | Phenyl | (CH₂)₂Ph | 504 | PB |
| 181 | d1, 2 | Me | Phenyl | SCH₂Ph | 559 | PB |
| 182 | d1 | Me | Phenyl | 2-Naphthalenyl | 527 | APCI |
| 183 | d1, 2 | Me | Phenyl | CH₂O-(4-F-Ph) | 524 | PB |

Note:
in the above table, the isomer designation refers to the stereochemistry at the C-3 position (indicated by the "*" in the structure) of the pyrazalone-piperidine group; d1 and d2 refer to isomers that were chromatographically separated; d1, 2 refers to a mixture of isomers.

EXAMPLE 184

2-Amino-N-[2-(3a-(R)-benzyl-2-methy-3-oxo-2,3,3a,4,6,7-hexahydro-pyrazolo[4,3-c]pyridin-5-yl)-(R)-benzyloxymethyl-2-oxo-ethyl]-2-methyl-propionamide, L-tartrate A. 4-Oxo-piperidine-1,3-dicarboxylic acid 1-tert-butyl ester 3-ethyl ester To a solution of 4-oxo-piperidine-3-carboxylic acid ethyl ester hydrochloride (100 g, 0.482 mol) in IPE (725 mL) and water (360 mL) was slowly added TEA (63.5 g, 0.627 mol), followed by (Boc)₂O (115.7 g, 0.53 mol). The mixture was stirred overnight under nitrogen. The organic phase was separated and washed with water and dried over Na₂SO₄, and concentrated in vacuo to afford the desired product as crystals (142.9 g, yield 109%, containing a small amount of IPE).

B. 3-Benzyl-4-oxo-piperidine-1,3-dicarboxylic acid 1-tert-butyl ester 3-ethyl ester To a solution of 4-oxo-piperidine-1,3-dicarboxylic acid 1-tert-butyl ester 3-ethyl ester (73.36 g, 0.27 mol) in DMF (734 mL) lithium carbonate (50 g, 0.676 mol) was added, followed by benzyl bromide (55.44 g, 0.324 mol). The mixture was heated to about 60° C. and stirred for about 20 hours. The reaction mixture was then cooled to room temperature and extracted with IPE, washed with water and dried over magnesium sulfate. After filtration and concentration in vacuo a solid was obtained. Recrystallization of the crude product in hexane afforded a white solid (33.6 g, yield 38.2% h).

C. 3a-Benzyl-2-methyl-2,3a,4,5,6,7-hexahydro-pyrazolo[4,3-c]pyridin-3-one

To a solution of 3-benzyl-4-oxo-piperidine-1,3-dicarboxylic acid 1-tert-butyl ester 3ethyl ester (1935.97 g, 5.36 moo in toluene (9700 mL) was added methylhydrazine (299.2 mL, 5.63 mot), followed by acetic acid (325 mL, 5.68 mol) slowly at about 8° C. The reaction mixture was heated slowly to about 65° C. and stirred for about 7.5 hours. After cooling to room temperature, the organic layer was washed with 10% sodium bicarbonate, water and saturated NaCl solution and concentrated in vacuo to a low volume. The reaction was repeated at same scale, twice. The concentrated product solutions from the three reactions were combined and mixed with IPE (50 L), cooled to about 0° C., HCl gas was introduced repeatedly and stirred at room temperature overnight until the deprotection was complete. The mixture was concentrated in vacuo to about half of the original volume, methylene chloride (24 L) was added, followed by NH$_4$OH (22 L). The mixture was then extracted with methylene chloride and concentrated to a low volume (6 to 7 L). Hexane (20 L) was added and the mixture was cooled to about 1520° C. The free base product was collected as crystals and dried under vacuum (2985 g total, yield 84.8%).

D. 3a-(R)-Benzyl-2-methyl-2,3a,4,5,6,7-hexahydro-pyrazolo[4,3-c]pyridin-3-one, L-tartrate To a solution of 3a-benzyl-2-methyl-2,3a,4,5,6,7-hexahydro-pyrazolo[4,3-c]pyridin-3-one (100 g, 0.41 moo) in a mixture of acetone/water (970 mL/120 mL) was added L-tartaric acid (67.55 g, 0.45 mol). The mixture was heated to about 50° C. and stirred over night. The reaction mixture was cooled to about 1015° C. and precipitates were filtered, washed with cold acetone/water and dried under vacuum. The product was obtained as a white solid (157.8 g, yield 97.83%, 99% ee).

E. 2-tert-Butoxycarbonylamino-2-methyl-propionic acid

2-Aminoisobutyric acid (140g, 1.36 mol), 1 N NaOH (1620 mL, 1.63 moo), (Boc)20 (375 mL, 1.63 mol) and THF 420 mL were mixed together and stirred at room temperature overnight. The reaction mixture was diluted with ethyl acetate (700 mL) and adjusted to about pH 3.0 by adding 6 N HCl. The organic phase separated was washed with saturated NaCl solution and concentrated to approximately 114 of the original volume. After treatment with hexane a white solid product was isolated and collected (125.8 g, yield 45.44%). An additional 7.8 g of product was recovered from the mother liquor.

F. 2-tert-Butoxycarbonylamino-2-methyl-propionic acid 2,5-dioxo-pyrrolidin-1-yl ester To a solution of 2-tert-butoxycarbonylamino-2-methyl-propionic add (100 g, 0.492 mol) and succinic anhydride (60.02 g, 0.522 mol) in methylene chloride (1000 mL) was added EDC (100.09 g, 0.522 mol) while stirring under nitrogen. The mixture was stirred under nitrogen overnight. The reaction mixture was then diluted with ethyl acetate (1 L), washed with saturated sodium bicarbonate solution and water, then concentrated in vacuo to a low volume. White crystals precipitated out of solution and were collected by filtration and dried under vacuum to afford the product (104.9 g+27.3 g, yield 89.5%).

G. 3-(R)-Benzyloxy-2-(2-tert-butoxycarbonylamino-2-methyl-propionylamino) propionic add To a solution of 2-amino-3-benzyloxy-propionic acid (26.2 A, 0.113 mol) in water (101.8 mL) and TEA (28.53 g, 0.282 mol) was added 2-tert-butoxycarbonylamino-2-methyl-propionic acid 2,5-dioxo-pyrrolidin-1-yl ester (33.94g, 0.113 mol) in THF (407 mL). The mixture was stirred overnight at room temperature under nitrogen. A 10% citric add solution (500 mL) was added to th mixture. The mixture was stirred for another 10 min., then diluted with ethyl acetate (500 mL). The organic phase was separated from the mixture and washed with water and saturated NaCl solution and then concentrated in vacuo to a thick oil. The crude oil was treated with IPE/hexane (50/50) and cooled to about 10° C. to afford a white solid product (42.3 g, yield 98.4%).

H. {1-[2-(3a-(R)-Benzyl-2-methyl-3-oxo-2,3,3a,4,6,7-hexahydro-pyrazolo[4,3-c]pyridin-5-yn)-1-(R)-benzyloxymethyl-2-oxo-ethylcarbamoyl]-1-methyl-ethyl}-carbamic acid tert-butyl ester To a solution of 3a-(R)-benzyl-2-methyl-2,3a,4,5,6,7-hexahydro-pyrazolo[4,3-c]pyridin-3-one, L-tartrate (10.81 g, 0.0275 mol) in ethyl acetate (216.2 mL) at about 66° C. was added TEA (8.43 mL, 0.0605 mol). The mixture was stirred for about 1.5 hours. After removal of the precipitated salt by filtration, 3-benzyloxy-2-(2-tert-butoxycarbonylamino-2-methyl-propionylamino)-propionic add (8.7 g, 0.0229 mol) and TEA (19.15 mL, 0.1374 mol) were added at about −35° C., followed by the dropwise addition of 50% PPAA in ethyl acetate (27.5 mL, 0.0458 mol). The mixture was stirred for about 2 hours at about −20 QC to about −27° C., then 1.5 hours while the temperature was slowly raised to about 0° C. The reaction mixture was poured into water and extracted with IPE, washed with 7% NaCl solution and concentrated in vacuo. The crude oil that was obtained was treated with IPE/hexane (50150) to allow crystallization. The product was obtained as a white solid (10.3 g, yield 74.3%).

I. 2-Amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-2-methyl propionamide To a solution of {1-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethylcarbamoyl]-1-methyl-ethyl}-carbamic acid tert-butyl ester. (10.3 g, 0.017 mol) in methylene chloride (68.6 mL) at about 0–5° C. was added TFA (35 mL) to maintain the temperature below about 5° C. The temperature was then raised to room temperature. The mixture was stirred for about 3 hours. Methylene chloride was replaced with ethyl acetate as a solvent. The mixture was then adjusted to about pH 8 with a saturated sodium bicarbonate solution, then washed with saturated NaCl and concentrated in vacuo to a low volume. A white solid product was obtained after treating the mixture with IPA and then hexane (7.4 g, yield 86.1%). HPLC showed product containing 0.2% diastereomer.

J. 2-Amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-2-methyl-propionamide, L-tartrate To a solution of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethy]2-methyl propionamide from step I (385 g, 0.761 mol) in methanol (4000 mL) was added L-(+)-tartaric acid (114.5 g, 0.761 mot) and the mixture was stirred overnight. The resulting hazy solution was filtered yielding a dear solution which was concentrated to remove most of the solvent. Ethyl acetate (total 12 L) was added and the remaining methanol was removed azeotropically between about 630 and 72° C. The solid that was isolated was dissolved in ethyl acetate and the solution was refluxed for about 16 hours, then allowed to cool to room temperature overnight. The product was collected as a white solid (482.3 g, yield 96.8%), M.P. 174–176° C.

EXAMPLE 185

2-Amino-N-{1-(2,4-difluoro-benzyloxym thyl)-2-oxo-2-[3-oxo-3a-pyridin-2-ylmethyl2-(2,2,2-trifuoro-ethyl)-2,3,3a,4,6,7-hexahydro-pyrazolo]4,3-c]pyridin-5-yl)-ethyl}-2-methyl-propionamide L-(+) tartrate A. 4-oxo-3-pyridin-2-ylmethyl-piperidine-1,3-dicarboxylic acid 1-tert-butyl ester 3ethyl ester To a solution of 4-oxo-piperidine-1,3-dicarboxylic acid 1-ten-butyl ester 3-ethyl ester (10.34 g, 38.2 mmol) in DMF (40 mL) at about 0° C. was added picolyl chloride hydrochloride (5.7 g, 34.7 mmol), potassium carbonate (14.4 g, 104.1 mmol) and potassium iodide (5.76 g. 34.7 mmol). After stirring at about 0° C. for about 2 hours, the ice bath was removed and DABCO (973 mg, 8.68 mmol) was added. The reaction mixture was stirred for about 30 min. and poured into a mixture of water and IPE. The organic layer was separated and washed with saturated aqueous $NaHCO_3$ and saturated aqueous NaCl, dried over $Na_2SO_4$ and concentrated in vacuo. The crude residue was crystallized from hexanes to give a white solid (8.19 g, yield 65%). $^1$H-NMR ($CDCl_3$) δ 1.17 (t, 3H), 1.48 (s, 9H), 1.55 (s, 2H), 2.61 (m, 1H), 2.71 (m, 1H), 3.31–3.50 (m, 3H), 4.11 (d, 2H), 4.49 (d, 1H), 7.06 (br s, 1H), 7.17(d, 1H), 7.54 (m, 1H), 8.40 (s, 1H).

B. 3-oxo-3a-pyridin-2-ylmethyl-2-(2,2,2-trifluoro-ethyl-2,3,3a,4,6,7-hexahydro pyrazolo[4,3-c]pyridine-5-carboxylic acid tert-butyl ester A 70% aqueous solution of $CF_3CH_2NHNH_2$ (325 mL, 1.986 mol) (obtain d from Aldrich) was extracted with toluene (3×1200 mL). To a solution of the product from step A (600 g, 1.655 mol) in toluene (900 mL) was first added the combined toluene extracts containing the anhydrous 2,2,2-trifluoroethyl hydrazine, followed by acetic acid (121.4 g, 1.986 mol). The reaction mixture was heated at about 70° C. for about 2 hours, then another toluene extraction of 70% aqueous 2,2,2-trifluoroethyl hydrazine (50 g) was added. The reaction mixture was heated at about 80° C. for about 3.5 hours, cooled to room temperature and diluted with saturated aqueous $NaHCO_3$ (2 L). The toluene layer was separated and washed with saturated aqueous NaCl, dried over $Na_2SO_4$ and concentrated in vacuo to give an oil (754.8 g). Crystallization from methanol/water afforded the desired product as a white solid (609.5 g). $^1$H-NMR ($CDCl_3$) δ 1.50 (s, 9H), 2.53 (d, 1H), 2.70 (br s, 2H), 2.88 (br s, 1H), 3.31 (m, 2H), 3.97 (m, 1H), 4.19 (m, 1H), 4.46 (br s, 1H), 4.63 (br s, 1H). 7.06 (m, 2H), 7.51 (m, $_1$H), 8.34 (m, $_1$H).

C. 3a-Pyridin-2-ylmethyl-2-(2,2,2-trifluoroethyl)-2,3a,4,5,6,7-hexahydro-pyrazolo[4,3-c]pyridin-3-one Methanesulfonic add (11.6 g, 121 mmol) was added dropwise to a solution of the product from step B (10 g, 24.2 mmol) in $CH_2Cl_2$ (100 mL) over about 30 minutes. The reaction mixture was stirred for about 1 hour, then cooled to about 0° C., and then triethylamine (18.6 mL, 133.1 mmol) was added through an addition funnel. The mixture was allowed to warm to room temperature over about 1 hour, diluted with additional $CH_2Cl_2$ and washed with saturated aqueous NaCl, dried over $Na_2SO_4$, filtered and concentrated in vacuo to afford the product as a white solid (7.2 g). $^1$H-NMR ($CDCl_3$) δ: 2.51–2.72 (m, 4H), 3.35 (m, 2H), 3.49 (m, 2H), 4.03 (m, 1H), 4.25 (m, 1H), 7.08 (d, 2H). 7.51 (t, 1H). 8.37 (d, 1H).

D. 3a-Pyridin-2-ylmethyl-2-(2.2.2-trifluoroethyl)-2,3a,4,5,6,7-hexahydro-pyrazolo[4,3-c]pyridin-3-one (D)-tartrate In a dry and nitrogen purged 5 L round bottom flask equipped with a mechanical stirrer, D-(–) tartaric acid (129 g, 0.86 mol) was added to the product from step C (243 g, 0.78 mol) in acetone/water (9:1, 2430 mL) at about 17° C. The mixture was stirred at room temperature overnight, filtered, the solid was collected and washed with cold acetone and dried under vacuum. The product was obtained as a yellow solid (284 g, yield 78.8%).

E. 2-tert-Butoxycarbonylamino-3-(2,4-difluoro-benzyloxy)-propionic acid

To a solution of N-Boc-(D)-serine (452 g, 2.2026 mol) in a mixture of THF (7 L) and DMF (3 L) at about 0° C. was added potassium tert-butoxide solution (515.8 g, 4.5963 mol). The reaction mixture was stirred at about 0° C. for about 30 min., then 2.4-difluorobenzyl bromide (456.5 g, 2.2051 mol) was added. After warming to room temperature, the reaction mixture was concentrated in vacuo to remove the THF. The reaction mixture was partitioned between 4.5 L $H_2O$ and 4.5 L IPE. The layers were separated and the pH of the aqueous layer was adjusted with 1 N HCl to about 3. The aqueous layer was extracted twice with 4 L each of IPE. The organic solution was dried over $Na_2SO_4$, and concentrated in vacuo to yield a yellow waxy solid (518.0 g, yield: 70.9%). $^1$H-NMR ($CDCl_3$) δ 1.44 (s, 9H), 0.73 (m, 1H), 3.94 (d, 1H). 4.44 (br s, 1H), 4.54 (s, 2H), 5.34 (m, 1H), 6.78 (m, 1H), 0.84 (m, 1H), 7.30 (m, 1H).

F. 2-Amino-3-(2.4-difluoro-benzyloxy)-propionic acid, methanesulfonic acid salt

To a solution of the product from step E (1.19 g, 3.59 mmol) in $CH_2Cl_2$/IPE 1:1, 12 mL) was added methanesulfonic acid (1.72 g, 17.95 mmol) through a syringe over about 10 minutes. A solid immediately precipitated out of solution. After about 1 hour, the solid was filtered and washed with a $CH_2Cl_2$/IPE mixture (1:1) to afford 939 mg of product (yield 80%).

G. 2-(2-tert-Butoxycarbonylamino-2-methyl-propionylamino)-3-(2,4-difluoro benzyloxy)-prorionic acid To a solution of the product from step F (520 mg, 1.46 mmol) in THF/water (4:1, 10 mL) was added 2-tert-butoxycarbonylamino-2-methylpropionic acid-2,5-dioxo-pyrrolidin-1-yl ester (438 mg, 1.46 mmol) and triethylamine (369 mg, 3.65 mmol). The reaction mixture was stirred at room temperature for about 1 hour and quenched with a 10% aqueous citric add solution (10 mL). After about 15 min., ethyl acetate (50 mL) was added and the organic layer was separated and washed with saturated aqueous NaCl, dried over $Na_2SO_4$ and concentrated in vacuo to give a foam (534.1 mg, yield 88%). $^1$H-NMR ($CD_3OD$): δ 1.38 (br s, 15H), 3.77 (d, 1H), 3.92 (d, 1H), 4.52 (m, 3H), 6.92 (m, 1H), 7.41 (m, 1H), 7.58 (d, 1H).

H. (1-{1-(2,4-Difluoro-benzyloxymethyl)-2-oxo-2-[3-oxo-3a-pyridin-2-ylmethyl-2-(2,2,2-trifluoro-ethyl)-2,3,3a,4,6,7-hexahydro-pyrazolo[4,3-c]pyridin-5-yl]-ethylcarbamoyl}-1-methyl-ethyl) carbamic acid tert-butyl ester (a) The product from step D (517 g, 1.12 mol) was added at about 6° C. to ethyl acetate (5170 mL) in a dry and nitrogen purged 12 L round bottom flask equipped with a mechanical stirrer. The solution was cooled to about −40° C., then triethylamine (398 mL, 2.86 mol) was added over about 45 minutes. The reaction mixture was stirred for about 90 min. at a temperature between about −50° C. and about −40° C., filtered into a 22 L round bottom flask purged with nitrogen and washed with ethyl acetate (2068 mL, pre-cooled to about −50° C.) to give the free base as a white solid.

(b) The product from step G (425 g, 1.02 mol) was added at about −30° C. to an ethyl acetate solution containing the product from step H(a), triethylamine (654 mL, 4.69 mol) and PPAA (50% in thyl acetate, 916 mL, 1.53 mol). The reaction mixture was stirred for about 1 hour, washed with water and saturated aqueous NaCl, dried over $Na_2SO_4$ and concentrated in vacuo to give the product as an oil (636 g, yield: 87.8%).

I. 2-Amino-N-(1-(2,4-difluoro-benzyloxymethyl)-2-oxo-2-[3-oxo-3a-pyidin-2-ylmethyl-2-(2,2,2-trifluoro-ethyl-2,3,3a,4,6,7-hexahydro-pyrazolo[4,3-c]pyridin-5-yl]-ethyl)-2-methyl-propionamide Methanesulfonic acid (258.3 mL, 3.98 mol) was added dropwise at about 15° C. over about 55 minutes to the product from step H (566 g, 0.796 mol) in $CH_2Cl_2$ (11,320 mL) in a dry and nitrogen purged 22 L round bottom flask equipped with a mechanical stirrer. The mixture was stirred for about 40 minutes at about 20° C., then saturated aqueous NaHCO$_3$ (8,490 mL) was added until the pH was about 7.8. The organic layer was separated, washed with water and saturated aqueous NaCl, dried over Na$_2$SO$_4$, and concentrated in vacuo to afford an oily product (388.8 g. yield 80%).

J. 2-Amino-N-{1-(2,4-difluoro-benzyloxymethyl)-2-oxo-2-[3-oxo-3a-pyridin-2-ylmethyl-2-(2,2,2-trifluoroethyl)-2,3,3a,4,6,7-hexahydro-pyrazolo[4,3-c]pyridin-5-yl-ethyl}-2-methyl-propionamide L-(+) tartrate To a solution of product from step 1 (370 g, 0.6 mol) in methanol (4,070 mL) in a 12 L round bottom flask equipped with a mechanical stirrer was added L-(+) tartaric acid (90 g, 0.6 mol). The reaction mixture was stirred for about 90 min. at about 22° C., filtered and concentrated. The crude residue was diluted with ethyl acetate (4,560 mL), heated at about 70° C. and slowly allowed to cool to room temperature over about 17 hours. The solid was filtered and dried to give white crystals, mp 188–189° C. (348.46 g, yield 76%). $^1$H NMR (MeOH, d4) δ: 8.28 (d, 1H), 7.59 (t, 1H), 7.41–7.39 (m, 1H), 7.18–7.13 (m, 1H), 6.92 (t, 1H), 5.2 (t, 1H), 4.56 (bs, 3H), 4.36 (s, 2H), 4.31–4.25 (m, 1H), 4.134.06 (m, 1H), 3.78 (d, 2H), 3.21 (t, 1H), 3.18–2.96 (m, 2H), 2.662.55 (m, 2H), 1.57 (d, 6H). MS: MH+ 611. [a]$^{589}$+22.03 (c=11.9, MeOH).

EXAMPLE A

The following are the results of the "Female Rat Study" described hereinabove wherein the rats were administered the GH secretagogue compound 2-amino-N-[2-(3a-(R)-benzyl-2-methyl-3-oxo-2,3,3a,4,6,7-hexahydro-pyrazolo[4,3-c]pyridin-5-yl)1-(R)-(benzyloxymethyl)-2-oxo-ethyl]-isobutyramide L-tartaric acid salt.

TABLE 1

| | | | | | | |
|---|---|---|---|---|---|---|
| Surgery | Dose (mg/kg) | Insulin (uU/mL) | Glucose (mg/dl) | Lactate (mg/dl) | Cholesterol (mg/dl) | Triglyceride (mg/dl) |
| Sham | Vehicle | 118.8 | 181.7 | 4.6 | 97.9 | 254.8 |
| Sham | 0.5 | 94.9 | *142.7 | 3.7 | 95.4 | 219.6 |
| Sham | 5.0 | 95.7 | *139.9 | *3.2 | *80.6 | 227.2 |
| Ovx | Vehicle | 112.8 | 194.0 | 3.9 | 106.8 | 182.7 |
| Ovx | 0.5 | *78.7 | 179.7 | 3.6 | 92.5 | 181.9 |
| Ovx | 5.0 | *84.1 | 177.2 | 3.1 | 102.2 | 158.4 |

Mean Plasma Insulin and Metabolite Levels After Daily Dosing of a GHRP Mimetic for Three Months
Non-fasting blood samples were collected from rats at sacrifice.
An asterisk (*) indicates a value significantly different from the corresponding vehicle-treated group (p < 0.05).

Data in Table 1 show that this treatment is associated with dose-related lowering of plasma glucose and/or insulin levels, which is consistent with an improvement in glycemic control and insulin sensitivity by this treatment. The treatment was also associated with trends for decreased plasma lactate, cholesterol and triglyceride levels, which is also consistent with an improvement in lipid profile and metabolic control as a result of improved insulin sensitivity incurred by this treatment

What is claimed is:

1. A method for treating insulin resistance in a mammal, which comprises administering to said mammal an effective amount of a compound of formula I

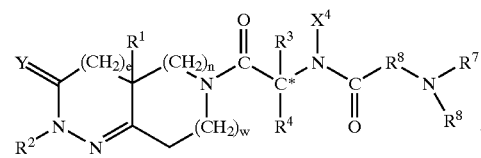

or the stereoisomeric mixtures, diastereomerically enriched, diastereomerically pure, enantiomerically enriched or enantiomerically pure isomers, or the pharmaceutically acceptable salts and prodrugs thereof, wherein e is 0 or 1;

n and w are each independently 0, 1 or 2;

provided that w and n cannot both be 0 at the same time;

Y is oxygen or sulfur;

R$^1$ is hydrogen, —CN, —(CH$_2$)$_q$N(X$^6$)C(O)X$^6$, —CH$_2$)$_q$N(X$^6$)C(O)(CH$_2$)$_t$A$^1$, —(CH$_2$)$_q$N(X$^6$)SO$_2$(CH$_2$)$_t$—A$^1$, —(CH$_2$)$_q$N(X$^6$)SO$_2$(CH$_2$)$_q$N(X$^6$)C(O)N(X$^6$)(CH$_2$)$_t$—A$^1$, —(CH$_2$)$_q$N(X$^6$)C(O)N(X$^6$)(X$^6$), —(CH$_2$)$_q$C(O)N(X$^6$)(X$^6$), —(CH$_2$)$_q$C(O)N(X$^6$)(CH$_2$)$_t$—A$^1$, —(CH$_2$)$_q$C(O)O(X$^6$), —(CH$_2$)$_q$C(O)O(CH$_2$)$_t$—A$^1$, —(CH$_2$)$_q$OX$^6$, —(CH$_2$)$_q$OC(O)X$^6$, —(CH$_2$)$_q$OC(O)(CH$_2$)$_t$—A$^1$, —(CH$_2$)$_q$OC(O)N(X$^6$)(CH$_2$)$_t$—A$^1$, —(CH$_2$)$_q$OC(O)N(X$^6$)(X$^6$), —(CH$_2$)$_q$C(O))X$^6$, —(CH$_2$)$_q$C(O)(CH$_2$)$_t$—A$^1$, —(CH$_2$)$_q$N(X$^6$)C(O)OX$^6$, —(CH$_2$)$_q$N(X$^6$)SO$_2$N(X$^6$)(X$^6$), —(CH$_2$)$_q$S(O)$_m$X$^6$, —(CH$_2$)$_q$S(O)$_m$(CH$_2$)$_t$—A$^1$, —(C$_1$-C$_{10}$)alkyl, —(CH$_2$)$_t$—A$^1$, —(CH$_2$)$_q$—(C$_3$—C$_7$)cycloalkyl, —(CH$_2$)$_q$—Y$^1$—(C$_1$-C$_6$)alkyl, —(CH$_2$)$_q$—Y$^1$—(CH$_2$)$_t$—A$^1$ or —(CH$_2$)$_q$—Y$^1$—(CH$_2$)$_t$(C$_3$-C$_7$)cycloalkyl;

where the alkyl and cycloalkyl groups in the definition of R$^1$ are optionally substituted with (C$_1$-C$_4$)alkyl, hydroxyl, (C$_1$-C$_4$)alkoxy, carboxyl, —CONH$_2$, —S(O)$_m$(C$_1$-C$_6$)alkyl, —CO$_2$(C$_1$-C$_4$)alkyl ester, 1H-tetrazol-5-yl or 1, 2 or 3 fluoro; Y$^1$ is O, S(O)$_m$, —C(O)NX$^6$—, —CH=CH—, —CH≡CH—, —N(X$^6$)C(O)—, —C(O)NX$^6$—, —C(O)O—, —OC(O)N(X$^6$)— or —OC(O)—;

q is 0, 1, 2, 3 or 4;

t is 0, 1, 2 or 3;

said (CH$_2$)$_q$ group and (CH$_2$)$_t$ group may each be optionally substituted with hydroxyl, (C$_1$-C$_4$) alkoxy, carboxyl, —CONH$_2$, —S(O)$_m$(C$_1$C$_6$)alkyl, —CO$_2$(C$_1$-C$_4$)alkyl ester, 1H-tetrazol-5-yl, 1, 2 or 3 fluoro, or 1 or 2 (C$_1$-C$_4$)alkyl;

R$^2$ is hydrogen, (C$_1$-C$_8$)alkyl, —(C$_0$-C$_3$)alkyl-(C$_3$-C$_8$) cycloalkyl, —(C$_1$-C$_4$)alkyl-A$^1$ or A$^1$;

where the alkyl groups and the cycloalkyl groups in the definition of R$^2$ are optionally substituted with hydroxyl, —C(O)OX$^6$, —C(O)N(X$^6$)(X$^6$), —N(X$^6$) (X$^6$), —S(O)$_m$(C$_1$-C$_6$)alkyl, —C(O)A$^1$, —C(O) (X$^6$), CF$_3$, CN or 1, 2 or 3 halogen;

R$^3$ is A$^1$, (C$_1$-C$_{10}$)alkyl, —(C$_1$-C$_6$)alkyl-A$^1$, —(C$_1$-C$_6$) alkyl-(C$_3$-C$_7$)cycloalkyl, —(C$_1$-C$_5$)alkyl-X$^1$—(C$_1$-C$_5$)alkyl,-(C$_1$-C$_5$)alkyl-X$^1$—(C$_0$-C$_5$)alkyl-A$^1$ or —(C$_1$-C$_5$)alkyl-X$^1$—(C$_1$-C$_5$)alkyl-(C$_3$-C$_7$) cycloalkyl;

where the alkyl groups in the definition of R$^3$ are optionally substituted with —S(O)$_m$(C$_1$-C$_6$)alkyl, —C(O)OX$^3$, 1, 2, 3, 4 or 5 halogens, or 1, 2 or 3OX$^3$;

X$^1$ is O, S(O)$_m$, —N(X$^2$)C(O)—, —C(O)N(X$^2$)—, —OC(O)—, —C(O)O—, —CX$^2$=CX$^2$—, —N(X$^2$) C(O)O—, —OC(O)N(X$^2$)— or —C≡C—;

$R^4$ is hydrogen, $(C_1-C_8)$alkyl or $(C_3-C_7)$cycloalkyl, or $R^4$ is taken together with $R^3$ and the carbon atom to which they are attached and form $(C_5-C_7)$cycloalkyl, $(C_5-C_7)$ cycloalkenyl, a partially saturated or fully saturated 4- to 8-membered ring having 1 to 4 heteroatoms independently selected from the group consisting of oxygen, sulfur and nitrogen, or is a bicyclic ring system consisting of a partially saturated or fully saturated 5- or 6-membered ring, fused to a partially saturated, fully unsaturated or fully saturated 5- or 6-membered ring, optionally having 1 to 4 heteroatoms independently selected from the group consisting of nitrogen, sulfur and oxygen;

$X^4$ is hydrogen or $(C_1-C_6)$alkyl or $X^4$ is taken together with $R^4$ and the nitrogen atom to which $X^4$ is attached and the carbon atom to which $R^4$ is attached and form a five to seven membered ring:

$R^6$ is a bond or is

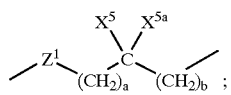

where a and b are independently 0, 1, 2 or 3;

$X^5$ and $X^{5a}$ are each independently selected from the group consisting of hydrogen, trifluoromethyl, $A^1$ and optionally substituted $(C_1-C_6)$alkyl;

the optionally substituted $(C_1-C_6)$alkyl in the definition of $X^5$ and $X^{5a}$ is optionally substituted with a substituent selected from the croup consisting of $A^1$, $OX^2$, $-S(O)_m$, $(C_1-C_6)$alkyl, $-C(O)OX^2$, $(C_3-C_7)$ cycloalkyl, $-N(X^2)(X^2)$ and $-C(O)N(X^2)(X^2)$;

or the carbon bearing $X^5$ or $X^{5a}$ forms one or two alkylene bridges with the nitrogen atom bearing $R^7$ and $R^8$ wherein each alkylene bridge contains 1 to 5 carbon atoms provided that when one alkylene bridge is formed then $X^5$ or $X^{5a}$ but not both may be on the carbon atom and $R^7$ or $R^8$ but not both may be on the nitrogen atom and further provided that when two alkylene bridges are formed then $X^5$ and $X^{5a}$ cannot be on the carbon atom and $R^7$ and $R^8$ cannot be on the nitrogen atom;

or $X^5$ is taken together with $X^{5a}$ and the carbon atom to which they are attached and form a partially saturated or fully saturated 3- to 7-membered ring, or a partially saturated or fully saturated 4- to 8-membered ring having 1 to 4 heteroatoms independently selected from the group consisting of oxygen, sulfur and nitrogen;

or $X^5$ is taken together with $X^{5a}$ and the carbon atom to which they are attached and form a bicyclic ring system consisting of a partially saturated or fully saturated 5- or 6-membered ring, optionally having 1 or 2 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

$Z^1$ is a bond, O or $N-x^2$ provided that when a and b are both 0 then $Z^1$ is not $N-X^2$ or O;

$R^7$ and $R^8$ are independently hydrogen or optionally substituted $(C_1-C_6)$alkyl;

where the optionally substituted $(C_1-C_6)$alkyl in the definition of $R^7$ and $R^8$ is optionally independently substituted with $A^1$, $-C(O)O-(C_1-C_6)$alkyl, $-S(O)_m(C_1-C_6)$alkyl, 1 to 5 halogens, 1 to 3 hydroxy, 1 to 3 $-O-C(O)(C_1-C_{10})$alkyl or 1 to 3 $(C_1-C_6)$alkoxy; or $R^7$ and $R^8$ can be taken together to form $-(CH_2)_r$-L-$(CH_2)_i$;

where L is $C(X^2)(X^2)$, $S(O)_m$ or $N(X^2)$;

$A^1$ for each occurrence is independently $(C_5-C_7)$ cycloalkenyl, phenyl or a partially saturated, fully saturated or fully unsaturated 4- to 8-membered ring optionally having 1 to 4 heteroatoms independently selected from the group consisting of oxygen, sulfur and nitrogen, a bicyclic ring system consisting of a partially saturated, fully unsaturated or fully saturated 5 or 6membered ring, optionally having 1 to 4 heteroatoms independently selected from the croup consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

$A^1$ for each occurrence is independently optionally substituted, in one or optionally both rings if $A^1$ is a bicyclic ring system, with up to three substituents, each substituent independently selected from the group consisting of F, Cl, Br, I, $OCF_3$, $OCF_2H$, $CF_3$, $CH_3$, $OCH_3$, $-O^6$, $-C(O)N(X^6)(X^6)$, $-C(O)OX^6$, oxo, $(C_1-C_6)$alkyl, nitro, cyano, benzyl, $-S(O)_m$ $(C_1-C_6)$alkyl, 1H-tetrazol-5-yl, phenyl, phenoxy, phenylalkyloxy, halophenyl, methylenedioxy, $-N(X^6)(X^6)$, $-N(X^6)C(O)(X^6)$, $-SO_2N(X^5(X^6)$, $-N(X^6)SO_2$-phenyl, $-N(X^6)SO_2X^6$, $-CONX^{11}X^{12}$, $-SO_2NX^{11}X^{12}$, $-NX^6SO_2X^{12}$, $-NX^6CONX^{11}X^{12}$, $-NX^{11}SO_2NX^{11}X^{12}$, $-NX^6C(O)X^{12}$, imidazolyl, thiazolyl and tetrazolyl, provided that if $A^1$ is optionally substituted with methylenedioxy then it can only be substituted with one methylenedioxy:

where $X^{11}$ is hydrogen or optionally substituted $(C_1-C_6)$alkyl;

the optionally substituted $(C_1-C_6)$alkyl defined for $X^{11}$ is optionally independently substituted with phenyl, phenoxy, $(C_1-C_6)$ alkoxycarbonyl, $-S(O)_m(C_1-C_6)$alkyl, 1 to 5 halogens, 1 to 3 hydroxy, 1 to 3 $(C_1-C_{10})$ alkanoyloxy or 1 to 3 $(C_1-C_6)$alkoxy;

$X^{12}$ is hydrogen, $(C_1C_6)$alkyl, phenyl, thiazolyl, imidazolyl, furyl or thienyl, provided that when $X^{12}$ is not hydrogen, $X^{12}$ is optionally substituted with one to three substituents independently selected from the group consisting of Cl, F, $CH_3$, $OCH_3$, $OCF_3$ and $CF_3$;

or $X^{11}$ and $X^{12}$ are taken together to form $-(CH_2)_r-L^1-(CH_2)_i$;

where $L^1$ is $C(X^2)(X^2)$, O, $S(O)_m$ or $N(X^2)$;

r for each occurrence is independently 1, 2 or 3;

$X^2$ for each occurrence is independently hydrogen, optionally substituted $(C_1-C_5)$alkyl, or optionally substituted $(C_3-C_7)$cycloalkyl, where the optionally substituted $(C_1-C_6)$alkyl and optionally substituted $(C_3-C_7)$cycloalkyl in the definition of $X^2$ are optionally independently substituted with $-S(O)_m(C_1-C_6)$alkyl, $-C(O)OX^3$, 1 to 5 halogens or 1–3 $OX^3$;

$X^3$ for each occurrence is independently hydrogen or $(C_1-C_6)$alkyl;

$X^5$ is independently hydrogen, optionally substituted $(C_1-C_6)$alkyl, $(C_2-C_6)$halogenated alkyl, optionally substituted $(C_3-C_7)$cycloalkyl, $(C_1-C_7)$-halogenatedcycloalkyl, where optionally substituted $(C_1-C_6)$alkyl and optionally substituted $(C_3-C_7)$ cycloalkyl in the definition of $X^6$ is optionally independently substituted by 1 or 2 $(C_1-C_4)$alkyl, hydroxyl, $(C_1-C_4)$alkoxy, carboxyl, $CONH_2$, $-S(O)_m(C_1-C_6)$ alkyl, carboxylate $(C_1-C_4)$alkyl ester, or 1H-tetrazol-5-yl; or when there are two $X^6$ groups on one atom and both $X^6$ are independently $(C_1-C_6)$alkyl, the two $(C_1-C_6)$alkyl groups may be optionally joined and, together with the atom to which the two $X^6$ groups are attached, form a 4- to 9-membered ring optionally having oxygen, sulfur or $NX^7$;

$X^7$ is hydrogen or $(C_1-C_6)$alkyl optionally substituted with hydroxyl; and m for each occurrence is independently 0, 1 or 2;

with the proviso that:

$X^6$ and $X^{12}$ cannot be hydrogen when it is attached to $C(O)$ or $SO_2$ in the form $C(O)X^6$, $C(O)X^{12}$, $SO_2X^6$ or $SO_2X^{12}$; and when $R^6$ is a bond then L is $N(X)$ and each r in the definition $-(CH_2)_r$-L-$(CH_2)_r-$ is independently 2 or 3; wherein the method additionally comprises administering to a mammal in need thereof a growth hormone releasing hormone or a functional analog thereof.

2. A method for increasing levels of endogenous growth hormone, which comprises administering to a human or other animal in need thereof effective amounts of a functional somatostatin antagonist and a compound of formula I

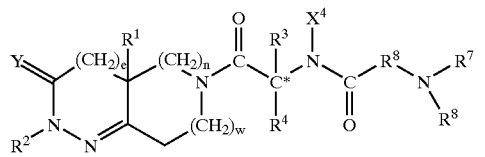

or the stereoisomeric mixtures, diastereomerically enriched, diastereomerically pure, enantiomerically enriched or enantiomerically pure isomers or the pharmaceutically acceptable salts and prodrugs thereof, wherein a is 0 or 1;

n and w are each independently 0, 1 or 2;

provided that w and n cannot both be 0 at the same time;

Y is oxygen or sulfur;

$R^1$ is hydrogen, CN, $-(CH_2)_qN(X^6)C(O)X^6$, $-(CH_2)_qN(X^6)C(O)(CH_2)_r-A^1$, $-(CH_2)_qN(X^6)SO_2(CH_2)_r-A^1$, $-(CH_2)_qN(X^6)SO_2X^6$, $-(CH_2)_qN(O)C(O)N(X^6)(CH_2)_r-A^1$, $-(CH_2)_qN(X^6)C(O)N(X^6)(X^6)$, $-(CH_2)_qC(O)N(X^6)(X^6)$, $-(CH_2)_qC(O)N(X^6)(CH_2)_r-A^1$, $-(CH_2)_qC(O)OX^6$, $-(CH_2)_qC(O)O(CH_2)_r-A^1$, $-(CH_2)_qOX^6$, $-(CH_2)_qOC(O)X^6$, $-(CH_2)_qOC(O)(CH_2)_r-A^1$, $-(CH_2)_qOC(O)N(X^6)(CH_2)_r-A^1$, $-(CH_2)_qOC(O)N(X^6)(X^6)$, $-(CH_2)_qC(O)X^5$, $-(CH_2)_qC(O)(CH_2)_r-A^1$, $-(CH_2)_qN(X^6)C(O)OX^6$, $-(CH_2)_qN(X^6)SO_2N(X^6)(X^5)$, $-(CH_2)_qS(O)_mX^6$, $-(CH_2)_qS(O)_m(CH_2)_r-A^1$, $-(C_1-C_{10})$alkyl, $-(CH_2)_r-A^1$, $-(CH_2)_q-(C_3-C_7)$cycloalkyl, $-(CH_2)_q-Y^1-(C_1-C_6)$alkyl, $-(CH_2)_q-Y^1-(CH_2)_r-A^1$ or $-(CH_2)_q-Y^1-(CH_2)_r(C_3-C_7)$cycloalkyl;

where the alkyl and cycloalkyl groups in the definition of $R^1$ are optionally substituted with $(C_1-C_4)$alkyl, hydroxyl, $(C_1-C_4)$alkoxy, carboxyl, $-CONH_2$, $-S(O)_m(C_1-C_6)$alkyl, $-CO_2(C_1-C_4)$alkyl ester, 1H-tetrazol-5-yl or 1, 2 or 3 fluoro;

$Y^1$ is O, $S(O)_m$, $-C(O)NX^6-$, $-CH=CH-$, $-C\equiv CH-$, $-N(O)C(O)-$, $-C(O)NX^6-$, $-C(O)O-$, $-OC(O)N(X^6)-$ or $-OC(O)-$;

q is 0, 1, 2, 3 or 4;

t is 0, 1, 2 or 3;

said $(CH_2)_q$ group and $(CH_2)_t$ group may each be optionally substituted with hydroxyl, $(C_1-C_4)$ alkoxy, carboxyl, $-CONH_2$, $-S(O)_m(C_1-C_6)$alkyl, $-CO_2(C_1-C_4)$alkyl ester, 1H-tetrazol-5-yl, 1, 2 or 3 fluoro, or 1 or 2 $(C_1-C_4)$alkyl;

$R^2$ is hydrogen, $(C_1-C_8)$alkyl, $-(CO-C_3)$alkyl-$(C-C_8)$ cycloalkyl, $-(C_1-C_4)$alkyl-$A^1$ or $A^1$;

where the alkyl groups and the cycloalkyl groups in the definition of $R^2$ are optionally substituted with hydroxyl, $-C(O)OX^6$, $-C(O)N(X^6)(X^6)$, $-N(X^6)(X^6)$, $-S(O)_m(C_1-C_6)$alkyl, $-C(O)A^1$, $-C(O)(X^6)$, $CF_3$, CN or 1, 2 or 3 halogen;

$R^3$ is $A^1$, $(C_1-C_{10})$alkyl, $-(C_1-Cs)$alkyl-$A^1$, $-(C_1-C_6)$ alkyl-$(C_3-C_7)$cycloalkyl, $-(C_1-C_5)$alkyl-$X^1-$ $(C_1-C_5)$alkyl, $-(C_1-C_5)$alkyl-$X^1-(C_0-C_5)$alkyl-$A^1$ or $-(C_1-C_5)$alkyl-$X^1-(C_1-C_5)$alkyl-$(C_3-C_7)$ cycloalkyl;

where the alkyl groups in the definition of $R^3$ are optionally substituted with $-S(O)_m(C_1-C_6)$alkyl, $-C(O)OX^3$, 1, 2, 3, 4 or 5 halogens, or 1, 2 or 3 $OX^3$;

$X^1$ is O, $S(O)_m$, $-N(X^2)C(O)-$, $-C(O)N(X^2)-$, $-OC(O)-$, $-C(O)O-$, $-CX^2=CX^2-$, $-N(X^2)C(O)O-$, $-OC(O)N(X^2)-$ or $-C\equiv C-$;

$R^4$ is hydrogen, $(C_1-C_6)$alkyl or $(C_3-C_7)$cycloalkyl, or $R^4$ is taken together with $R^3$ and the carbon atom to which they are attached and form $(C_5-C_7)$cycloalkyl, $(C_5-C_7)$ cycloalkenyl, a partially saturated or fully saturated 4- to 8-membered ring having 1 to 4 heteroatoms independently selected from the group consisting of oxygen, sulfur and nitrogen, or is a bicyclic ring system consisting of a partially saturated or fully saturated 5- or 6-membered ring, fused to a partially saturated, fully unsaturated or fully saturated 5- or 6-membered ring, optionally having 1 to 4 heteroatoms independently selected from the group consisting of nitrogen, sulfur and oxygen;

$X^4$ is hydrogen or $(C_1-C_6)$alkyl or $X^4$ is taken together with $R^4$ and the nitrogen atom to which $X^4$ is attached and the carbon atom to which $R^4$ is attached and form a five to seven membered ring;

$R^6$ is a bond or is

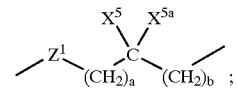

where a and b are independently 0, 1, 2 or 3;

$X^5$ and $X^{5a}$ are each independently selected from the group consisting of hydrogen, trifluoromethyl, $A^1$ and optionally substituted $(C_1-C_6)$alkyl;

the optionally substituted $(C_1-C_6)$alkyl in the definition of $X^5$ and $X^{5a}$ is optionally substituted with a substituent selected from the group consisting of $A^1$, $OX^2$, $-S(O)_m(C_1-C_6)$alkyl, $-C(O)OX^2$, $(C_3-C_7)$cycloalkyl, $-N(X^2)(X^2)$ and $-C(O)N(X^2)(X^2)$;

or the carbon bearing $X^5$ or $X^{5a}$ forms one or two alkylene bridges with the nitrogen atom bearing $R^7$ and $R^8$ wherein each alkylene bridge contains 1 to 5 carbon atoms, provided that when one alkylene bridge is formed then $X^5$ or $X^{5a}$ but not both may be on the carbon atom and $R^7$ or $R^8$ but not both may be on the nitrogen atom and further provided that when two alkylene bridges are formed then $X^5$ and $X^{5a}$ cannot be on the carbon atom and $R^7$ and $R^8$ cannot be on the nitrogen atom;

or $X^5$ is taken together with $X^{5a}$ and the carbon atom to which they are attached and form a partially saturated or fully saturated 3- to 7-membered ring, or a partially saturated or fully saturated 4- to 8-membered ring having 1 to 4 heteroatoms independently selected from the group consisting of oxygen, sulfur and nitrogen;

or $X^5$ is taken together with $X^{5a}$ and the carbon atom to which they are attached and form a bicyclic ring system consisting of a partially saturated or fully saturated 5- or 6-membered ring, optionally having 1 or 2 heteroatoms independently selected from the group consisting of nitrogen, sulfur and oxygen, fused to a partially saturated, fully saturated or fully unsaturated 5- or 6membered ring, optionally having 1 to 4 heteroatoms independently selected from the group consisting of nitrogen, sulfur and oxygen;

$Z^1$ is a bond, O or N—$X^2$, provided that when a and b are both 0 then $Z^1$ is not N—$X^2$ or O;

$R^7$ and $R^8$ are independently hydrogen or optionally substituted $(C_1$–$C_6)$alkyl;

where the optionally substituted $(C_1$–$C_6)$alkyl in the definition of $R^7$ and $R^6$ is optionally independently substituted with $A^1$, —C(O)O—$(C_1$–$C_6)$alkyl, —S(O)$_m(C_1$–$C_6)$alkyl, 1 to 5 halogens, 1 to 3 hydroxy, 1 to 3 —O—C(O)$(C_1$–$C_{10})$alkyl or 1 to 3 $(C_1$–$C_6)$alkoxy; or $R^7$ and $R^8$ can be taken together to form —(CH$_2$)$_r$-L-(CH$_2$)—;

where L is C($X^2$)($X^2$), S(O)$_m$, or N($X^2$);

$A^1$ for each occurrence is independently $(C_5$–$C_7)$cycloalkenyl, phenyl or a partially saturated, fully saturated or fully unsaturated 4- to 8-membered ring optionally having 1 to 4 heteroatoms independently selected from the group consisting of oxygen, sulfur and nitrogen, a bicyclic ring system consisting of a partially saturated, fully unsaturated or fully saturated 5- or 6-membered ring, optionally having 1 to 4 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

$A^1$ for each occurrence is independently optionally substituted, in one or optionally both rings if $A^1$ is a bicyclic ring system, with up to three substituents, each substituent independently selected from the group consisting of F, Cl, Br, I, OCF$_3$, OCF$_2$H, CF$_3$, CH$_3$, OCH$_3$, —O$X^6$, —C(O)N($X^6$)($X^6$), —C(O)O$X^6$, oxo, $(C_1$–$C_6)$alkyl, nitro, cyano, benzyl, —S(O)$_m(C_1$–$C_6)$alkyl, 1H-tetrazol-5-yl, phenyl, phenoxy, phenylalkyloxy, halophenyl, methylenedioxy, —N($X^6$)($X^6$), —N($X^6$)C(O)($X^6$), —SO$_2$N($X^6$)($X^6$), —N($X^6$)SO$_2$-phenyl, —N($X^6$)SO$_2X^6$, —CON$X^{11}X^{12}$, —SO$_2$N$X^{11}X^{12}$, —N$X^6$SO$_2X^{12}$, —N$X^6$CON$X^{11}X^{12}$, —N$X^6$SO$_2$N$X^{11}X^{12}$, —N$X^6$C(O)$X^{12}$, imidazolyl, thiazolyl and tetrazolyl, provided that if $A^1$ is optionally substituted with methylenedioxy then it can only be substituted with one methylenedioxy;

where $X^{11}$ is hydrogen or optionally substituted $(C_1$–$C_6)$alkyl;

the optionally substituted $(C_1$–$C_6)$alkyl defined for $X^{11}$ is optionally independently substituted with phenyl, phenoxy, $(C_1$–$C_6)$alkoxycarbonyl, —S(O)$_m(C_1$–$C_6)$alkyl, 1 to 5 halogens, 1 to 3 hydroxy, 1 to 3 $(C_1$–$C_{10})$alkanoyloxy or 1 to 3 $(C_1$–$C_6)$alkoxy;

$X^{12}$ is hydrogen, $(C_1$–$C_6)$alkyl, phenyl, thiazolyl, imidazolyl, furyl or thienyl, provided that when $X^{12}$ is not hydrogen, $X^{12}$ is optionally substituted with one to three substituents independently selected from the group consisting of Cl, F, CH$_3$, OCH$_3$, OCF$_3$ and CF$_3$;

or $X^{11}$ and $X^{12}$ are taken together to form —(CH$_2$)$_r$—L$^1$—(CH$_2$)$_r$—;

where L$_1$ is C($X^2$)($X^2$), O, S(O)$_m$ or N($X^2$);

r for each occurrence is independently 1, 2 or 3;

$X^2$ for each occurrence is independently hydrogen, optionally substituted $(C_1$–$C_6)$alkyl, or optionally substituted $(C_3$–$C_7)$cycloalkyl, where the optionally substituted $(C_1$–$C_6)$alkyl and optionally substituted $(C_3$–$C_7)$cycloalkyl in the definition of $X^2$ are optionally independently substituted with —S(O)$_m(C_1$–$C_6)$alkyl, —C(O)O$X^3$, 1 to 5 halogens or 1–3 O$X^3$;

$X^3$ for each occurrence is independently hydrogen or $(C_1$–$C_6)$alkyl;

$X^6$ is independently hydrogen, optionally substituted $(C_1$–$C_8)$alkyl, $(C_2$–$C_6)$halogenated alkyl optionally substituted $(C_3$–$C_7)$cycloalkyl, $(C_3$–$C_7)$-halogenatedcycloalkyl, where optionally substituted $(C_1$–$C_6)$alkyl and optionally substituted $(C_3$–$C_7)$cycloalkyl in the definition of $X^6$ is optionally independently substituted by 1 or 2 $(C_1$–$C_4)$alkyl, hydroxyl, $(C_1$–$C_4)$alkoxy, carboxyl, CONH$_2$, —S(O)$_m(C_1$–$C_6)$alkyl, carboxylate $(C_1$–$C_4)$alkyl ester, or 1H-tetrazol-5-yl; or when there are two $X^6$ groups on one atom and both $X^6$ are independently $(C_1$–$C_6)$alkyl, the two $(C_1C_6)$alkyl groups may be optionally joined and, together with the atom to which the two $X^6$ groups are attached, form a 4 to 9-membered ring optionally having oxygen, sulfur or N$X^7$;

$X^7$ is hydrogen or $(C_1C_6)$alkyl optionally substituted with hydroxyl; and m for each occurrence is independently 0, 1 or 2;

with the proviso that:

$X^6$ and $X^{12}$ cannot be hydrogen when it is attached to C(O) or SO$_2$ in the form C(O)$X^6$, C(O)$X^{12}$, SO$_2X^6$ or SO$_2X^{12}$; and when $R^6$ is a bond then L is N(O) and each r in the definition —(CH$_2$)$_r$—L—(CH$_2$)$_r$— is independently 2 or 3.

3. A method of treating congestive heart failure, obesity or frailty associated with aging, which comprises administering to a mammal in need thereof effective amounts of a functional somatostatin antagonist and a compound of formula I

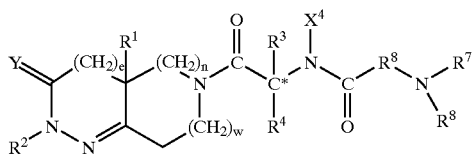

I or the stereoisomeric mixtures, diastereomerically enriched, diastereomerically pure, enantiomerically enriched or enantiomerically pure isomers or the pharmaceutically acceptable salts and prodrugs thereof,
wherein
e is 0 or 1;
n and w are each independently 0, 1 or 2;
provided that w and n cannot both be 0 at the same time;
Y is oxygen or sulfur;
$R^1$ is hydrogen, —CN, $(CH_2)_qN(X^6)C(O)X^6$, —$(CH_2)_qN(X^6)C(O)(CH_2)_tA^1$, —$(CH_2)_qN(X^6)SO_2(CH_2)_t$—$A^1$, —$(CH_2)_qN(X^6))SO_2X^6$, —$(CH_2)_qN(X^6)C(O)N(X^6)$ $(CH_2)_t$—$A^1$, —$(CH_2)_qN(X^6)C(O)N(X^6)(X^6)$, —$(CH_2)_qC(O)N(X^6)(X^6)$, —$(CH_2)_qC(O)N(X^6)(CH_2)_t$—$A^1$, —$(CH_2)_qC(O)OX^6$, —$(CH_2)_qC(O)O(CH_2)_t$—$A^1$, —$(CH_2)_qOX^6$, —$(CH_2)_qOC(O)X^6$, —$(CH_2)_qOC(O)$ $(CH_2)_t$—$A^1$, —$(CH_2)_qOC(O)N(X^6)(CH_2)_t$—$A^1$, —$(CH_2)_qOC(O)N(X^6)(X^6)$, —$(CH_2)_qC(O)X^6$, —$(CH_2)_qC(O)(CH_2)_t$—$A^1$, —$(CH_2)_qN(X^6)C(O)OX^6$, —$(CH_2)_qN(X^6)SO_2N(X^6)(X^6)$, —$(CH_2)_qS(O)_mX^6$, —$(CH_2)_qS(O)_m(CH_2)_tA^1$, —$(C_1-C_{10})$alkyl, —$(CH_2)_t$—$A^1$, —$(CH_2)_q$—$(C_3-C_7)$cycloalkyl, —$(CH_2)_q$—$Y^1$—$(C_1-C_6)$alkyl, —$(CH_2)_q$—$Y^1$—$(CH_2)_t$—$A^1$ or —$(CH_2)_q$—$Y^1$—$(CH_2)_t$—$(C_3-C_7)$cycloalkyl;
where the alkyl and cycloalkyl groups in the definition of $R^1$ are optionally substituted with $(C_1-C_4)$alkyl, hydroxyl, $(C_1-C_4)$alkoxy, carboxyl, —$CONH_2$, —$S(O)_m(C_1-C_6)$alkyl, —$CO_2(C_1-C_4)$alkyl ester, 1H-tetrazol-5-yl or 1, 2 or 3 fluoro;
$Y^1$ is O, $S(O)_m$, —C(O)N)O—, —CH=CH—, —CH≡CH—, —$N(X^6)C(O)$—, —$C(O)NX^6$—, —C(O)O—, —OC(O)$N(X^6)$— or —OC(O)—;
q is 0, 1, 2, 3 or 4;
t is 0, 1, 2 or 3;
said $(CH_2)_q$ group and $(CH_2)_t$ group may each be optionally substituted with hydroxyl, $(C_1-C_4)$alkoxy, carboxyl, —$CONH_2$, —$S(O)_m(C_1-C_4)$alkyl, —$CO_2(C_1-C_4)$alkyl ester, 1H-tetrazol-5-yl, 1, 2 or 3 fluoro, or 1 or 2 $(C_1-C_4)$alkyl;
$R^2$ is hydrogen, $(C_1-C_8)$alkyl, —$(C_0-C_3)$alkyl-$(C_3-C_8)$ cycloalkyl, —$(C_1-C_4)$alkyl-$A^1$ or $A^1$;
where the alkyl groups and the cycloalkyl groups in the definition of $R^2$ are optionally substituted with hydroxyl, —$C(O)OX^6$, —$C(O)N(X^6)(X^6)$, —$N(X^6)$ $(X^6)$, —$S(O)_m(C_1-C_6)$alkyl, —$C(O)A^1$, —C(O) $(X^6)$, $CF_3$, CN or 1, 2 or 3 halogen;
$R^3$ is $A^1$, $(C_1-C_{10})$alkyl, —$(C_1-C_6)$alkyl—$A^1$, —$(C_1-C_6)$ alkyl-$(C_3-C_7)$cycloalkyl, —$(C_1-C_5)$alkyl-$X^1$— $(C_1-C_5)$alkyl, —$(C_1-C_5)$alkyl-$X^1$—$(C_0-C_5)$alkyl—$A^1$ or —$(C_1-C_5)$alkyl-$X^1$—$(C_1-C_5)$alkyl-$(C_3-C_7)$ cycloalkyl;
where the alkyl groups in the definition of $R^3$ are optionally substituted with —$S(O)_m(C_1-C_6)$alkyl, —$C(O)OX^3$, 1, 2, 3, 4 or 5 halogens, or 1, 2 or $3OX^3$;
$X^1$ is O, $S(O)_m$, —$N(X^2)C(O)$—, —$C(O)N(X^2)$—, —OC(O)—, —$C(O)O$—, —$CX^2$=$CX^2$—, —$N(X^2)$ C(O)O—, —OC(O)N($X^2$)— or —C≡C—;

$R^4$ is hydrogen, $(C_1-C_6)$alkyl or $(C_3-C_7)$cycloalkyl, or $R^4$ is taken together with $R^3$ and the carbon atom to which they are attached and form $(C_5-C_7)$cycloalkyl, $(C_5-C_7)$ cycloalkenyl, a partially saturated or fully saturated 4- to 8 membered ring having 1 to 4 heteroatoms independently selected from the group consisting of oxygen, sulfur and nitrogen, or is a bicyclic ring system consisting of a partially saturated or fully saturated 5- or 6-membered ring, fused to a partially saturated, fully unsaturated or fully saturated 5- or 6-membered ring, optionally having 1 to 4 heteroatoms independently selected from the group consisting of nitrogen, sulfur and oxygen;
$X^4$ is hydrogen or $(C_1-C_6)$alkyl or $X^4$ is taken together with $R^4$ and the nitrogen atom to which $X^4$ is attached and the carbon atom to which $R^4$ is attached and form a five to seven membered ring;
$R^6$ is a bond or is

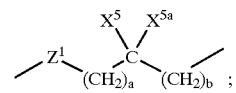

where a and b are independently 0, 1, 2 or 3;
$X^5$ and $X^{5a}$ are each independently selected from the group consisting of hydrogen, trifluoromethyl, $A^1$ and optionally substituted $(C_1-C_6)$alkyl;
the optionally substituted $(C_1-C_6)$alkyl in the definition of $X^5$ and $X^{5a}$ is optionally substituted with a substituent selected from the group consisting of $A^1$, $OX^2$, —$S(O)_m(C_1-C_6)$alkyl, —$C(O)OX^2$, $(C_3-C_7)$ cycloalkyl, —$N(X^2)(X^2)$ and —$C(O)N(X^2)(X^2)$;
or the carbon bearing $X^5$ or $X^{5a}$ forms one or two alkylene bridges with the nitrogen atom bearing $R^7$ and $R^8$ wherein each alkylene bridge contains 1 to 5 carbon atoms, provided that when one alkylene bridge is formed then $X^5$ or $X^{5a}$ but not both may be on the carbon atom and $R^7$ or $R^8$ but not both may be on the nitrogen atom and further provided that when two alkylene bridges are formed then $X^5$ and $X^{5a}$ cannot be on the carbon atom and $R^7$ and $R^8$ cannot be on the nitrogen atom;
or $X^5$ is taken together with $X^{5a}$ and the carbon atom to which they are attached and form a partially saturated or fully saturated 3- to 7-membered ring, or a partially saturated or fully saturated 4 to 8-membered ring having 1 to 4 heteroatoms independently selected from the group consisting of oxygen, sulfur and nitrogen;
or $X^5$ is taken together with $X^{5a}$ and the carbon atom to which they are attached and form a bicyclic ring system consisting of a partially saturated or fully saturated 5- or 6-membered ring, optionally having 1 or 2 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;
$Z^1$ is a bond, O or N—$X^2$, provided that when a and b are both 0 then $Z^1$ is not N—$X^2$ or O;
$R^7$ and $R^8$ are independently hydrogen or optionally substituted $(C_1-C_6)$alkyl;
where the optionally substituted $(C_1-C_6)$alkyl in the definition of $R^7$ and $R^8$ is optionally independently substituted with $A^1$, —C(O)O—$(C_1-C_6)$alkyl, —S(O)$_m$(C$_1$–C$_6$)alkyl, 1 to 5 halogens, 1 to 3 hydroxy, 1 to 3 —O—C(O)(C$_1$–C$_{10}$)alkyl or 1 to 3 (C$_1$–C$_6$)alkoxy; or R$^7$ and R$^8$ can be taken together to form —(CH$_2$)$_r$—L—(CH$_2$)$_r$—;

where L is C(X$^2$)(X$^2$), S(O)$_m$ or N(X$^2$);

A$^1$ for each occurrence is independently (C$_5$–C$_7$) cycloalkenyl, phenyl or a partially saturated, fully saturated or fully unsaturated 4- to 8-membered ring optionally having 1 to 4 heteroatoms independently selected from the group consisting of oxygen, sulfur and nitrogen, a bicyclic ring system consisting of a partially saturated, fully unsaturated or fully saturated 5- or 6-membered ring, optionally having 1 to 4 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

A$^1$ for each occurrence is independently optionally substituted, in one or optionally both rings if A$^1$ is a bicyclic ring system, with up to three substituents, each substituent independently selected from the group consisting of F, Cl, Br, I, OCF$_3$, OCF$_2$H, CF$_3$, CH$_3$, OCH$_3$, —OX$^6$, —C(O)N(X$^6$)(X$^6$), —C(O)OX$^6$, oxo, (C$_1$–C$_6$)alkyl, nitro, cyano, benzyl, —S(O)$_m$(C$_1$–C$_6$)alkyl, 1H-tetrazol-5-yl, phenyl, phenoxy, phenylalkyloxy, halophenyl, methylenedioxy, —N(X$^6$)(X$^6$), —N(X$^6$)C(O)(X$^6$), —SO$_2$N(X$^6$)(X$^6$), —N(X$^6$)SO$_2$-phenyl, —N(X$^6$)SO$_2$X$^6$, —CONX$^{11}$X$^{12}$, —SO$_2$NX$^{11}$X$^{12}$, —NX$^6$SO$_2$X$^{12}$, —NX$^6$CONX$^{11}$X$^{12}$, —NX$^6$SO$_2$NX$^{11}$X$^{12}$, —NX$^6$C(O)X$^{12}$, imidazolyl, thiazolyl and tetrazolyl, provided that if A$^1$ is optionally substituted with methylenedioxy then it can only be substituted with one methylenedioxy;

where X$^{11}$ is hydrogen or optionally substituted (C$_1$–C$_6$)alkyl;

the optionally substituted (C$_1$–C$_6$)alkyl defined for X$^{11}$ is optionally independently substituted with phenyl, phenoxy, (C$_1$–C$_6$)alkoxycarbonyl, —S(O)$_m$(C$_1$–C$_6$)alkyl, 1 to 5 halogens, 1 to 3 hydroxy, 1 to 3 (C$_1$–C$_{10}$)alkanoyloxy or 1 to 3 (C$_1$–C$_6$)alkoxy;

X$^{12}$ is hydrogen, (C$_1$–C$_6$)alkyl, phenyl, thiazolyl, imidazolyl, furyl or thienyl, provided that when X$^{12}$ is not hydrogen, X$^{12}$ is optionally substituted with one to three substituents independently selected from the group consisting of Cl, F, CH$_3$, OCH$_3$, OCF$_3$ and CF$_3$;

or X$^{11}$ and X$^{12}$ are taken together to form —(CH$_2$)$_r$—L$^1$—(CH$_2$)$_r$;

where L$^1$ is C(X$^2$)(X$^2$), O, S(O)$_m$ or N(X$^2$);

r for each occurrence is independently 1, 2 or 3;

X$^2$ for each occurrence is independently hydrogen, optionally substituted (C$_1$–C$_6$)alkyl, or optionally substituted (C$_3$–C$_7$)cycloalkyl, where the optionally substituted (C$_1$–C$_6$)alkyl and optionally substituted (C$_3$–C$_7$)cycloalkyl in the definition of X$^2$ are optionally independently substituted with —S(O)$_m$(C$_1$–C$_6$)alkyl, —C(O)OX$^3$, 1 to 5 halogens or 1–3 OX$^3$;

X$^3$ for each occurrence is independently hydrogen or (C$_1$–C$_6$)alkyl;

X$^6$ is independently hydrogen, optionally substituted (C$_1$–C$_6$)alkyl, (C$_2$–C$_6$)halogenated alkyl, optionally substituted (C$_3$–C$_7$)cycloalkyl, (C$_3$–C$_7$)-halogenatedcycloalkyl, where optionally substituted (C$_1$–C$_6$)alkyl and optionally substituted (C$_3$–C$_7$) cycloalkyl in the definition of X$^6$ is optionally independently substituted by 1 or 2 (C$_1$–C$_4$)alkyl, hydroxyl, (C$_1$–C$_4$)alkoxy, carboxyl, CONH$_2$, —S(O)$_m$(C$_1$–C$_6$) alkyl, carboxylate (C$_1$–C$_4$)alkyl ester, or 1H-tetrazol-5-yl; or when there are two X$^6$ groups on one atom and both X$^6$ are independently (C$_1$–C$_6$)alkyl, the two (C$_1$–C$_6$)alkyl groups may be optionally joined and, together with the atom to which the two X$^6$ groups are attached, form a 4- to 9-membered ring optionally having oxygen, sulfur or NX$^7$;

X$^7$ is hydrogen or (C$_1$–C$_6$)alkyl optionally substituted with hydroxyl; and m for each occurrence is independently 0, 1 or 2;

with the proviso that:

X$^6$ and X$^{12}$ cannot be hydrogen when it is attached to C(O) or SO$_2$ in the form C(O)X$^6$, C(O)X$^{12}$, SO$_2$X$^6$ or SO$_2$X$^{12}$; and when R$^6$ is a bond then L is N(X$^2$) and each r in the definition —(CH$_2$)$_r$—L-(CH$_2$)$_r$— is independently 2 or 3.

4. A method according to claim 3 wherein said functional somatostatin antagonist is an alpha-2 adrenergic agonist.

5. A method according to claim 4 wherein said alpha-2 adrenergic agonist is selected from the group consisting of clonidine, xylazine and medetomidine.

6. A method according to claim 5 wherein said compound of formula I is 2-amino-N-[2-(3a-(R)-benzyl-2-methy-3-oxo-2,3,3a,4,6,7-hexahydro-pyrazolo-[4,3-c]pyridin-5-yl)-1-(R)-benzyloxymethyl-2-oxo-ethyl]-isobutyramide L-tartaric acid salt.

7. A pharmaceutical composition which comprises a pharmaceutically acceptable carrier, an amount of an alpha-2 adrenergic agonist and an amount of a compound of formula I

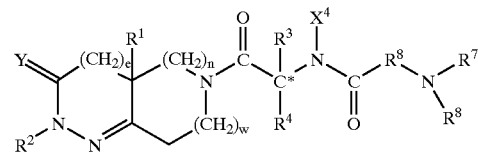

or the stereoisomeric mixtures, diastereomerically enriched, diastereomerically pure, enantiomerically enriched or enantiomerically pure isomers or the pharmaceutically acceptable salts and prodrugs thereof, wherein e is 0 or 1;

n and w are each independently 0, 1 or 2;

provided that w and n cannot both be 0 at the same tme;

Y is oxygen or sulfur;

R$^1$ is hydrogen, —CN, —(CH$_2$)$_q$N(X$^6$)C(O)X$^6$, —(CH$_2$)$_q$N(X$^6$)C(O)(CH$_2$)$_t$—A$^1$, —(CH$_2$)$_q$N(X$^6$)SO$_2$(CH$_2$)$_t$—A$^1$, —(CH$_2$)$_q$N(X$^6$)SO$_2$X$^6$, —(CH$_2$)$_q$N(X$^6$)C(O)N(X$^6$) (CH$_2$)$_t$—A$^1$, —(CH$_2$)$_q$N(X$^6$)C(O)N(X$^6$)(X$^6$), —(CH$_2$)$_q$C(O)N(X$^6$)(X$^6$), —(CH$_2$)$_q$C(O)N(X$^6$)(CH$_2$)$_t$—A$^1$, —(CH$_2$)$_q$C(O)OX$^6$, —(CH$_2$)$_q$C(O)O(CH$_2$)$_t$—A$^1$, —(CH$_2$)$_q$OX$^6$, —(CH$_2$)$_q$OC(O)X$^6$, —(CH$_2$)$_q$OC(O) (CH$_2$)$_t$—A$^{11}$, —(CH$_2$)$_q$OC(O)N(X$^6$)(CH$_2$)$_t$—A$^1$, —(CH$_2$)$_q$OC(O)N(X$^6$)(X$^6$), —(CH$_2$)$_q$C(O)X$^6$, —(CH$_2$)$_q$C(O)(CH$_2$)$_t$—A$^1$, (CH$_2$)$_t$N(X$^6$)C(O)OX$^6$—(CH$_2$)$_q$N(X$^8$)SO$_2$N(X$^6$)(X$^6$), —(CH$_2$)$_q$S(O)$_m$X$^6$, —(CH$_2$)$_q$S(O)$_m$(CH$_2$)$_t$—A$^1$, —(C$_1$–C$_{10}$)alkyl, —(CH$_2$)$_t$—A$^1$, —(CH$_2$)$_q$—(C$_3$–C$_7$)cycloalkyl, —(CH$_2$)$_1$—Y$^1$—(C$_1$–C$_6$)alkyl, —(CH$_2$)$_q$—Y$^1$—(CH$_2$)$_t$—A$^1$ or —(CH$_2$)$_q$—Y$^1$—(CH$_2$)$_t$—(C$_3$–C$_7$) cycloalkyl;

where the alkyl and cycloalkyl groups in the definition of R$^1$ are optionally substituted with (C$_1$–C$_4$)alkyl, hydroxyl, (C$_1$–C$_4$)alkoxy, carboxyl, —CONH$_2$, —S(O)$_m$(C$_1$–C$_6$)alkyl, —CO$_2$(C$_1$–C$_4$)alkyl ester, 1H-tetrazol-5-yl or 1, 2 or 3 fluoro;

Y$^1$ is O, S(O)$_m$, —C(O)NX$^6$—, —CH═CH—, —CH≡CH—, —N(X$^6$)C(O)—, —C(O)NX$^6$—, —C(O)O—, —OC(O)N(X$^6$)— or —OC(O)—;

q is 0, 1, 2, 3 or 4;

t is 0, 1, 2 or 3;

said (CH$_2$)$_q$ group and (CH$_2$)$_t$ group may each be optionally substituted with hydroxyl, (C$_1$–C$_4$) alkoxy, carboxyl, CONH$_2$, —S(O)$_m$(C$_1$–C$_4$)alkyl, —CO$_2$(C$_1$–C$_4$)alkyl ester, 1H-tetrazol-5-yl, 1, 2 or 3 fluoro, or 1 or 2 (C$_1$–C$_4$)alkyl;

R$^2$ is hydrogen, (C$_1$–C$_6$)alkyl, —(C$_0$–C$_3$)alkyl-(C$_3$–C$_8$) cycloalkyl, —(C$_1$–C$_4$)alkyl—A$^1$ or A$^1$;

where the alkyl groups and the cycloalkyl groups in the definition of R$^2$ are optionally substituted with hydroxyl, —C(O)OX$^6$, —C(O)N(X$^6$)(X$^6$), —N(X$^6$)(X$^6$), —S(O)$_m$(C$_1$–C$_6$)alkyl, —C(O)A$^1$, —C(O) (X$^6$), CF$_3$, CN or 1, 2 or 3 halogen;

R$^3$ is A$^1$, (C$_1$–C$_{10}$)alkyl, —(C$_1$–C$_6$)alkyl-A$^1$, —(C$_1$–C$_6$) alkyl-(C$_3$–C$_7$)cycloalkyl, —(C$_1$–C$_5$)alkyl-X$^1$—(C$_1$–C$_5$)alkyl, —(C$_1$–C$_5$)alkyl-X$^1$—(C$_0$–C$_5$)alkyl-A$^1$ or —(C$_1$–C$_5$)alkyl-X$^1$—(C$_1$–C$_5$)alkyl-(C$_3$–C$_7$) cycloalkyl;

where the alkyl groups in the definition of R$^3$ are optionally substituted with —S(O)$_m$(C$_1$–C$_6$)alkyl, —C(O)OX$^3$, 1, 2, 3, 4 or 5 halogens, or 1, 2 or 3 OX$^3$;

X$^1$ is O, S(O)$_m$, —N(X$^2$)C(O)—, —C(O)N(X$^2$)—, —OC(O)—, —C(O)O—, —CX$^2$═CX$^2$—, —N(X$^2$) C(O)O—, —OC(O)N(X$^2$)— or —C≡C—;

R$^4$ is hydrogen, (C$_1$–C$_6$)alkyl or (C$_3$–C$_7$)cycloalkyl, or R$^4$ is taken together with R$^3$ and the carbon atom to which they are attached and form (C$_5$–C$_7$)cycloalkyl, (C$_5$–C$_7$) cycloalkenyl, a partially saturated or fully saturated 4- to 8-membered ring having 1 to 4 heteroatoms independently selected from the group consisting of oxygen, sulfur and nitrogen, or is a bicyclic ring system consisting of a partially saturated or fully saturated 5 or 6-membered ring, fused to a partially saturated, fully unsaturated or fully saturated 5- or 6-membered ring, optionally having 1 to 4 heteroatoms independently selected from the group consisting of nitrogen, sulfur and oxygen;

X$^4$ is hydrogen or (C$_1$–C$_6$)alkyl or X$^4$ is taken together with R4 and the nitrogen atom to which X$^4$ is attached and the carbon atom to which R4 is attached and form a five to seven membered ring;

R″ is a bond or is

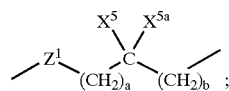

where a and b are independently 0, 1, 2 or 3;

X$^5$ and X$_{5a}$ are each independently selected from the group consisting of hydrogen, trifluoromethyl, A$^1$ and optionally substituted (C$_1$–C$_6$)alkyl;

the optionally substituted (C$_1$–C$_6$)alkyl in the definition of X$^5$ and X$^{5a}$ is optionally substituted with a substituent selected from the group consisting of A$^1$, OX$^2$, —S(O)$_m$(C$_1$–C$_6$)alkyl, —C(O)OX$^2$, (C$_3$–C$_7$)cycloalkyl, —N(X$^2$)(X$^2$) and —C(O)N (X$^2$)(X$^2$);

or the carbon bearing X$^5$ or X$^{5a}$ forms one or two alkylene bridges with the nitrogen atom bearing R$^7$ and R$^8$ wherein each alkylene bridge contains 1 to 5 carbon atoms, provided that when one alkylene bridge is formed then X$^5$ or X$^{5a}$ but not both may be on the carbon atom and R$^7$ or R$^8$ but not both may be on the nitrogen atom and further provided that when two alkylene bridges are formed then X$^5$ and X$^{5a}$ cannot be on the carbon atom and R$^7$ and R$^8$ cannot be on the nitrogen atom;

or X$^5$ is taken together with X$^{5a}$ and the carbon atom to which they are attached and form a partially saturated or fully saturated 3- to 7-membered ring, or a partially saturated or fully saturated 4- to 8-membered ring having 1 to 4 heteroatoms independently selected from the group consisting of oxygen, sulfur and nitrogen;

or X$^5$ is taken together with X$^{5a}$ and the carbon atom to which they are attached and form a bicyclic ring system consisting of a partially saturated or fully saturated 5- or 6-membered ring, optionally having 1 or 2 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

Z$^1$ is a bond, O or N—X$^2$, provided that when a and b are both 0 then Z$^1$ is not N-X$^2$ or O;

R$^7$ and R$^8$ are independently hydrogen or optionally substituted (C$_1$–C$_6$)alkyl;

where the optionally substituted (C$_1$–C$_6$)alkyl in the definition of R$^7$ and R$^8$ is optionally independently substituted with A$^1$, —C(O)O—(C$_1$–C$_6$)alkyl, —S(O)$_m$(C$_1$–C$_6$)alkyl, 1 to 5 halogens, 1 to 3 hydroxy, 1 to 3 —O—C(O)(C$_1$–C$_{10}$)alkyl or 1 to 3 (C$_1$–C$_6$)alkoxy; or R$^7$ and R$^8$ can be taken together to form —(CH$_2$)$_r$—L—(CH$_2$)$_r$—;

where L is C(X$^2$)(X$^2$), S(O)$_m$ or N(X$^2$);

A$^1$ for each occurrence is independently (C$_5$–C$_7$) cycloalkenyl, phenyl or a partially saturated, fully saturated or fully unsaturated 4- to 8-membered ring optionally having 1 to 4 heteroatoms independently selected from the group consisting of oxygen, sulfur and nitrogen, a bicyclic ring system consisting of a partially saturated, fully unsaturated or fully saturated 5- or 6-membered ring, optionally having 1 to 4 heteroatoms independently selected from the group consisting of nitrogen, sulfur and oxygen, fused to a partially saturated, fully saturated or fully unsaturated 5 or 6-membered ring, optionally having 1 to 4 heteroatoms independently selected from the group consisting of nitrogen, sulfur and oxygen;

A$^1$ for each occurrence is independently optionally substituted, in one or optionally both rings if A$^1$ is a bicyclic ring system, with up to three substituents, each substituent independently selected from the group consisting of F, Cl, Br, I, OCF$_3$, OCF$_2$H, CF$_3$, CH$_3$, OCH$_3$, —OX$^6$, —C(O)N(X$^6$)(X$^6$), —C(O) OX$^6$, oxo, (C$_1$–C$_6$)alkyl, nitro, cyano, benzyl, —S(O)$_m$(C$_1$–C$_6$)alkyl, 1H-tetrazol-5-yl, phenyl, phenoxy, phenylalkyloxy, halophenyl, methylenedioxy, $-N(X^6)(X^6)$, $-N(X^6)C(O)(X^6)$, $-SO_2N(X^6)(X^6)$, $-N(X^6)SO_2$-phenyl, $-N(X^6)SO_2X^6$, $-CONX^{11}X^{12}$, $-SO_2NX^{11}X^{12}$, $-NX^6SO_2X^{12}$, $-NX^6CONX^{11}X^{12}$, $-NX^6SO_2NX^{11}X^{12}$, $-NX^6C(O)X^{12}$, imidazolyl, thiazolyl and tetrazolyl, provided that if $A^1$ is optionally substituted with methylenedioxy then it can only be substituted with one methylenedioxy;

where $X^{11}$ is hydrogen or optionally substituted $(C_1-C_6)$alkyl;

the optionally substituted $(C_1-C_6)$alkyl defined for $X^{11}$ is optionally independently substituted with phenyl, phenoxy, $(C_1C_6)$alkoxycarbonyl, $-S(O)_m(C_1-C_6)$alkyl, 1 to 5 halogens, 1 to 3 hydroxy, 1 to 3 $(C_1-C_{10})$alkanoyloxy or 1 to 3 $(C_1-C_6)$alkoxy;

$X^{12}$ is hydrogen, $(C_1-C_6)$alkyl, phenyl, thiazolyl, imidazolyl, furyl or thienyl, provided that when $X^{12}$ is not hydrogen, $X^{12}$ is optionally substituted with one to three substituents independently selected from the group consisting of Cl, F, $CH_3$, $OCH_3$, $OCF_3$ and $CF_3$;

or $X^{11}$ and $X^{12}$ are taken together to form $-(CH_2)_r-L^1-(CH_2)_r-$;

where $L^1$ is $C(X^2)(X^2)$, O, $S(O)_m$ or $N(X^2)$;

r for each occurrence is independently 1, 2 or 3;

$X^2$ for each occurrence is independently hydrogen, optionally substituted $(C_1-C_6)$alkyl, or optionally substituted $(C_3-C_7)$cycloalkyl, where the optionally substituted $(C_1-C_6)$alkyl and optionally substituted $(C_3-C_7)$cycloalkyl in the definition of $X^2$ are optionally independently substituted with $-S(O)_m(C_1-C_6)$alkyl, $-C(O)OX^3$, 1 to 5 halogens or 1–3 $OX^3$;

$X^3$ for each occurrence is independently hydrogen or $(C_1-C_6)$alkyl;

$X^6$ is independently hydrogen, optionally substituted $(C_1-C_6)$alkyl, $(C_2-C_6)$halogenated alkyl, optionally substituted $(C_3-C_7)$cycloalkyl, $(C_3-C_7)$-halogenatedcycloalkyl, where optionally substituted $(C_1-C_6)$alkyl and optionally substituted $(C_3-C_7)$cycloalkyl in the definition of $X^6$ is optionally independently substituted by 1 or 2 $(C_1-C_4)$alkyl, hydroxyl, $(C_1-C_4)$alkoxy, carboxyl, $CONH_2$, $-S(O)_m(C_1-C_6)$alkyl, carboxylate $(C_1-C_4)$alkyl ester, or 1H-tetrazol-5-yl; or when there are two $X^6$ groups on one atom and both $X^6$ are independently $(C_1-C_6)$alkyl, the two $(C_1-C_6)$alkyl groups may be optionally joined and, together with the atom to which the two $X^6$ groups are attached, form a 4- to 9-membered ring optionally having oxygen, sulfur or $NX^7$;

$X^7$ is hydrogen or $(C_1-C_6)$alkyl optionally substituted with hydroxyl; and m for each occurrence is independently 0, 1 or 2;

with the proviso that:

$X^6$ and $X^{12}$ cannot be hydrogen when it is attached to C(O) or $SO_2$ in the form $C(O)X^6$, $C(O)X^{12}$, $SO_2X^6$ or $SO_2X^{12}$; and when $R^6$ is a bond then L is $N(X^2)$ and each r in the definition $-(CH_2)_r-L-(CH_2)_r-$ is independently 2 or 3.

8. A method of treating sleep disorders in a mammal suffering from sleep disorders comprising administering to said mammal an effective amount of a compound of

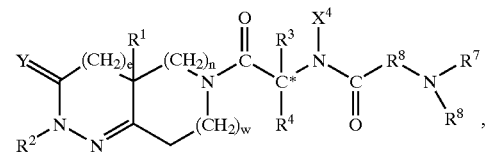

I or the stereoisomeric mixtures, diastereomerically enriched, diastereomerically pure, enantiomerically enriched or enantiomerically pure isomers, or the pharmaceutically acceptable salts and prodrugs thereof, wherein e is 0 or 1;

n and w are each independently 0, 1 or 2;

provided that w and n cannot both be 0 at the same time;

Y is oxygen or sulfur;

$R^1$ is hydrogen, $-CN$, $-(CH_2)_qN(X^6)C(O)X^6$, $-(CH_2)_qN(X^6)C(O)(CH_2)_t-A^1$, $-(CH_2)_qN(X^6)SO_2(CH_2)_t-A^1$, $-(CH_2)_qN(X^6)SO_2X^6$, $-(CH_2)_qN(X^6)C(O)N(X^6)(CH_2)_t-A^1$, $-(CH_2)_qN(X^6)C(O)N(X^6)(X^6)$, $-(CH_2)_qC(O)N(X^6)(X^6)$, $-(CH_2)_qC(O)N(X^6)(CH_2)_t-A^1$, $-(CH_2)_qC(O)OX^6$, $-(CH_2)_qC(O)O(CH_2)_t-A^1$, $-(CH_2)_qOX^6$, $-(CH_2)_qOC(O)X^6$, $-(CH_2)_qOC(O)(CH_2)_t-A^1$, $-(CH_2)_qOC(O)N(X^6)(CH_2)_t-A^1$, $-(CH_2)_qOC(O)N(X^6)(X^6)$, $-(CH_2)_qC(O)X^6$, $-(CH_2)_qC(O)(CH_2)_t-A^1$, $-(CH_2)_qN(X^6)C(O)OX^6$, $-(CH_2)_qN(X^6)SO_2N(X^6)(X^6)$, $-(CH_2)_qS(O)_mX^6$, $-(CH_2)_qS(O)_m(CH_2)_t-A^1$, $-(C_1-C_{10})$alkyl, $-(CH_2)_t-A^1$, $-(CH_2)_q-(C_3-C_7)$cycloalkyl, $-(CH_2)_q-Y^1-(C_1-C_6)$alkyl, $-(CH_2)_q-Y^1-(CH_2)_t-A^1$ or $-(CH_2)_q$-yl-$(CH_2)_t-(C_3-C_7)$cycloalkyl;

where the alkyl and cycloalkyl groups in the definition of $R^1$ are optionally substituted with $(C_1-C_4)$alkyl, hydroxyl, $(C_1-C_4)$alkoxy, carboxyl, $-CONH_2$, $-S(O)_m(C_1-C_6)$alkyl, $-CO_2(C_1-C_4)$alkyl ester, 1H-tetrazol-5-yl or 1, 2 or 3 fluoro;

$Y^1$ is O, $S(O)_m$, $-C(O)NX^6-$, $-CH=CH-$, $-CH\equiv CH-$, $-N(X^6)C(O)-$, $-C(O)NX^6-$, $-C(O)O-$, $-OC(O)N(X^6)-$ or $-OC(O)-$;

q is 0, 1, 2, 3 or 4;

t is 0, 1, 2 or 3;

said $(CH_2)_q$ group and $(CH_2)_t$ group may each be optionally substituted with hydroxyl, $(C_1-C_4)$alkoxy, carboxyl, $-CONH_2$, $-S(O)_m(C_1-C_6)$alkyl, $-CO_2(C_1-C_4)$alkyl ester, 1H-tetrazol-5-yl, 1, 2 or 3 fluoro, or 1 or 2 $(C_1-C_4)$alkyl;

$R^2$ is hydrogen, $(C_1-C_8)$alkyl, $-(C_0-C_3)$alkyl-$(C_3-C_8)$cycloalkyl, $-(C_1-C_4)$alkyl-$A^1$ or $A^1$;

where the alkyl groups and the cycloalkyl groups in the definition of $R^2$ are optionally substituted with hydroxyl, $-C(O)OX^6$, $-C(O)N(X)(X^6)$, $-N(X^6)(X^6)$, $-S(O)_m(C_1-C_6)$alkyl, $-C(O)A^1$, $-C(O)(X^6)$, $CF_3$, CN or 1, 2 or 3 halogen;

$R^3$ is $A^1$, $(C_1-C_{10})$alkyl, $-(C_1-C_6)$alkyl-$A^1$, $-(C_1-C_6)$alkyl-$(C_3-C_7)$cycloalkyl, $-(C_1-C_5)$alkyl-$X^1-(C_1-C_5)$alkyl, $-(C_1-C_5)$alkyl-$X^1-(CO-C_5)$alkyl-$A^1$ or $-(C_1-C_5)$alkyl-$X^1-(C_1-C_5)$alkyl-$(C_3-C_7)$cycloalkyl;

where the alkyl groups in the definition of $R^3$ are optionally substituted with $-S(O)_m(C_1-C_6)$alkyl, $-C(O)OX^3$, 1, 2, 3, 4 or 5 halogens, or 1, 2 or 3 $OX^3$;

$X^1$ is O, $S(O)_m$, $-N(X^2)C(O)-$, $-C(O)N(X^2)-$, $-OC(O)-$, $-C(O)O-$, $-CX^2=CX^2-$, $-N(X^2)C(O)O-$, $-OC(O)N(X^2)-$ or $-C\equiv C-$;

R⁴ is hydrogen, (C₁–C₆)alkyl or (C₃–C₇)cycloalkyl, or R⁴ is taken together with R³ and the carbon atom to which they are attached and form (C₅–C₇)cycloalkyl, (C₅–C₇)cycloalkenyl, a partially saturated or fully saturated 4- to 8 membered ring having 1 to 4 heteroatoms independently selected from the group consisting of oxygen, sulfur and nitrogen, or is a bicyclic ring system consisting of a partially saturated or fully saturated 5- or 6-membered ring, fused to a partially saturated, fully unsaturated or fully saturated 5- or 6 membered ring, optionally having 1 to 4 heteroatoms independently selected from the group consisting of nitrogen, sulfur and oxygen;

X⁴ is hydrogen or (C₁–C₆)alkyl or X⁴ is taken together with R⁴ and the nitrogen atom to which X⁴ is attached and the carbon atom to which R⁴ is attached and form a five to seven membered ring;

R⁵ is a bond or is

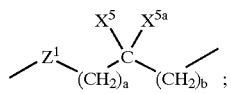

where a and b are independently 0, 1, 2 or 3;

X⁵ and X⁵ᵃ are each independently selected from the group consisting of hydrogen, trifluoromethyl, A¹ and optionally substituted (C₁–C₆)alkyl;

the optionally substituted (C₁–C₆)alkyl in the definition of X⁵ and X⁵ᵃ is optionally substituted with a substituent selected from the group consisting of A¹, OX², —S(O)ₘ(C₁–C₆)alkyl, —C(O)OX², (C₃–C₇)cycloalkyl, —N(X²)(X²) and —C(O)N(X²)(X²);

or the carbon bearing X⁵ or X⁵ᵃ forms one or two alkylene bridges with the nitrogen atom bearing R⁷ and R⁸ wherein each alkylene bridge contains 1 to 5 carbon atoms, provided that when one alkylene bridge is formed then X⁵ or X⁵ᵃ but not both may be on the carbon atom and R⁷ or R⁸ but not both may be on the nitrogen atom and further provided that when two alkylene bridges are formed then X⁵ and X⁵ᵃ cannot be on the carbon atom and R⁷ and R⁸ cannot be on the nitrogen atom;

or X⁵ is taken together with X⁵ᵃ and the carbon atom to which they are attached and form a partially saturated or fully saturated 3- to 7-membered ring, or a partially saturated or fully saturated 4- to 8-membered ring having 1 to 4 heteroatoms independently selected from the group consisting of oxygen, sulfur and nitrogen;

or X⁵ is taken together with X⁵ᵃ and the carbon atom to which they are attached and form a bicyclic ring system consisting of a partially saturated or fully saturated 5- or 6-membered ring, optionally having 1 or 2 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

Z¹ is a bond, O or N—X², provided that when a and b are both 0 then Z¹ is not N—X² or O;

R⁷ and R⁸ are independently hydrogen or optionally substituted (C₁–C₆)alkyl;

where the optionally substituted (C₁–C₆)alkyl in the definition of R⁷ and R⁸ is optionally independently substituted with A¹, —C(O)O—(C₁–C₆)alkyl, —S(O)ₘ(C₁–C₆)alkyl, 1 to 5 halogens, 1 to 3 hydroxy, 1 to 3 —O—C(O)(C₁–C₁₀)alkyl or 1 to 3 (C₁–C₆)alkoxy; or R⁷ and R⁸ can be taken together to form —(CH₂)ᵣ—L—(CH₂)ᵣ—;

where L is C(X²)(X²), S(O)ₘ or N(X²);

A¹ for each occurrence is independently (C₅–C₇)cycloalkenyl, phenyl or a partially saturated, fully saturated or fully unsaturated 4- to 8-membered ring optionally having 1 to 4 heteroatoms independently selected from the group consisting of oxygen, sulfur and nitrogen, a bicyclic ring system consisting of a partially saturated, fully unsaturated or fully saturated 5- or 6-membered ring, optionally having 1 to 4 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

A¹ for each occurrence is independently optionally substituted, in one or optionally both rings if A¹ is a bicyclic ring system, with up to three substituents, each substituent independently selected from the group consisting of F, Cl, Br, I, OCF₃, OCF₂H, CF₃, CH₃, OCH₃, —OXO, —C(O)N(X)(X⁶), —C(O)OX⁶, oxo, (C₁–C₈)alkyl, nitro, cyano, benzyl, —S(O)ₘ(C₁–C₆)alkyl, 1H-tetrazol-5-yl, phenyl, phenoxy, phenylalkyloxy, halophenyl, methylenedioxy, —N(X⁶)(X⁶), —N(X⁶)C(O)(X⁶), —SO₂N(X⁶) (X⁶), —N(X⁶)SO₂-phenyl, —N(X⁶)SO₂X⁶, —CONX¹¹X¹², —SO₂NX¹¹ X¹², —NX⁶SO₂X¹², —NX⁶CONX¹¹X¹², —NX⁶SO₂NX¹¹X¹², —NX⁶C(O)X¹², imidazolyl, thiazolyl and tetrazolyl, provided that if A¹ is optionally substituted with methylenedioxy then it can only be substituted with one methylenedioxy;

where X¹¹ is hydrogen or optionally substituted (C₁–C₆)alkyl;

the optionally substituted (C₁–C₆)alkyl defined for X¹¹ is optionally independently substituted with phenyl, phenoxy, (C₁–C₆)alkoxycarbonyl, —S(O)ₘ(C₁–C₆)alkyl, 1 to 5 halogens, t to 3 hydroxy, 1 to 3 (C₁–C₁₀)alkanoyloxy or 1 to 3 (C₁–C₆)alkoxy;

X¹² is hydrogen, (C₁–C₆)alkyl, phenyl, thiazolyl, imidazolyl, furyl or thienyl, provided that when X¹² is not hydrogen, X¹² is optionally substituted with one to three substituents independently selected from the group consisting of Cl, F, CH₃, OCH₃, OCF₃ and CF₃;

or X¹¹ and X¹² are taken together to form —(CH₂)ᵣ—L¹—(CH₂)ᵣ—;

where L¹ is C(X²)(X²), O, S(O)ₘ or N(X²);

r for each occurrence is independently 1, 2 or 3;

X² for each occurrence is independently hydrogen, optionally substituted (C₁–C₆)alkyl, or optionally substituted (C₃–C₇)cycloalkyl, where the optionally substituted (C₁–C₆)alkyl and optionally substituted (C₃–C₇)cycloalkyl in the definition of X² are optionally independently substituted with —S(O)ₘ(C₁–C₆)alkyl, —C(O)OX³, 1 to 5 halogens or 1–3 OX³;

X³ for each occurrence is independently hydrogen or (C₁–C₆)alkyl;

X⁶ is independently hydrogen, optionally substituted (C₁–C₆)alkyl, (C₂–C₆)halogenated alkyl, optionally substituted $(C_3-C_7)$cycloalkyl, $(C_3-C_7)$-halogenatedcycloalkyl, where optionally substituted $(C_1-C_6)$alkyl and optionally substituted $(C_3-C_7)$cycloalkyl in the definition of $X^6$ is optionally independently substituted by 1 or 2 $(C_1-C_4)$alkyl, hydroxyl, $(C_1-C_4)$alkoxy, carboxyl, $CONH_2$, $-S(O)_m(C_1-C_6)$alkyl, carboxylate $(C_1-C_4)$alkyl ester, or 1H-tetrazol-5-yl; or when there are two $X^6$ groups on one atom and both $X^6$ are independently $(C_1-C_6)$alkyl, the two $(C_1-C_6)$alkyl groups may be optionally joined and, together with the atom to which the two $X^6$ groups are attached, form a 4- to 9-membered ring optionally having oxygen, sulfur or $NX^7$;

$X^7$ is hydrogen or $(C_1-C_6)$alkyl optionally substituted with hydroxyl; and m for each occurrence is independently 0, 1 or 2;

with the proviso that:

$X^6$ and $X^{12}$ cannot be hydrogen when it is attached to $C(O)$ or $SO_2$ in the form $C(O)X^6$, $C(O)X^{12}$, $SO_2X^6$ or $SO_2X^{12}$; and when $R^6$ is a bond then L is $N(X^2)$ and each r in the definition $-(CH_2)_r-L-(CH_2)_r-$ is independently 2 or 3.

* * * * *